United States Patent
Ben-Tsur et al.

(10) Patent No.: US 11,504,024 B2
(45) Date of Patent: Nov. 22, 2022

(54) GASTROINTESTINAL TREATMENT SYSTEM INCLUDING A VIBRATING CAPSULE, AND METHOD OF USE THEREOF

(71) Applicant: Vibrant Ltd., Yokneam (IL)

(72) Inventors: Lior Ben-Tsur, Netanya (IL); Shai Molnar, Shorashim (IL); Roni Shabat, Kibbutz Yizra'el (IL)

(73) Assignee: Vibrant Ltd., Yokneam (IL)

( * ) Notice: Subject to any disclaimer, the term of this patent is extended or adjusted under 35 U.S.C. 154(b) by 0 days.

(21) Appl. No.: 17/461,053

(22) Filed: Aug. 30, 2021

(65) Prior Publication Data

US 2021/0386316 A1 Dec. 16, 2021

(51) Int. Cl.
*A61H 21/00* (2006.01)
*A61B 5/07* (2006.01)
(Continued)

(52) U.S. Cl.
CPC ............ *A61B 5/073* (2013.01); *A61B 5/42* (2013.01); *A61B 5/4836* (2013.01); *A61H 23/02* (2013.01);
(Continued)

(58) Field of Classification Search
CPC .... A61H 21/00; A61H 23/02; A61H 23/0263; A61H 2205/083; A61B 5/073;
(Continued)

(56) References Cited

U.S. PATENT DOCUMENTS

| | | |
|---|---|---|
| 3,485,235 A | 12/1969 | Felson |
| 4,239,040 A | 12/1980 | Hosoya et al. |

(Continued)

FOREIGN PATENT DOCUMENTS

| | | |
|---|---|---|
| CN | 1829466 A | 9/2006 |
| CN | 101810481 A | 8/2010 |

(Continued)

OTHER PUBLICATIONS

Machine Translation for (by Google Patents) CN101810481 published on Aug. 25, 2010.

(Continued)

*Primary Examiner* — Timothy A Stanis
*Assistant Examiner* — Christopher E Miller
(74) *Attorney, Agent, or Firm* — Momentum IP; Marc Van Dyke

(57) ABSTRACT

A gastrointestinal treatment system including a gastrointestinal capsule adapted to treat a subject following ingestion of the gastrointestinal capsule. The gastrointestinal capsule includes: (a) a housing; (b) a vibrating agitator, powered by the battery, the vibrating agitator adapted such that, in a first vibrating mode of operation, the housing exerts vibrations on an environment surrounding the capsule; (c) a power supply disposed within the housing and adapted to power the vibrating agitator; and (d) a controller adapted, in response to receipt of an activation input, to activate the vibrating agitator to operate in the first vibrating mode of operation at at least one predetermined time of day. The system and method may be used to treat an ailment of the gastrointestinal tract and/or to mitigate at least one symptom of jetlag in a subject travelling from an origin location to a destination location.

17 Claims, 20 Drawing Sheets

(51) Int. Cl.
*A61B 5/00* (2006.01)
*A61H 23/02* (2006.01)

(52) U.S. Cl.
CPC .. *A61H 23/0263* (2013.01); *A61B 2560/0214* (2013.01); *A61B 2562/0219* (2013.01); *A61B 2562/0247* (2013.01); *A61B 2562/0271* (2013.01); *A61B 2562/162* (2013.01); *A61H 2201/1207* (2013.01); *A61H 2205/083* (2013.01)

(58) Field of Classification Search
CPC ... A61B 5/42; A61B 1/00016; A61B 1/00156; A61B 2562/162; A61B 5/6861; A61M 31/002
See application file for complete search history.

(56) References Cited

U.S. PATENT DOCUMENTS

| | | | |
|---|---|---|---|
| 4,507,115 A | 3/1985 | Kambara et al. | |
| 5,170,801 A | 12/1992 | Casper et al. | |
| 5,188,104 A * | 2/1993 | Wernicke | A61N 1/36007 |
| | | | 607/40 |
| 6,026,326 A * | 2/2000 | Bardy | A61N 1/36007 |
| | | | 607/40 |
| 6,453,199 B1 | 9/2002 | Kobozev | |
| 6,632,216 B2 | 10/2003 | Houzego et al. | |
| 6,776,165 B2 | 8/2004 | Jin | |
| 6,911,004 B2 | 6/2005 | Kim et al. | |
| 6,929,363 B2 | 8/2005 | Sakai et al. | |
| 6,984,205 B2 | 1/2006 | Gazdzinski | |
| 7,076,284 B2 | 7/2006 | Segawa et al. | |
| 7,354,397 B2 | 4/2008 | Fujita et al. | |
| 7,510,537 B2 | 3/2009 | Imboden et al. | |
| 7,511,733 B2 | 3/2009 | Takizawa et al. | |
| 7,623,904 B2 | 11/2009 | Uchiyama et al. | |
| 7,637,864 B2 | 12/2009 | Yokoi et al. | |
| 7,797,033 B2 | 9/2010 | DAndrea et al. | |
| 7,942,811 B2 | 5/2011 | Segawa et al. | |
| 7,957,807 B2 * | 6/2011 | Starkebaum | A61N 1/36007 |
| | | | 607/40 |
| 8,021,356 B2 | 9/2011 | Uchiyama et al. | |
| 8,021,357 B2 | 9/2011 | Tanaka et al. | |
| 8,021,384 B2 | 9/2011 | Weiss et al. | |
| 8,036,748 B2 | 10/2011 | Zdeblick et al. | |
| 8,038,600 B2 | 10/2011 | Uchiyama et al. | |
| 8,147,482 B2 | 4/2012 | Shimizu et al. | |
| 8,202,697 B2 | 6/2012 | Holmes | |
| 8,216,130 B2 | 7/2012 | Glukhovsky et al. | |
| 8,295,932 B2 | 10/2012 | Bitton et al. | |
| 8,306,592 B2 | 11/2012 | Takizawa et al. | |
| 8,518,022 B2 | 8/2013 | Trovato et al. | |
| 8,597,278 B2 | 12/2013 | Trovato et al. | |
| 8,701,677 B2 | 4/2014 | Duan et al. | |
| 8,755,888 B2 | 6/2014 | Voznesensky et al. | |
| 8,852,172 B2 | 10/2014 | Dijksman et al. | |
| 8,945,005 B2 | 2/2015 | Hafezi et al. | |
| 9,078,799 B2 | 7/2015 | Shohat et al. | |
| 9,156,169 B2 | 10/2015 | Duan et al. | |
| 9,232,909 B2 | 1/2016 | Duan et al. | |
| 9,511,211 B2 | 12/2016 | Tange et al. | |
| 9,532,923 B2 | 1/2017 | Shohat et al. | |
| 9,538,937 B2 | 1/2017 | Rohde et al. | |
| 9,572,746 B2 | 2/2017 | Asfora | |
| 9,707,150 B2 | 7/2017 | Shabbat | |
| 9,750,923 B2 | 9/2017 | Niichel et al. | |
| 9,770,588 B2 | 9/2017 | Bettinger | |
| 9,919,152 B2 | 3/2018 | Levine et al. | |
| 9,986,898 B2 | 6/2018 | Duan et al. | |
| 9,999,415 B2 | 6/2018 | Duan et al. | |
| 10,070,854 B2 | 9/2018 | Duan et al. | |
| 10,076,234 B2 | 9/2018 | Duan et al. | |
| 10,118,035 B2 | 11/2018 | Perez et al. | |
| 10,143,364 B2 | 12/2018 | Duan et al. | |
| 10,314,514 B2 | 6/2019 | Duan | |
| 10,478,047 B2 | 11/2019 | Duan et al. | |
| 10,478,373 B2 | 11/2019 | Duan et al. | |
| 10,500,127 B2 | 12/2019 | Duan et al. | |
| 10,517,466 B2 | 12/2019 | Ye et al. | |
| 10,531,788 B2 | 1/2020 | Wang et al. | |
| 10,869,811 B2 | 12/2020 | Duan et al. | |
| 10,874,339 B2 | 12/2020 | Chavan et al. | |
| 10,888,277 B1 | 1/2021 | Ben-Tsur et al. | |
| 10,905,378 B1 | 2/2021 | Ben-Tsur et al. | |
| 2002/0099310 A1 | 7/2002 | Kimchy et al. | |
| 2002/0132226 A1 | 9/2002 | Nair et al. | |
| 2002/0161414 A1 * | 10/2002 | Flesler | A61N 1/08 |
| | | | 607/40 |
| 2004/0253304 A1 | 12/2004 | Gross et al. | |
| 2004/0267240 A1 | 12/2004 | Gross et al. | |
| 2005/0058701 A1 | 3/2005 | Gross et al. | |
| 2006/0211963 A1 | 9/2006 | Spirk et al. | |
| 2006/0247718 A1 * | 11/2006 | Starkebaum | A61N 1/372 |
| | | | 607/40 |
| 2006/0270899 A1 | 11/2006 | Amirana | |
| 2006/0276729 A1 | 12/2006 | Reed et al. | |
| 2007/0015952 A1 | 1/2007 | Chang et al. | |
| 2007/0238940 A1 * | 10/2007 | Amirana | A61B 5/4839 |
| | | | 600/302 |
| 2008/0161639 A1 | 7/2008 | Katayama et al. | |
| 2008/0188837 A1 * | 8/2008 | Belsky | A61K 9/0097 |
| | | | 604/890.1 |
| 2008/0269664 A1 * | 10/2008 | Trovato | A61B 1/041 |
| | | | 604/20 |
| 2008/0275430 A1 | 11/2008 | Belsky et al. | |
| 2008/0281238 A1 | 11/2008 | Oohashi et al. | |
| 2009/0281380 A1 | 11/2009 | Miller et al. | |
| 2009/0306633 A1 * | 12/2009 | Trovato | A61B 1/041 |
| | | | 604/891.1 |
| 2009/0318841 A1 * | 12/2009 | Shohat | A61H 23/02 |
| | | | 601/46 |
| 2010/0217079 A1 | 8/2010 | Tichy | |
| 2010/0222670 A1 | 9/2010 | Demierre et al. | |
| 2011/0208011 A1 | 8/2011 | Ben-Horin | |
| 2011/0319727 A1 | 12/2011 | Ishihara | |
| 2012/0232460 A1 * | 9/2012 | Raven | A61F 5/0076 |
| | | | 604/9 |
| 2012/0259389 A1 * | 10/2012 | Starkebaum | A61B 5/0006 |
| | | | 607/2 |
| 2013/0041299 A1 * | 2/2013 | Lacy | A61H 21/00 |
| | | | 601/46 |
| 2013/0158452 A1 | 6/2013 | Juto et al. | |
| 2013/0253387 A1 | 9/2013 | Bonutti et al. | |
| 2013/0267788 A1 | 10/2013 | Duan et al. | |
| 2014/0221741 A1 | 8/2014 | Wang et al. | |
| 2015/0065926 A1 | 3/2015 | Nakamura et al. | |
| 2015/0073315 A1 * | 3/2015 | Shabbat | A61H 23/02 |
| | | | 601/46 |
| 2015/0223727 A1 | 8/2015 | Kimchy et al. | |
| 2015/0380140 A1 | 12/2015 | Duan et al. | |
| 2016/0183878 A1 | 6/2016 | Weast et al. | |
| 2016/0303133 A1 | 10/2016 | Dudley et al. | |
| 2017/0273863 A1 | 9/2017 | Shabbat | |
| 2017/0296425 A1 * | 10/2017 | Duan | A61F 5/0073 |
| 2017/0296428 A1 * | 10/2017 | Duan | A61H 23/0254 |
| 2018/0168490 A1 | 6/2018 | Jones et al. | |
| 2018/0185238 A1 * | 7/2018 | Ilan | A61H 23/02 |
| 2019/0224070 A1 | 7/2019 | Ben-Tsur et al. | |
| 2020/0315541 A1 | 10/2020 | Ben-Tsur et al. | |

FOREIGN PATENT DOCUMENTS

| | | |
|---|---|---|
| CN | 102743174 A | 10/2012 |
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |

(56) References Cited

FOREIGN PATENT DOCUMENTS

| | | | | |
|---|---|---|---|---|
| CN | 202875332 U | 4/2013 | | |
| CN | 103222842 A | 7/2013 | | |
| CN | 203634116 U | 6/2014 | | |
| CN | 104898850 A | 9/2015 | | |
| CN | 105025245 A | 11/2015 | | |
| CN | 105079970 A | 11/2015 | | |
| CN | 105380777 A | 3/2016 | | |
| CN | 105411505 A | 3/2016 | | |
| CN | 105411562 A | * 3/2016 | ............... | A61B 5/03 |
| CN | 105434155 A | 3/2016 | | |
| CN | 105434155 A | * 3/2016 | | |
| CN | 205108749 U | 3/2016 | | |
| CN | 205286889 U | 6/2016 | | |
| CN | 105939451 A | 9/2016 | | |
| CN | 105942959 A | 9/2016 | | |
| CN | 105996961 A | 10/2016 | | |
| CN | 105997466 A | * 10/2016 | ............ | A61B 5/073 |
| CN | 106056588 A | 10/2016 | | |
| CN | 106097335 A | 11/2016 | | |
| CN | 106137760 A | 11/2016 | | |
| CN | 106204599 A | 12/2016 | | |
| CN | 205758500 U | 12/2016 | | |
| CN | 106333837 A | * 1/2017 | ............ | A61H 21/00 |
| CN | 106373137 A | 2/2017 | | |
| CN | 106377406 A | 2/2017 | | |
| CN | 106377406 A | * 2/2017 | ............ | A61H 21/00 |
| CN | 205913317 U | 2/2017 | | |
| CN | 205928774 U | 2/2017 | | |
| CN | 106923787 A | 7/2017 | | |
| CN | 106934799 A | 7/2017 | | |
| CN | 107174188 A | 9/2017 | | |
| CN | 107233580 A | 10/2017 | | |
| CN | 107240091 A | 10/2017 | | |
| CN | 107375951 A | 11/2017 | | |
| EP | 2814376 A1 | 12/2014 | | |
| EP | 2987447 A1 | 2/2016 | | |
| EP | 2995240 A1 | 3/2016 | | |
| JP | 2001062397 A | 3/2001 | | |
| JP | 2002163359 A | 6/2002 | | |
| JP | 2005052502 A | 3/2005 | | |
| JP | 2010503451 A | 2/2010 | | |
| JP | 2010246703 A | 11/2010 | | |
| JP | 2013535756 A | 9/2013 | | |
| WO | 2006025013 A1 | 3/2006 | | |
| WO | 2006045011 A2 | 4/2006 | | |
| WO | 2007013059 A2 | 2/2007 | | |
| WO | 2008012700 A1 | 1/2008 | | |
| WO | 2009063375 A1 | 5/2009 | | |
| WO | 2013121276 A1 | 8/2013 | | |
| WO | WO-2013153859 A1 | * 10/2013 | ......... | A61B 1/00006 |
| WO | 2018055487 A1 | 3/2018 | | |

OTHER PUBLICATIONS

Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105380777 published on Mar. 9, 2016.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205286889 published on Jun. 8, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2002163359 published on Jun. 7, 2002.
Machine Translation (by Google Patents) for JP 2005052502 published on Mar. 3, 2005.
Machine Translation (by Google Patents) for JP 2010246703 published on Nov. 4, 2010.
Machine Translation (by Google Patents) for JP 2010503451 published on Feb. 4, 2010.
Machine Translation (by Google Patents) for JP 2013535756 published on Sep. 12, 2013.
Smart capsule to target colon diseases, Ben Gruber, Sep. 30, 2015 https://www.reuters.com/article/us-smart-capsule-colon-idUSKCN0RU1ZE20150930.

(56) References Cited

OTHER PUBLICATIONS

Digestive Disease Week. "Vibrating capsule shows promising results in treating chronic constipation: Non-pharmacological therapy." ScienceDaily. ScienceDaily, May 3, 2014. <www.sciencedaily.com/releases/2014/05/140503141219.htm>.
International Search Report PCT/IB20190/52529 dated Jul. 25, 2019.
Written Opinion of PCT/IB20190/52529 dated Jul. 25, 2019.
Machine Translation for (by Google Patents) CN105434155 published on Mar. 30, 2016.
Machine Translation for (by Google Patents) CN106377406 published on Feb. 8, 2017.

* cited by examiner

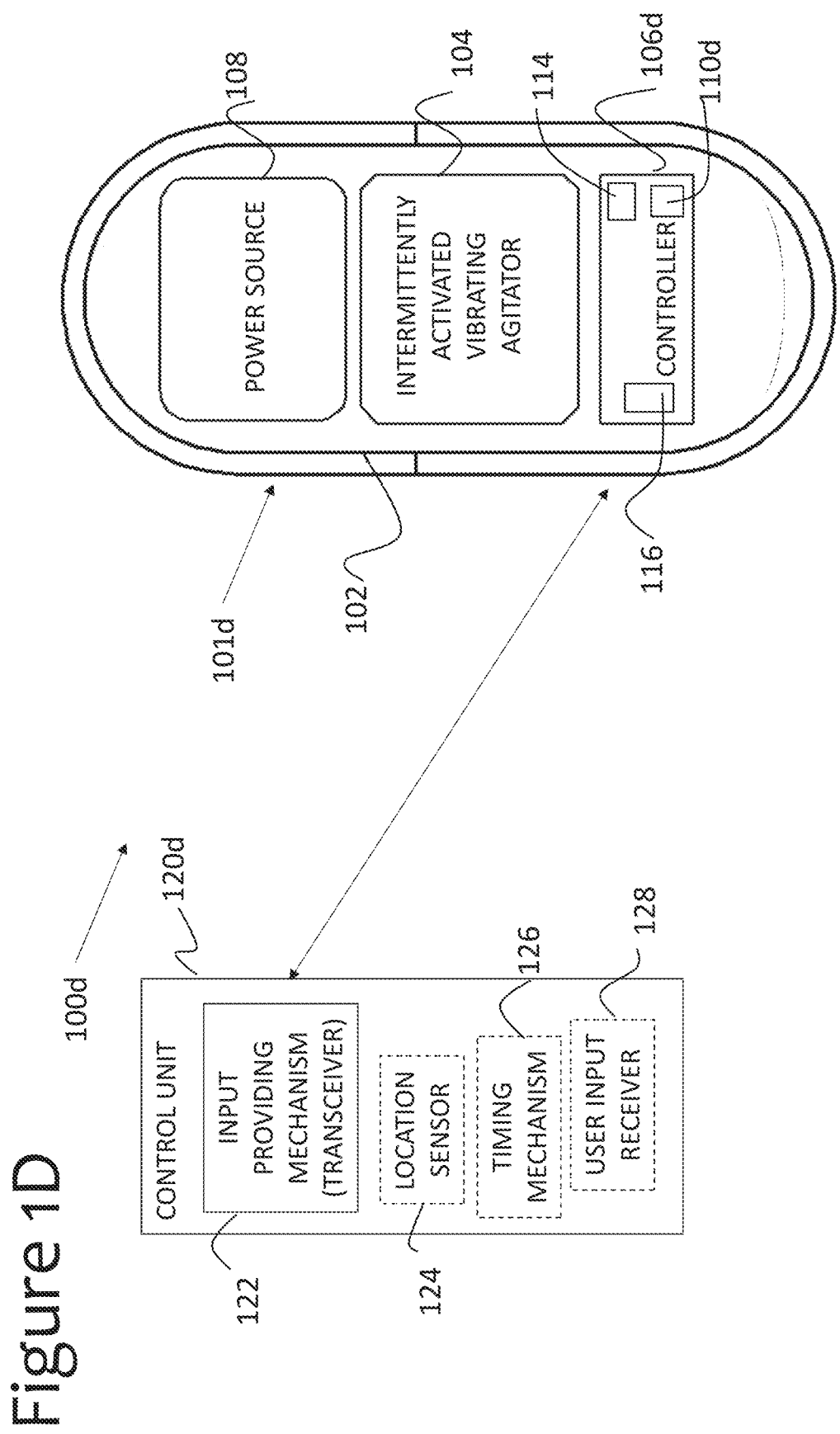

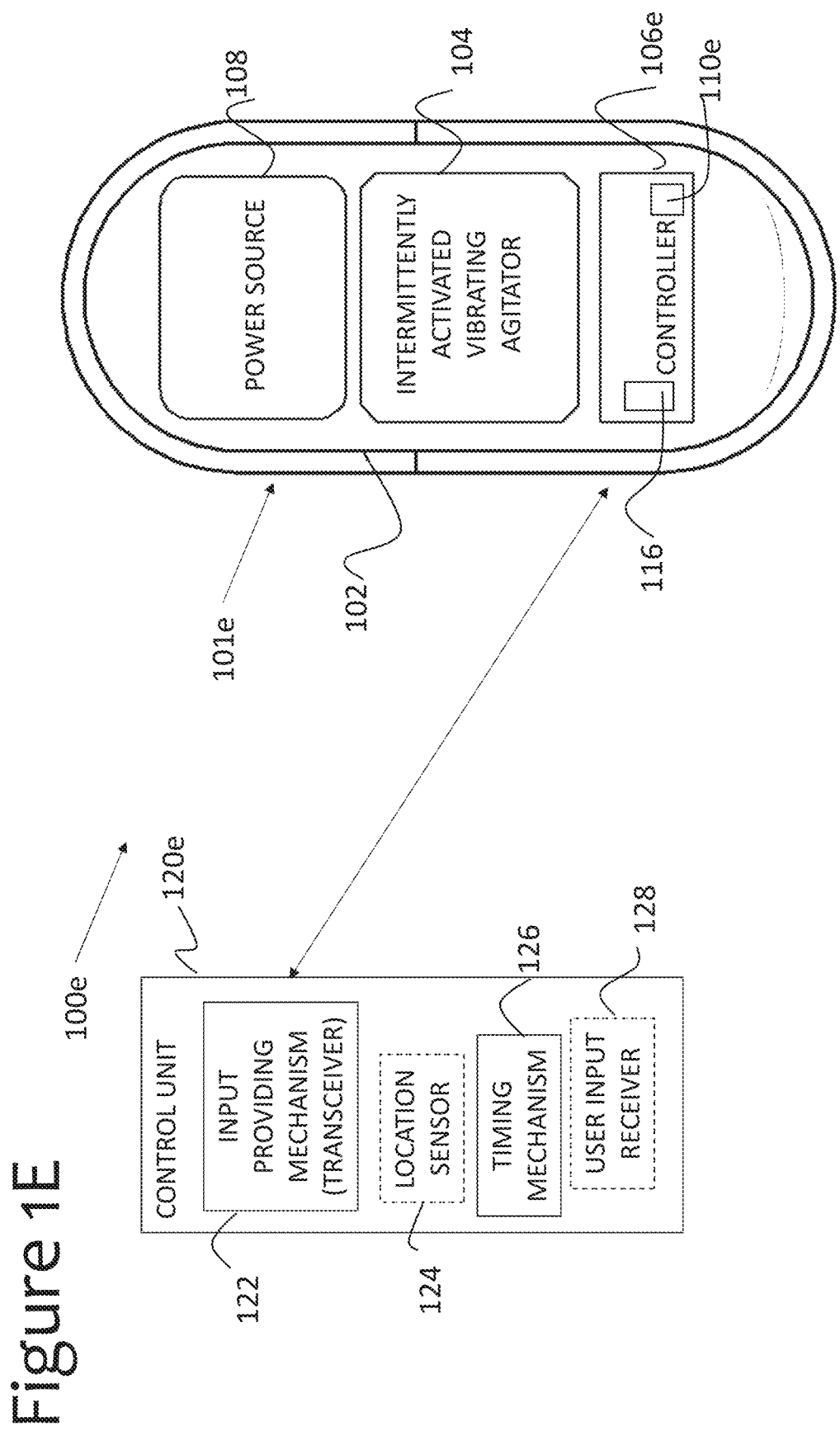

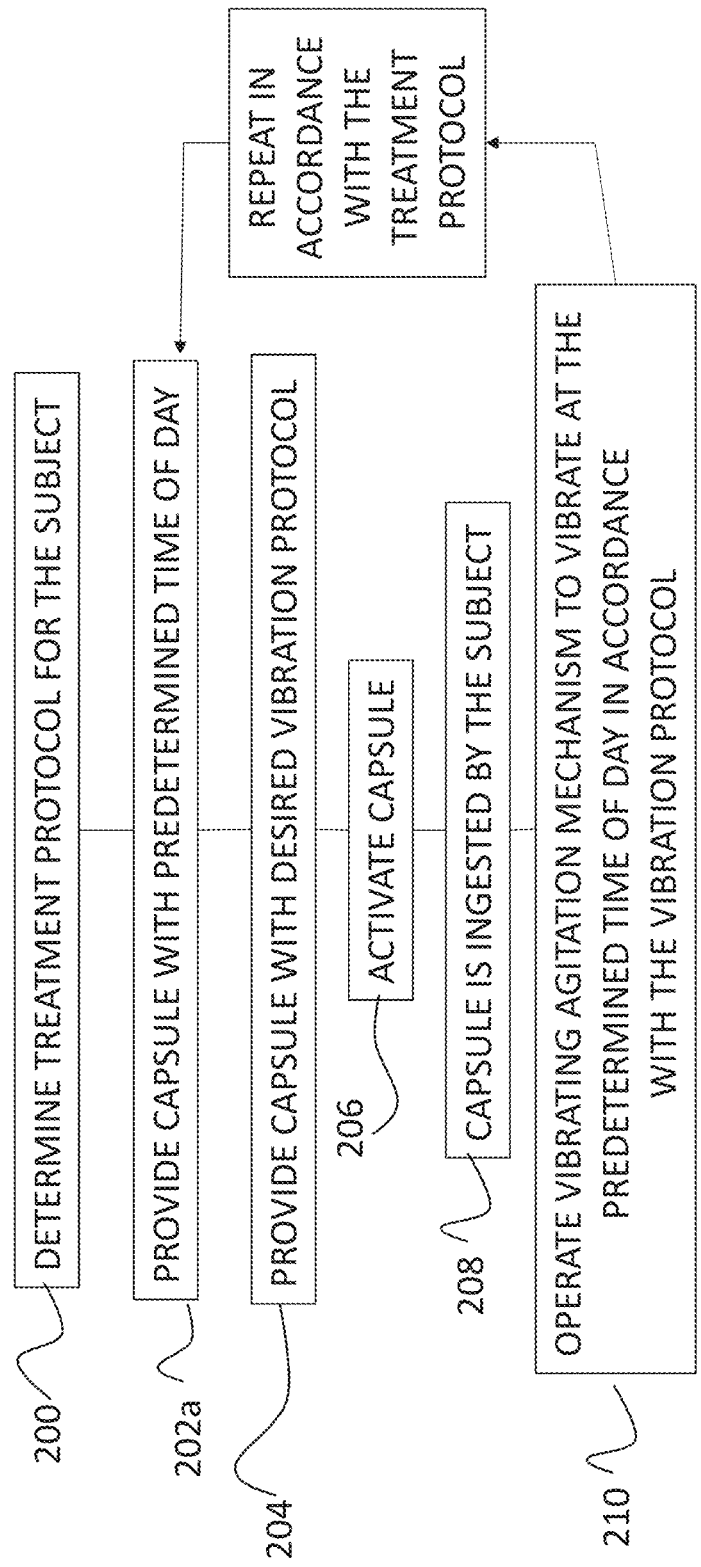

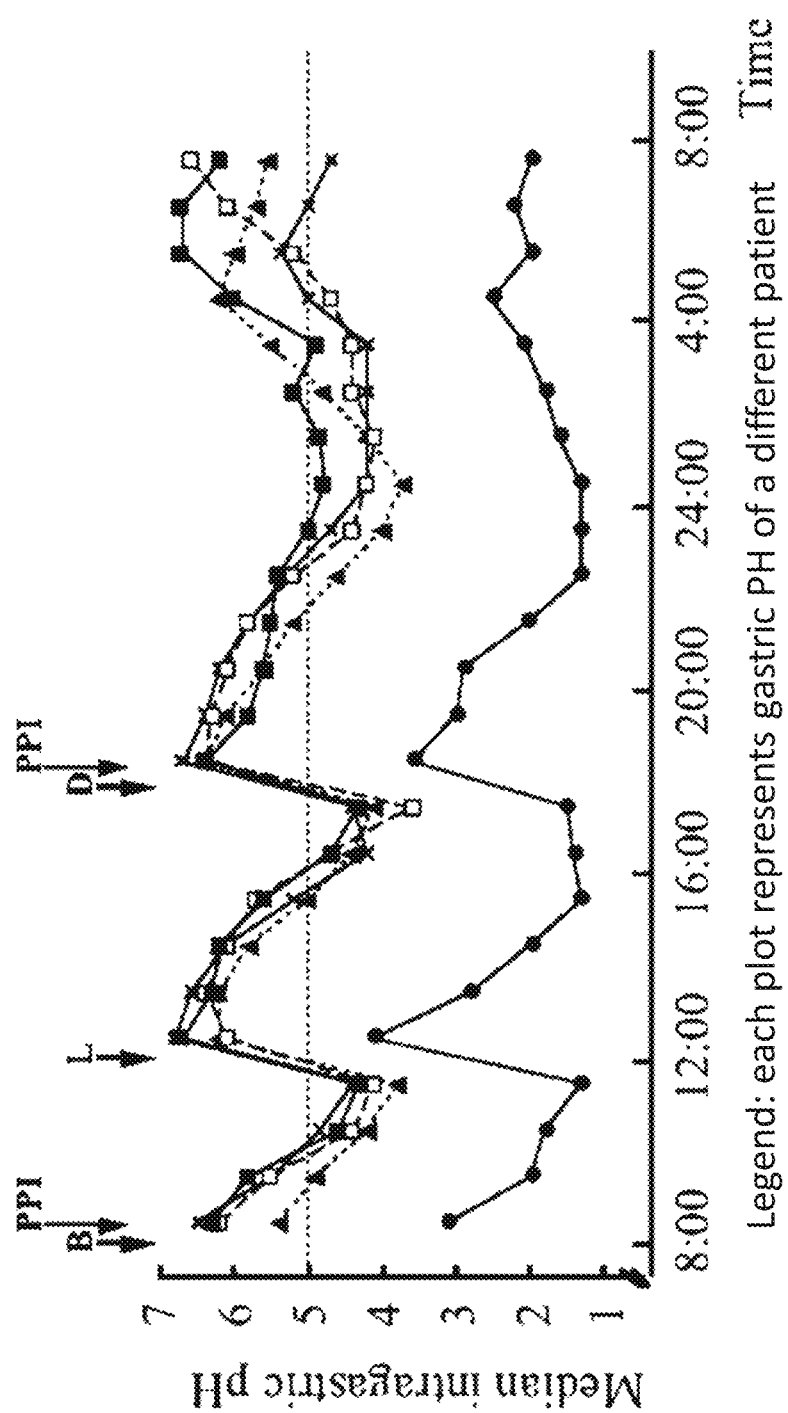

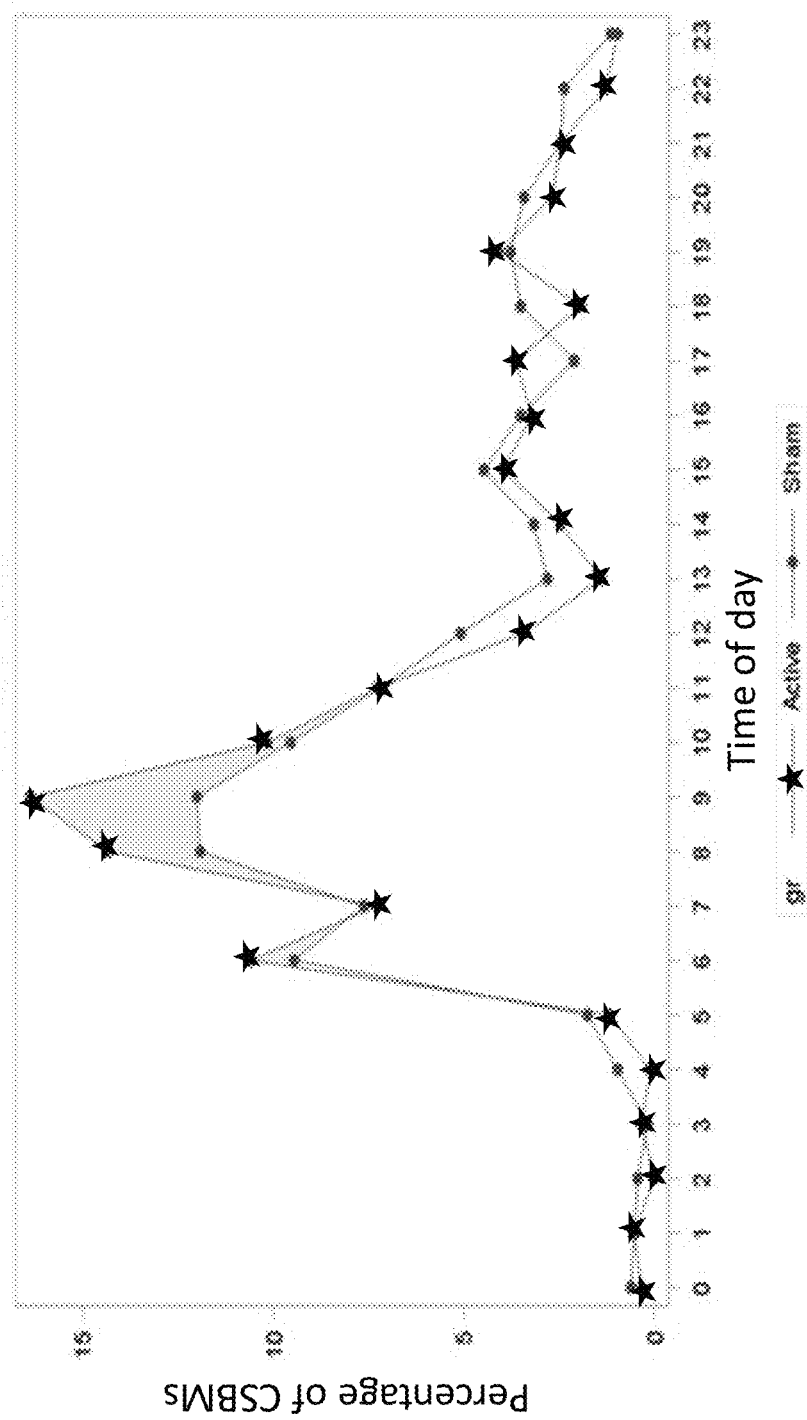

GASTROINTESTINAL TREATMENT SYSTEM INCLUDING A VIBRATING CAPSULE, AND METHOD OF USE THEREOF

FIELD OF THE INVENTION

The present invention relates in general to gastrointestinal treatment systems including one or more vibrating capsules, and to methods of use thereof, and more particularly, to gastrointestinal treatment systems and methods in which the one or more capsules vibrate, or are adapted to vibrate, at one or more specific times of day. The present invention further relates in general to a method and a system for mitigating at least one effect of jetlag, and specifically to a method for mitigating jetlag using a gastrointestinal treatment system including one or more vibrating capsules.

SUMMARY OF THE INVENTION

In accordance with an embodiment of the present invention, there is provided a gastrointestinal treatment system including a gastrointestinal capsule adapted to treat a gastrointestinal tract of a subject following ingestion of the gastrointestinal capsule, the gastrointestinal capsule including:
(a) a housing;
(b) a vibrating agitator adapted such that, in a first vibrating mode of operation, the housing exerts vibrations on an environment surrounding the capsule;
(c) a power supply disposed within the housing and adapted to power the vibrating agitator; and
(d) a controller adapted, in response to receipt of an activation input, to activate the vibrating agitator to operate in the first vibrating mode of operation at at least one predetermined time of day.

In accordance with another embodiment of the present invention, there is provided a gastrointestinal treatment system including a gastrointestinal capsule adapted to treat a gastrointestinal tract of a subject following ingestion of the gastrointestinal capsule, the gastrointestinal capsule including:
(a) a housing;
(b) a vibrating agitator adapted such that, in a first vibrating mode of operation, the housing exerts vibrations on an environment surrounding the capsule;
(c) a power supply disposed within the housing and adapted to power the vibrating agitator; and
(d) a controller adapted, when the capsule is in an operative state, to activate the vibrating agitator to operate in the first vibrating mode of operation at at least one predetermined time of day.

In some embodiments, the capsule is adapted to be in the operative state following receipt of an activation input, which transitions the capsule from an inoperative state to an operative state.

In some embodiments, the subject is travelling from an origin location to a destination location, and the system is adapted to mitigate jetlag of the subject.

In some such embodiments, the controller is adapted to activate the vibrating agitator to operate in the first vibrating mode of operation at at least one predetermined time of day according to a time zone of the origin location.

In some such embodiments, the controller is adapted to activate the vibrating agitator to operate in the first vibrating mode of operation at at least one predetermined time of day according to a time zone of the destination location.

In some such embodiments, the controller is adapted to activate the vibrating agitator to operate in the first vibrating mode of operation at a first time of day of the at least one predetermined time of day according to a time zone of the origin location and at a second time of day of the at least one predetermined time of day according to a time zone of the destination location.

In some embodiments, the predetermined time of day is selected according to a circadian cycle of the subject.

In some embodiments, the predetermined time of day is selected according to a gastric pH profile of the subject.

In some embodiments, the capsule includes at least one timing mechanism, and is devoid of sensors for sensing an environment thereof.

In some embodiments, the at least one timing mechanism comprises a timer.

In some embodiments, the at least one timing mechanism comprises a clock. In some embodiments, the at least one timing mechanism is associated with a positioning system such as GPS.

In some embodiments, the controller is adapted, in response to the activation input, to wait a predetermined delay time, and following the predetermined delay time, at a time coinciding with the at least one predetermined time of day, to activate the vibrating agitator to operate in the first vibration mode of operation.

In some embodiments, the capsule further includes at least one sensor adapted to provide the activation input.

In some embodiments, the at least one sensor includes an illumination sensor adapted to provide the activation input upon identification of transition of the capsule from an illuminated environment to a dark environment.

In some embodiments, the at least one sensor includes a pressure sensor adapted to provide the activation input upon identification of pressure applied to the capsule, which pressure is indicative of the capsule moving through a pharynx of the subject.

In some embodiments, the at least one sensor includes a temperature sensor adapted to provide the activation input upon identification of transition of the capsule from an area with ambient temperature to an area with a human body temperature.

In some embodiments, the at least one sensor includes an accelerometer adapted to provide the activation input upon identification of an activation motion carried out by a user of the gastrointestinal capsule.

In some embodiments, the at least one sensor includes a moisture sensor adapted to provide the activation input upon identification of transition of the capsule from a dry environment to a humid environment.

In some embodiments, the capsule further includes a timing mechanism. In some embodiments, in response to the activation input, the controller is adapted to activate operation of the timing mechanism to track a time of day so as to identify the at least one predetermined time of day for activation of the vibration agitator. In some embodiments, in response to the activation input, the controller is adapted to activate operation of the timing mechanism to wait a predetermined duration prior to activation of vibration agitator, such that activation of the vibration agitator occurs at the at least one predetermined time of day.

In some embodiments, the system further includes a control unit, adapted to provide the activation input to the controller of the gastrointestinal capsule.

In some embodiments, the control unit is adapted to provide the activation input following ingestion of the gastrointestinal capsule by the subject. In other embodiments, the control unit is adapted to provide the activation input prior to ingestion of the gastrointestinal capsule by the subject.

In some embodiments, the control unit is adapted to provide to the controller a current time of day, and the controller is adapted to compute a delay time from the current time of day to the at least one predetermined time of day, and to activate the vibrating agitator following the delay time.

In some embodiments, the control unit further includes a timing device, and is adapted to provide to the capsule, as the activation input, an input signal indicating a current time of day being the at least one predetermined time of day, and the controller is adapted, upon receipt of the input signal, to activate the vibrating agitator to operate in the first vibrating mode of operation.

In some embodiments, the timing mechanism associated with the controller is a timer, and the control unit is adapted to provide to the controller, as the activation input, a delay time from the current time of day to the at least one predetermined time of day, and the controller is adapted to activate the vibrating agitator following the delay time.

In some embodiments, the current time of day is a time of day at an origin location of the subject. In other embodiments, the current time of day is a time of day at a destination location of the subject.

In some embodiments, the activation input includes the at least one predetermined time of day. In some embodiments, the activation input includes a delay time from a current time to the at least one predetermined time of day.

In some embodiments, the at least one predetermined time of day includes at least one default predetermined time of day. In some embodiments, the at least one predetermined time of day includes at least one time of day coinciding with at least one predetermined mealtime.

In some embodiments, the at least one predetermined time of day includes at least one time of day coinciding with at least one predetermined mealtime in a time zone of the origin location of the subject.

In some embodiments, the at least one predetermined time of day includes at least one time of day coinciding with at least one predetermined mealtime in a time zone of the destination location of the subject.

In some embodiments, the at least one predetermined mealtime includes at least one default mealtime.

In some embodiments, the at least one default mealtime includes a default breakfast time. In some embodiments, the default breakfast time is between 5 am and 10 am, between 6 am and 10 am, between 6 am and 9 am, between 6 am and 8 am, between 7 am and 10 am, between 7 am and 9 am, and between 7 am and 8 am.

In some embodiments, the at least one default mealtime includes a default lunchtime. In some embodiments, the default lunchtime is between 12 pm and 3 pm, between 12 pm and 2 pm, or between 1 pm and 3 pm.

In some embodiments, the at least one default mealtime includes a default suppertime. In some embodiments, the default suppertime is between 6 pm and 10 pm, between 7 pm and 10 pm, between 8pm and 10 pm, between 6 pm and 9 pm, between 7 pm and 9 pm, or between 6 pm and 8 pm.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments, activation of the vibrating agitator to operate in the first vibrating mode of operation at the at least one predetermined time of day triggers a spontaneous bowel movement (SBM) in the user, which SBM occurs at a later time of day than the at least one predetermined time of day.

In some embodiments, activation of the vibrating agitator to operate in the first vibrating mode of operation at the at least one predetermined time of day triggers a complete spontaneous bowel movement (CSBM) in the user, which CSBM occurs at a later time of day than the at least one predetermined time of day. In some such embodiments, the at least one predetermined time of day is lunchtime, for example between 12 pm to 3 pm or between 12 pm to 2 pm, and the later time of day is dinnertime, for example between 6 pm and 9 pm.

In some embodiments, at least one of the capsule and the control unit includes an input mechanism for receiving subject-specific input from the subject, and wherein the at least one predetermined mealtime includes at least one subject-specific mealtime of the subject.

In some such embodiments, the subject-specific mealtime of the subject is a subject-specific mealtime in the time zone of the origin location of the subject. In other such embodiments, the subject-specific mealtime of the subject is a subject-specific mealtime in the time zone of the destination location of the subject.

In some embodiments, at least one of the capsule and the control unit includes a location sensor adapted to identify a geographical region in which the capsule is located, and wherein the at least one predetermined time of day includes at least one region-specific time of day of the geographical region in which the capsule is located. In some such embodiments, the at least one region-specific time of day includes at least one region-specific mealtime of the geographical region in which the capsule is located.

In some such embodiments, the geographical region is a geographical region of the origin location of the subject. In other such embodiments, the geographical region is a geographical region of the destination location of the subject.

In some embodiments, the activation input additionally includes a vibration protocol to be used by the vibrating agitator during the first vibrating mode of operation.

In some embodiments, the controller is adapted to activate the agitation vibration mechanism to operate in the first vibrating mode of operation at the at least one predetermined time of day only if a minimum delay duration has passed between receipt of the activation input and the at least one predetermined time of day.

In some embodiments, the vibrating agitator includes at least a radial agitator adapted, in the first vibrating mode of operation, to exert radial forces on the housing, in a radial direction with respect to the longitudinal axis of the housing, thereby to cause the vibrations exerted by the housing. In some embodiments, the radial agitator includes an unbalanced weight attached to a shaft of an electric motor powered by the power supply.

In some embodiments, the vibrating agitator includes at least an axial agitator adapted, in the first vibrating mode of operation, to exert axial forces on the housing, in an axial direction with respect to the longitudinal axis of the housing, thereby to cause the vibrations exerted by the housing. In some embodiments, the axial agitator includes an electric motor powered by the power supply and an urging mechanism, associated with, and driven by, the electric motor, the urging mechanism adapted to exert the axial forces. In some embodiments, the urging mechanism is adapted to exert the axial forces in opposite directions. In some embodiments, the urging mechanism is adapted to deliver at least a portion of the axial forces in a knocking mode.

In some embodiments, the vibrating agitator is adapted in the first vibrating mode of operation, to exert radial forces on the housing in a radial direction with respect to the longitudinal axis of the housing and to exert axial forces on the housing in an axial direction with respect to the longitudinal axis of the housing, thereby to cause the vibrations exerted by the housing. In some embodiments, the vibrating agitator includes a radial agitator adapted to exert the radial forces and a separate axial agitator adapted to exert the axial forces. In other embodiments, the vibrating agitator includes a single agitator adapted to exert the radial forces and the axial forces.

In some embodiments, the housing includes first and second members, and the vibrating agitator includes a mechanism adapted to effect vibrations by moving the first member of the housing in the opposite direction relative to the second member of the housing.

In some embodiments, the vibrating mode of operation including a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours. In some embodiments, the cumulative duration is dependent on properties of the battery.

In some embodiments, the vibrating agitator is configured such that a net force exerted by the housing on the environment is in the range of 50 grams-force to 600 grams-force.

In some embodiments, the vibrating agitator is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the controlling of the vibrating agitator is effected so as to effect a mechanical stimulation of the wall of the gastrointestinal tract during the at least one predetermined time of day.

In accordance with another embodiment of the present invention there is provided a gastrointestinal capsule adapted to treat a gastrointestinal tract of a subject following ingestion of the gastrointestinal capsule, the gastrointestinal capsule including:
 (a) a housing;
 (b) a vibrating agitator adapted such that, in a first vibrating mode of operation, the housing exerts vibrations on an environment surrounding the capsule;
 (c) a power supply disposed within the housing and adapted to power the vibrating agitator;
 (d) at least one sensor adapted to identify ingestion of the gastrointestinal capsule;
 (e) a clock; and
 (f) a controller adapted preset with at least one predetermined time of day and functionally associated with the at least one sensor and with the clock, the controller adapted, in response to receipt of input from the at least one sensor indication ingestion of the gastrointestinal capsule, using the clock, to track time to occurrence of the at least one predetermined time of day and to activate the vibrating agitator to operate in the first vibrating mode of operation at the at least one predetermined time of day.

In some embodiments, the at least one predetermined time of day is a default time of day. In some embodiments the at least one predetermined time of day is a default mealtime.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments the clock is set to a default time zone. In some embodiments, the at least one predetermined time of day is set according to a typical circadian cycle of subjects in the default time zone.

In some embodiments the gastrointestinal capsule further includes a location sensor functionally associated with the controller, and the controller is further adapted, upon receipt of an input from the location sensor indicating a change in location, to activate the vibrating agitator to operate in the first vibrating mode of operation at the at least one predetermined time of day in accordance with a destination time zone.

In accordance with yet another embodiment of the present invention there is provided a system for treating a gastrointestinal tract of a subject, the system including:
 a gastrointestinal capsule including:
 (a) a housing;
 (b) a vibrating agitator adapted such that, in a first vibrating mode of operation, the housing exerts vibrations on an environment surrounding the capsule;
 (c) a power supply disposed within the housing and adapted to power the vibrating agitator;
 (d) a clock;
 (e) a first communication interface, such as a transceiver; and
 (f) a controller preset with at least one predetermined time of day and functionally associated with the clock and with the communication interface, the controller adapted, in response to receipt of an activation input, using the clock, to track time to occurrence of the at least one predetermined time of day and to activate the vibrating agitator to operate in the first vibrating mode of operation at the at least one predetermined time of day; and a control unit including a second communication interface, said control unit adapted to provide the activation input to the capsule.

In some embodiments, the control unit is adapted to provide the activation input prior to the subject ingesting the gastrointestinal capsule.

In some embodiments, the control unit further includes a sensor adapted to sense the presence of the gastrointestinal capsule in or on the control unit, and the control unit is adapted to provide the activation input in response to receipt of an input from the sensor indicating that the gastrointestinal capsule is in or on the control unit, for at least a predetermined duration.

In some embodiments, the control unit further includes a user interface, and is adapted to provide the activation input in response to receipt of a user input, via the user interface, the user input indicating that the subject will soon ingest the capsule.

In some embodiments, the control unit is devoid of a timing mechanism.

In some embodiments, the at least one predetermined time of day is a default time of day. In some embodiments the at least one predetermined time of day is a default mealtime.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments the clock is set to a default time zone. In some embodiments, the at least one predetermined time of day is set according to a typical circadian cycle of subjects in the default time zone.

In some embodiments the gastrointestinal capsule further includes a location sensor functionally associated with the controller, and the controller is further adapted, upon receipt of an input from the location sensor indicating a change in location, to activate the vibrating agitator to operate in the first vibrating mode of operation at the at least one predetermined time of day in accordance with a destination time zone.

In accordance with a further embodiment of the present invention there is provided a system for treating a gastrointestinal tract of a subject, the system including:

a gastrointestinal capsule including:
(a) a housing;
(b) a vibrating agitator adapted such that, in a first vibrating mode of operation, the housing exerts vibrations on an environment surrounding the capsule;
(c) a power supply disposed within the housing and adapted to power the vibrating agitator;
(d) a clock;
(e) a first communication interface, such as a transceiver; and
(f) a controller functionally associated with the clock and with the communication interface, the controller adapted, in response to receipt of an activation input including at least one predetermined time of day, using the clock, to track time to occurrence of the at least one predetermined time of day and to activate the vibrating agitator to operate in the first vibrating mode of operation at the at least one predetermined time of day; and a control unit including a second communication interface, said control unit adapted to provide the activation input including the at least one predetermined time of day to the capsule.

In some embodiments, the control unit is adapted to provide the activation input prior to the subject ingesting the gastrointestinal capsule.

In some embodiments, the control unit further includes a sensor adapted to sense the presence of the gastrointestinal capsule in or on the control unit, and the control unit is adapted to provide the activation input in response to receipt of an input from the sensor indicating that the gastrointestinal capsule is in or on the control unit, for at least a predetermined duration.

In some embodiments, the control unit further includes a user interface, and is adapted to provide the activation input in response to receipt of a user input, via the user interface, the user input indicating that the subject will soon ingest the capsule.

In some embodiments, the control unit is devoid of a timing mechanism.

In some embodiments, the at least one time of day is preset in the control unit. In some embodiments, the at least one predetermined time of day is a default time of day. In some embodiments the at least one predetermined time of day is a default mealtime.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments, the control unit is further adapted to compute the at least one time of day.

In some such embodiments, the control unit further includes a user interface, and is adapted to compute the at least one time of day based on a user input received via the user interface. In some embodiments the user input includes at least one of a sleep schedule and a meal schedule of the subject.

In some embodiments, the control unit further includes a location sensor, and is adapted to compute the at least one time of day based on a location of the control unit.

In some embodiments the gastrointestinal capsule further includes a location sensor functionally associated with the controller, and the controller is further adapted, upon receipt of an input from the location sensor indicating a change in location, to activate the vibrating agitator to operate in the first vibrating mode of operation at the at least one predetermined time of day in accordance with a destination time zone.

In accordance with a further embodiment of the present invention there is provided a system for treating a gastrointestinal tract of a subject, the system including:

a gastrointestinal capsule including:
(a) a housing;
(b) a vibrating agitator adapted such that, in a first vibrating mode of
operation, the housing exerts vibrations on an environment surrounding the
capsule;
(c) a power supply disposed within the housing and adapted to power the vibrating agitator;

(d) a timer;

(e) a first communication interface, such as a transceiver; and (f) a controller functionally associated with the timer and with the communication interface, the controller adapted, in response to receipt of an activation input including at least one time delay, using the timer, to track passage of time to completion of the time delay and to activate the vibrating agitator to operate in the first vibrating mode of operation; and a control unit including a clock and a second communication interface, said control unit adapted to:

compute a time delay from a current time to at least one predetermined time of day; and provide to the gastrointestinal capsule the activation input including the computed time delay, wherein the controller is adapted to activate the vibrating agitator to operate in the first vibrating mode of operation at the at least one predetermined time of day.

In some embodiments, the control unit is adapted to provide the activation input prior to the subject ingesting the gastrointestinal capsule.

In some embodiments, the control unit further includes a sensor adapted to sense the presence of the gastrointestinal capsule in or on the control unit, and the control unit is adapted to provide the activation input in response to receipt of an input from the sensor indicating that the gastrointestinal capsule is in or on the control unit, for at least a predetermined duration.

In some embodiments, the control unit further includes a user interface, and is adapted to provide the activation input in response to receipt of a user input, via the user interface, the user input indicating that the subject will soon ingest the capsule.

In some embodiments, the at least one time of day is preset in the control unit. In some embodiments, the at least one predetermined time of day is a default time of day. In some embodiments the at least one predetermined time of day is a default mealtime.

In some embodiments, the control unit is further adapted to compute the at least one time of day.

In some such embodiments, the control unit further includes a user interface, and is adapted to compute the at least one time of day based on a user input received via the user interface. In some embodiments the user input includes at least one of a sleep schedule and a meal schedule of the subject.

In some embodiments, the control unit further includes a location sensor, and is adapted to compute the at least one time of day based on a location of the control unit.

In accordance with a further embodiment of the present invention there is provided a system for treating a gastrointestinal tract of a subject, the system including:

a gastrointestinal capsule including:

(a) a housing;

(b) a vibrating agitator adapted such that, in a first vibrating mode of operation, the housing exerts vibrations on an environment surrounding the capsule;

(c) a power supply disposed within the housing and adapted to power the vibrating agitator;

(d) a first communication interface, such as a transceiver; and (e) a controller functionally associated with the communication interface, the controller adapted, in response to receipt of an activation input, to substantially immediately activate the vibrating agitator to operate in the first vibrating mode of operation; and a control unit including a clock and a second communication interface, said control unit adapted to provide to the gastrointestinal capsule the activation input at at least one predetermined time of day, following ingestion of the gastrointestinal capsule.

In some embodiments, the at least one time of day is preset in the control unit. In some embodiments, the at least one predetermined time of day is a default time of day. In some embodiments the at least one predetermined time of day is a default mealtime.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments, the control unit is further adapted to compute the at least one time of day.

In some such embodiments, the control unit further includes a user interface, and is adapted to compute the at least one time of day based on a user input received via the user interface. In some embodiments the user input includes at least one of a sleep schedule and a meal schedule of the subject.

In some embodiments, the control unit further includes a location sensor, and is adapted to compute the at least one time of day based on a location of the control unit.

In some embodiments, the gastrointestinal capsule is devoid of a timing mechanism.

In accordance with a further embodiment of the present invention there is provided a method of treating the gastrointestinal tract of a subject, the method including:

(a) providing the gastrointestinal capsule as described herein;

(b) ingesting the gastrointestinal capsule; and (c) controlling the vibrating agitator such that the first vibrating mode of operation occurs at the at least one predetermined time of day.

In accordance with another embodiment of the present invention there is provided a method of treating the gastrointestinal tract of a subject, the method including:

(a) providing a gastrointestinal capsule, adapted to transit a gastrointestinal tract of the subject, the capsule having:

(1) a housing arranged along a longitudinal axis;

(2) a vibrating agitator, adapted such that, in a first vibrating mode of operation, the housing exerts vibrations on an environment surrounding the capsule;

(3) a power supply disposed within the housing and adapted to power the vibrating agitator; and (4) a controller adapted, to activate the vibrating agitator to operate in the first vibrating mode of operation;

(b) receiving at least one capsule activation input;

(c) ingesting the gastrointestinal capsule; and (d) responsive to the capsule activation input, controlling the vibrating agitator such that the first vibrating mode of operation occurs at the at least one predetermined time of day.

In accordance with yet another embodiment of the present invention there is provided a method of treating the gastrointestinal tract of a subject, the method including:

(a) providing a gastrointestinal capsule, adapted to transit a gastrointestinal tract of the subject, the capsule having:

(1) a housing arranged along a longitudinal axis;
(2) a vibrating agitator, adapted such that, in a first vibrating mode of operation, the housing exerts vibrations on an environment surrounding the capsule;
(3) a power supply disposed within the housing and adapted to power the vibrating agitator; and
(4) a controller adapted, to activate the vibrating agitator to operate in the first vibrating mode of operation;

(b) ingesting the gastrointestinal capsule; and
(c) when the gastrointestinal capsule is in an operative state, controlling the vibrating agitator such that the first vibrating mode of operation occurs at the at least one predetermined time of day.

In some embodiments, the method is adapted for treating an ailment of the gastrointestinal tract of the subject.

In some embodiments, the subject is travelling from an origin location to a destination location, and the method is adapted for mitigating jetlag of the subject.

In some such embodiments, the first vibrating mode of operation occurs at the at least one predetermined time of day according to the time zone of the origin location.

In other such embodiments, the first vibrating mode of operation occurs at the at least one predetermined time of day according to the time zone of the destination location.

In yet other such embodiments, the first vibrating mode of operation occurs, at a first time of day of the at least one predetermined time of day according to the time zone of the origin location, and at a second time of day of the at least one predetermined time of day according to the time zone of the destination location.

In some embodiments, the predetermined time of day is selected according to a circadian cycle of the subject.

In some embodiments, the predetermined time of day is selected according to a gastric pH profile of the subject.

In some embodiments, providing a gastrointestinal capsule includes providing the gastrointestinal capsule in an inoperative state, the method further including, at the capsule, receiving an activation input transitioning the capsule from the inoperative state to the operative state.

In some embodiments, providing the gastrointestinal capsule includes providing the gastrointestinal capsule including at least one timing mechanism, and devoid of sensors for sensing an environment thereof. In some such embodiments the at least one timing mechanism comprises a clock. In other embodiments the at least one timing mechanism comprises a timer.

In some embodiments, the controlling includes, responsive to the activation input, waiting a predetermined delay time, and following the predetermined delay time, at a time coinciding with the at least one predetermined time of day, activating the vibrating agitator to operate in the first vibration mode of operation.

In some embodiments, receiving the at least one activation input includes receiving the at least one activation input from at least one sensor forming part of the gastrointestinal capsule.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor, and the receiving the at least one activation input includes receiving input indicating pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the capsule further including a timing mechanism, the method further including, in response to the receiving the activation input, activating operation of the timing mechanism to track a time of day so as to identify the at least one predetermined time of day for activation of the vibration agitator.

In some embodiments, receiving the activation input includes receiving the activation input from a control unit remote from the gastrointestinal capsule.

In some embodiments, receiving the activation input includes receiving the activation input following the ingesting. In other embodiments, receiving the activation input includes receiving the activation input prior to the ingesting.

In some embodiments, receiving the activation input includes receiving a current time of day, and the controlling the vibration agitator includes computing a delay time from the current time of day to the at least one predetermined time of day and activating the vibrating agitator to operate in the first vibration mode of operation following the delay time.

In some embodiments, the activation input indicates that a current time of day is the at least one predetermined time of day, and controlling the vibration agitator to operate in the first vibration mode of operation occurs immediately following the receiving of the activation input.

In some embodiments, receiving the activation input includes receiving an indication of a delay time from the current time to the at least one predetermined time of day and activating the vibrating agitator to operate in the first vibration mode of operation following the delay time. In some such embodiments the timing mechanism of the capsule comprises a timer.

In some embodiments, the current time of day is the current time of day in the origin location of the subject. In other embodiments, the current time of day is the current time of day in the destination location of the subject.

In some embodiments, the activation input includes the at least one predetermined time of day.

In some embodiments, the at least one predetermined time of day includes at least one default predetermined time of day. In some embodiments, the at least one predetermined time of day includes at least one time of day coinciding with at least one predetermined mealtime.

In some embodiments, the at least one predetermined mealtime is a predetermined mealtime in the time zone of the origin location of the subject. In other embodiments, the at least one predetermined mealtime is a predetermined mealtime in the time zone of the destination location of the subject.

In some embodiments, the at least one predetermined mealtime includes at least one default mealtime.

In some embodiments, the at least one default mealtime includes a default breakfast time. In some embodiments, the default breakfast time is between 5 am and 10 am, between 6 am and 10 am, between 6 am and 9 am, between 6 am and 8 am, between 7 am and 10 am, between 7 am and 9 am, and between 7 am and 8 am.

In some embodiments, the at least one default mealtime includes a default lunchtime. In some embodiments, the default lunchtime is between 12 pm and 3 pm, between 12 pm and 2 pm, or between 1 pm and 3 pm.

In some embodiments, the at least one default mealtime includes a default suppertime. In some embodiments, the default suppertime is between 6 pm and 10 pm, between 7 pm and 10 pm, between Bpm and 10 pm, between 6 pm and 9 pm, between 7 pm and 9 pm, or between 6 pm and 8 pm.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments, activation of the vibrating agitator to operate in the first vibrating mode of operation at the at least one predetermined time of day triggers a spontaneous bowel movement (SBM) in the user, which SBM occurs at a later time of day than the at least one predetermined time of day.

In some embodiments, activation of the vibrating agitator to operate in the first vibrating mode of operation at the at least one predetermined time of day triggers a complete spontaneous bowel movement (CSBM) in the user, which CSBM occurs at a later time of day than the at least one predetermined time of day.

In some such embodiments, the at least one predetermined time of day is lunchtime, for example between 12 pm to 3 pm or between 12 pm to 2 pm, and the later time of day is dinnertime, for example between 6 pm and 9 pm.

In some embodiments, the method further includes, prior to the controlling, receiving subject-specific input relating to at least one subject-specific mealtime of the subject, and wherein the at least one predetermined mealtime includes the at least one subject-specific mealtime.

In some embodiments, the at least one subject-specific mealtime is a subject-specific mealtime in the time zone of the origin location of the subject. In other embodiments, the at least subject-specific mealtime is a subject-specific mealtime in the time zone of the destination location of the subject.

In some embodiments, the method further includes, prior to the controlling, receiving regional information relating to a geographical region in which the gastrointestinal capsule is located, and wherein the at least one predetermined time of day includes at least one region-specific time of day of the geographical region. In some embodiments, the at least one region-specific time of day comprises a region-specific mealtime of the geographical region.

In some embodiments, the geographical region is a geographical region of the origin location of the subject. In other embodiments, the geographical region is a geographical region of the destination location of the subject.

In some embodiments, receiving the regional information includes receiving an identification of the geographical region. In some embodiments, the identification of the geographical region is received from a location sensor. In some embodiments, receiving the regional information includes receiving the at least one region-specific time of day of the geographical region. In some embodiments, receiving the regional information includes receiving the at least one region-specific mealtime of the geographical region.

In some embodiments, receiving regional information occurs in a control unit remote from the gastrointestinal capsule prior to the gastrointestinal capsule receiving the activation input, and wherein the receiving the activation input includes receiving activation input being on the received regional information.

In some embodiments, receiving regional information is carried out by the controller of the gastrointestinal capsule.

In some embodiments, receiving the activation input additionally includes receiving a vibration protocol to be used by the controller to control operation of the vibrating agitator.

In some embodiments, the vibrating agitator includes at least a radial agitator, and the controlling includes controlling the radial agitator, in the first vibrating mode of operation, to exert radial forces on the housing, in a radial direction with respect to the longitudinal axis of the housing, thereby to cause the vibrations exerted by the housing.

In some embodiments, the vibrating agitator includes at least an axial agitator, and the controlling includes controlling the axial agitator, in the first vibrating mode of operation, to exert axial forces on the housing, in an axial direction with respect to the longitudinal axis of the housing, thereby to cause the vibrations exerted by the housing.

In some embodiments, the controlling includes controlling the vibrating agitator, in the first vibrating mode of operation, to exert radial forces on the housing in a radial direction with respect to the longitudinal axis of the housing and to exert axial forces on the housing in an axial direction with respect to the longitudinal axis of the housing, thereby to cause the vibrations exerted by the housing.

In some embodiments, the vibrating agitator includes a radial agitator adapted to exert the radial forces and a separate axial agitator adapted to exert the axial forces.

In some embodiments, the vibrating agitator includes a single agitator adapted to exert the radial forces and the axial forces.

In some embodiments, the housing includes first and second members, and controlling the vibrating agitator includes effecting a vibration by moving the first member of the housing in the opposite direction relative to the second member of the housing.

In some embodiments, controlling the vibrating agitator includes controlling the vibrating mode of operation to include a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, controlling the vibrating agitator includes controlling the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours. In some embodiments, the cumulative duration is dependent on properties of the battery.

In some embodiments, in the first vibration mode of operation, the vibrating agitator is configured such that a net force exerted by the housing on the environment is in the range of 50 grams-force to 600 grams-force.

In some embodiments, in the first vibration mode of operation the vibrating agitator is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, controlling of the vibrating agitator includes controlling the vibrating agitator so as to effect a mechanical stimulation of the wall of the gastrointestinal tract during the at least one predetermined time of day.

In accordance with another embodiment of the present invention, there is provided a method of treating the gastrointestinal tract of a subject, the method including ingesting, by the subject, a gastrointestinal capsule including:
a housing;
a vibrating agitator adapted such that, in a first vibrating mode of operation, the housing exerts vibrations on an environment surrounding the gastrointestinal capsule;
a power supply disposed within the housing, and adapted to power the vibrating agitator;
at least one sensor adapted to identify ingestion of the gastrointestinal capsule;
a clock; and
a controller preset with at least one predetermined time of day and functionally associated with the at least one sensor and with the clock, the controller adapted, in response to receipt of input from the at least one sensor indicating ingestion of the gastrointestinal capsule, to activate the vibrating agitator to operate in the first vibrating mode of operation at the at least one predetermined time of day.

In accordance with yet another embodiment of the present invention, there is provided a method of treating the gastrointestinal tract of a subject, the method including:
providing to the subject, or the subject obtaining, a gastrointestinal capsule including:
(a) a housing;
(b) a vibrating agitator adapted such that, in a first vibrating mode of operation, the housing exerts vibrations on an environment surrounding the capsule;
(c) a power supply disposed within the housing and adapted to power the vibrating agitator;
(d) a clock;
(e) a first communication interface, such as a transceiver; and
(f) a controller preset with at least one predetermined time of day and functionally associated with the clock and with the communication interface, the controller adapted, in response to receipt of an activation input, using the clock, to track time to occurrence of the at least one predetermined time of day and to activate the vibrating agitator to operate in the first vibrating mode of operation at the at least one predetermined time of day;
triggering, by the subject, a control unit to provide the activation input to the controller; and
ingesting, by the subject, of the gastrointestinal capsule, such that the controller activates the vibrating agitator to operate in the first vibrating mode of operation at the at least one predetermined time of day following receipt of the activation input.

In some embodiments, the triggering comprises placing the gastrointestinal capsule in or on the control unit for at least a predetermined duration.

In some embodiments, the triggering comprises providing a user input, to the control unit, via a user interface. In some such embodiments the user input is indicative of the subject being ready to ingest the capsule.

In accordance with a further embodiment of the present invention, there is provided a method of treating the gastrointestinal tract of a subject, the method including:
providing to the subject, or the subject obtaining, a gastrointestinal capsule including:
(a) a housing;
(b) a vibrating agitator adapted such that, in a first vibrating mode of operation, the housing exerts vibrations on an environment surrounding the capsule;
(c) a power supply disposed within the housing and adapted to power the vibrating agitator;
(d) a clock;
(e) a first communication interface, such as a transceiver; and
(f) a controller functionally associated with the clock and with the communication interface, the controller adapted, in response to receipt of an activation input including at least one predetermined time of day, using the clock, to track time to occurrence of the at least one predetermined time of day and to activate the vibrating agitator to operate in the first vibrating mode of operation at the at least one predetermined time of day;
triggering, by the subject, a control unit to provide the activation input including the at least one predetermined time of day to the controller; and
ingesting, by the subject, of the gastrointestinal capsule, such that the controller activates the vibrating agitator to operate in the first vibrating mode of operation at the at least one predetermined time of day following receipt of the activation input.

In some embodiments, the triggering comprises placing the gastrointestinal capsule in or on the control unit for at least a predetermined duration.

In some embodiments, the triggering comprises providing a user input, to the control unit, via a user interface. In some such embodiments the user input is indicative of the subject being ready to ingest the capsule.

In some embodiments, the activation input further includes a vibration protocol, such that the controller activates the vibrating agitator to operate in the first vibrating mode of operation in accordance with the vibrating protocol.

In some embodiments, the at least one time of day is preset in the control unit. In some such embodiments the at least one time of day is a default time of day.

In some embodiments, the at least one time of day is provided to the control unit as part of a treatment protocol.

In some embodiments, the method further includes, at the control unit, computing the at least one predetermined time of day, prior to providing the activation input.

In some embodiments, the method further includes, at the control unit, receiving user input, and computing the at least one predetermined time of day based on the received user input.

In accordance with another embodiment of the present invention, there is provided a method of treating the gastrointestinal tract of a subject, the method including:

providing to the subject, or the subject obtaining, a gastrointestinal capsule including:
  (a) a housing;
  (b) a vibrating agitator adapted such that, in a first vibrating mode of operation, the housing exerts vibrations on an environment surrounding the capsule;
  (c) a power supply disposed within the housing and adapted to power the vibrating agitator;
  (d) a timer;
  (e) a first communication interface, such as a transceiver; and
  (f) a controller functionally associated with the timer and with the communication interface, the controller adapted, in response to receipt of an activation input providing at least one time delay, using the timer, to track passage of time to completion of the at least one time delay and to activate the vibrating agitator to operate in the first vibrating mode of operation;

triggering, by the subject, a control unit to provide the activation input including the at least one time delay to the controller; and ingesting, by the subject, of the gastrointestinal capsule, such that the controller activates the vibrating agitator to operate in the first vibrating mode of operation following the at least one time delay, at a time coincidental with at least one predetermined time of day.

In some embodiments, the triggering comprises placing the gastrointestinal capsule in or on the control unit for at least a predetermined duration.

In some embodiments, the triggering comprises providing a user input, to the control unit, via a user interface. In some such embodiments the user input is indicative of the subject being ready to ingest the capsule.

In some embodiments, the activation input further includes a vibration protocol, such that the controller activates the vibrating agitator to operate in the first vibrating mode of operation in accordance with the vibrating protocol.

In some embodiments, the method further includes, at the control unit, computing the at least one time delay from the current time to the at least one predetermined time of day.

In some embodiments, the at least one time of day is preset in the control unit. In some such embodiments the at least one time of day is a default time of day.

In some embodiments, the at least one time of day is provided to the control unit as part of a treatment protocol.

In some embodiments, the method further includes, at the control unit, computing the at least one predetermined time of day, prior to providing the activation input.

In some embodiments, the method further includes, at the control unit, receiving user input, and computing the at least one predetermined time of day based on the received user input.

In accordance with yet another embodiment of the present invention there is provided a method of treating the gastrointestinal tract of a subject, the method including:

providing to the subject, or the subject obtaining, a gastrointestinal capsule including:
  (a) a housing;
  (b) a vibrating agitator adapted such that, in a first vibrating mode of operation, the housing exerts vibrations on an environment surrounding the capsule;
  (c) a power supply disposed within the housing and adapted to power the vibrating agitator;
  (d) a first communication interface, such as a transceiver; and
  (e) a controller functionally associated with the communication interface, the controller adapted, in response to receipt of an activation input, to substantially immediately activate the vibrating agitator to operate in the first vibrating mode of operation;

ingesting, by the subject, of the gastrointestinal capsule, following the ingesting, at at least one predetermined time of day, automatically providing an activation input from a control unit to the gastrointestinal capsule, thereby causing the controller to control vibrating agitator to operate in the first vibrating mode of operation at the at least one predetermined time of day.

In some embodiments, the activation input further includes a vibration protocol, such that the controller activates the vibrating agitator to operate in the first vibrating mode of operation in accordance with the vibrating protocol.

In some embodiments, the at least one time of day is preset in the control unit. In some such embodiments the at least one time of day is a default time of day.

In some embodiments, the at least one time of day is provided to the control unit as part of a treatment protocol.

In some embodiments, the method further includes, at the control unit, computing the at least one predetermined time of day, prior to providing the activation input.

In some embodiments, the method further includes, at the control unit, receiving user input, and computing the at least one predetermined time of day based on the received user input.

There is further provided in accordance with an embodiment of the present invention a gastrointestinal treatment system including a gastrointestinal capsule for vibrating in a gastrointestinal tract of a subject following ingestion of the gastrointestinal capsule, the gastrointestinal capsule including:
(a) a housing having a longitudinal axis;
(b) a vibrating agitator adapted such that, in a first vibrating mode of operation, the housing exerts vibrations on an environment surrounding the capsule;
(c) a power supply disposed within the housing and adapted to power the vibrating agitator; and
(d) a controller adapted, in response to receipt of an activation input, to activate the vibrating agitator to operate in the first vibrating mode of operation at at least two predetermined times of day.

In some embodiments, the at least two predetermined times of day are selected according to a circadian cycle of the subject.

In some embodiments, one of the at least two predetermined times of day is a lunchtime. In some embodiments, the lunchtime is a default lunchtime. In some embodiments, the lunchtime is a subject-specific lunchtime. In some embodiments, the lunchtime is a region-specific lunchtime.

In some embodiments, one of the at least two predetermined times of day is a suppertime. In some embodiments, the suppertime is a default suppertime. In some embodiments, the suppertime is a subject-specific suppertime. In some embodiments, the suppertime is a region-specific suppertime.

There is additionally provided in accordance with an embodiment of the present invention a method of treating constipation of a subject, the method including:

(a) providing to the subject a gastrointestinal capsule for ingestion thereof, the gastrointestinal capsule being adapted to transit a gastrointestinal tract of the subject, the gastrointestinal capsule having:
  (1) a housing arranged along a longitudinal axis;
  (2) a vibrating agitator, the vibrating agitation mechanism adapted such that, in a first vibrating mode of operation, the housing exerts vibrations on an environment surrounding the gastrointestinal capsule;
  (3) a power supply disposed within the housing and adapted to power the vibrating agitator; and
  (4) a controller adapted to activate the vibrating agitator to operate in the first vibrating mode of operation;
(b) following ingestion of the gastrointestinal capsule by the subject, and when the gastrointestinal capsule is in an operative state, activating the vibrating agitator to operate in the first vibrating mode of operation at at least two predetermined times of day; and
(c) repeating steps (a) and (b), which together form a treatment session, one to seven times per week, thereby to treat constipation of the subject.

In some embodiments, the method further includes receiving input relating a circadian cycle of the subject, and the at least two predetermined times of day are selected according to the circadian cycle of the subject.

In some embodiments, one of the at least two predetermined times of day is a lunchtime. In some embodiments, the lunchtime is a default lunchtime. In some embodiments, the lunchtime is a subject-specific lunchtime. In some embodiments, the lunchtime is a region-specific lunchtime.

In some embodiments, one of the at least two predetermined times of day is a suppertime. In some embodiments, the suppertime is a default suppertime. In some embodiments, the suppertime is a subject-specific suppertime. In some embodiments, the suppertime is a region-specific suppertime.

There is also provided in accordance with an embodiment of the present invention a method of increasing a number of spontaneous bowel movements (SBMs) or of complete spontaneous bowel movements (CSBMs) that a subject experiences per week, the method including:

(a) obtaining a baseline number of SBMs or of CSBMs that the subject has per week;
(b) providing to the subject a gastrointestinal capsule for ingestion thereof, the gastrointestinal capsule being adapted to transit a gastrointestinal tract of the subject, the gastrointestinal capsule having:
  (1) a housing arranged along a longitudinal axis;
  (2) a vibrating agitator, the vibrating agitation mechanism adapted such that, in a first vibrating mode of operation, the housing exerts vibrations on an environment surrounding the gastrointestinal capsule;
  (3) a power supply disposed within the housing and adapted to power the vibrating agitator; and
  (4) a controller adapted to activate the vibrating agitator to operate in the first vibrating mode of operation;
(c) following ingestion of the gastrointestinal capsule by the subject, and when the gastrointestinal capsule is in an operative state, activating the vibrating agitator to operate in the first vibrating mode of operation at at least two predetermined times of day on at least two consecutive days, wherein the at least two predetermined times of day include at least two predetermined mealtimes; and
(d) repeating steps b and c, which together form a treatment session, one to seven times per week, for a period of at least two weeks.

In some embodiments, the repeating of steps b and c increases the number of SBMs or CSBMs experienced by the user, per week, by at least one additional SBM or one additional CSBM for at least two of the four weeks.

In some embodiments, the method further includes receiving input relating a circadian cycle of the subject, and the at least two predetermined times of day are selected according to the circadian cycle of the subject.

In some embodiments, one of the at least two predetermined times of day is a lunchtime. In some embodiments, the lunchtime is a default lunchtime. In some embodiments, the lunchtime is a subject-specific lunchtime. In some embodiments, the lunchtime is a region-specific lunchtime.

In some embodiments, one of the at least two predetermined times of day is a suppertime. In some embodiments, the suppertime is a default suppertime. In some embodiments, the suppertime is a subject-specific suppertime. In some embodiments, the suppertime is a region-specific suppertime.

In some embodiments, the activating of the vibrating agitator includes activating the vibrating agitator to operate in the first vibrating mode of operation for a predetermined duration at each time of activation thereof.

In some embodiments, the repeating steps b and c five times per week, for a period of at least two weeks, increases the number of SBMs or CSBMs experienced by the user, per week, by at least one additional SBM or one additional CSBM.

In some embodiments, the repeating steps b and c five times per week, for a period of at least two weeks, increases the number of SBMs or CSBMs experienced by the user, per week, by at least two additional SBMs or two additional CSBMs.

In some embodiments, the increasing of the number of SBMs or CSBMs experienced by the user per week includes improving a clinical definition criteria or clinical diagnosis of the subject.

There is further provided in accordance with an embodiment of the present invention a method of treating a gastrointestinal ailment of a subject, the method including:

(a) providing to the subject a gastrointestinal capsule for ingestion thereof, the gastrointestinal capsule being adapted to transit a gastrointestinal tract of the subject, the gastrointestinal capsule having:
  (1) a housing arranged along a longitudinal axis;
  (2) a vibrating agitator, the vibrating agitation mechanism adapted such that, in a first vibrating mode of operation, the housing exerts vibrations on an environment surrounding the gastrointestinal capsule;
  (3) a power supply disposed within the housing and adapted to power the vibrating agitator; and
  (4) a controller adapted to activate the vibrating agitator to operate in the first vibrating mode of operation;
(b) following ingestion of the gastrointestinal capsule by the subject, and when the gastrointestinal capsule is in an operative state, activating the vibrating agitator to operate in the first vibrating mode of operation at at least one predetermined time of day on at least two consecutive days; and
(c) repeating steps a and b, which together form a treatment session, one to seven times per week, thereby to treat at least one gastrointestinal ailment of the subject, wherein treating of the gastrointestinal ailment includes at least one of treating or alleviating constipation of the subject, reducing straining experienced by the subject during defecating, and increasing a Bristol stool score of stool of the subject.

In some embodiments, the method further includes receiving input relating a circadian cycle of the subject, and the at least one predetermined time of day is selected according to the circadian cycle of the subject.

In some embodiments, the at least one predetermined times of day is a lunchtime. In some embodiments, the lunchtime is a default lunchtime. In some embodiments, the lunchtime is a subject-specific lunchtime. In some embodiments, the lunchtime is a region-specific lunchtime.

In some embodiments, the at least one predetermined time of day is a suppertime. In some embodiments, the suppertime is a default suppertime. In some embodiments, the suppertime is a subject-specific suppertime. In some embodiments, the suppertime is a region-specific suppertime.

In some embodiments, the activating of the vibrating agitator includes activating the vibrating agitator to operate in the first vibrating mode of operation for a predetermined duration at each activation thereof.

In some embodiments, the repeating the steps (a) and (b) one to seven times per week includes repeating steps (a) and (b) at least twice per week on consecutive days, such that first and second the gastrointestinal capsules disposed in two different locations within the gastrointestinal tract of the subject simultaneously, and the activating the vibrating agitator to operate in the first vibrating mode of operation at the at least one predetermined time of day on two consecutive days includes activating the vibrating agitators of the first and second gastrointestinal capsules to operate in the first vibrating mode of operation, simultaneously at the two different locations, during the at least one predetermined time of day.

In some embodiments, the method further includes prior to (a), obtaining a baseline number of spontaneous bowel movements (SBM) or of complete spontaneous bowel movements (CSBM) that the subject has per week.

In some embodiments, the method further includes repeating steps a-d for at least two weeks, thereby to increase a number of SBMs or CSBMs of the subject by at least one additional SBM or at least one additional CSBM over the baseline number.

In some embodiments, the method further includes repeating steps a-d for at least two weeks, thereby to increase a number of SBMs or CSBMs of the subject by at least two additional SBMs or at least one additional CSBMs over the baseline number.

BRIEF DESCRIPTION OF THE FIGURES

The foregoing discussion will be understood more readily from the following detailed description of the invention, when taken in conjunction with the accompanying FIGS. 1A-5B), in which:

FIGS. 1A to 1F are schematic block diagram of various embodiments of gastrointestinal treatment systems including a vibrating ingestible capsule according to the present invention;

FIGS. 2A to 2F are schematic flowcharts of embodiments of methods for treating the gastrointestinal tract according to the present invention, the treatment methods being based on use of the gastrointestinal treatment systems of FIGS. 1A to 1F, respectively;

FIG. 4 is a graphic illustration of the gastric pH of a person, indicating suitable times of day for the implementation of the methods of FIGS. 2A to 2F;

FIGS. 5A and 5B are graphic representation of results of clinical experiments conducted using an ingestible vibrating gastrointestinal capsule as illustrated in FIG. 1A and using a method as illustrated in FIG. 2A.

DESCRIPTION OF THE PREFERRED EMBODIMENTS

Figure 1A:
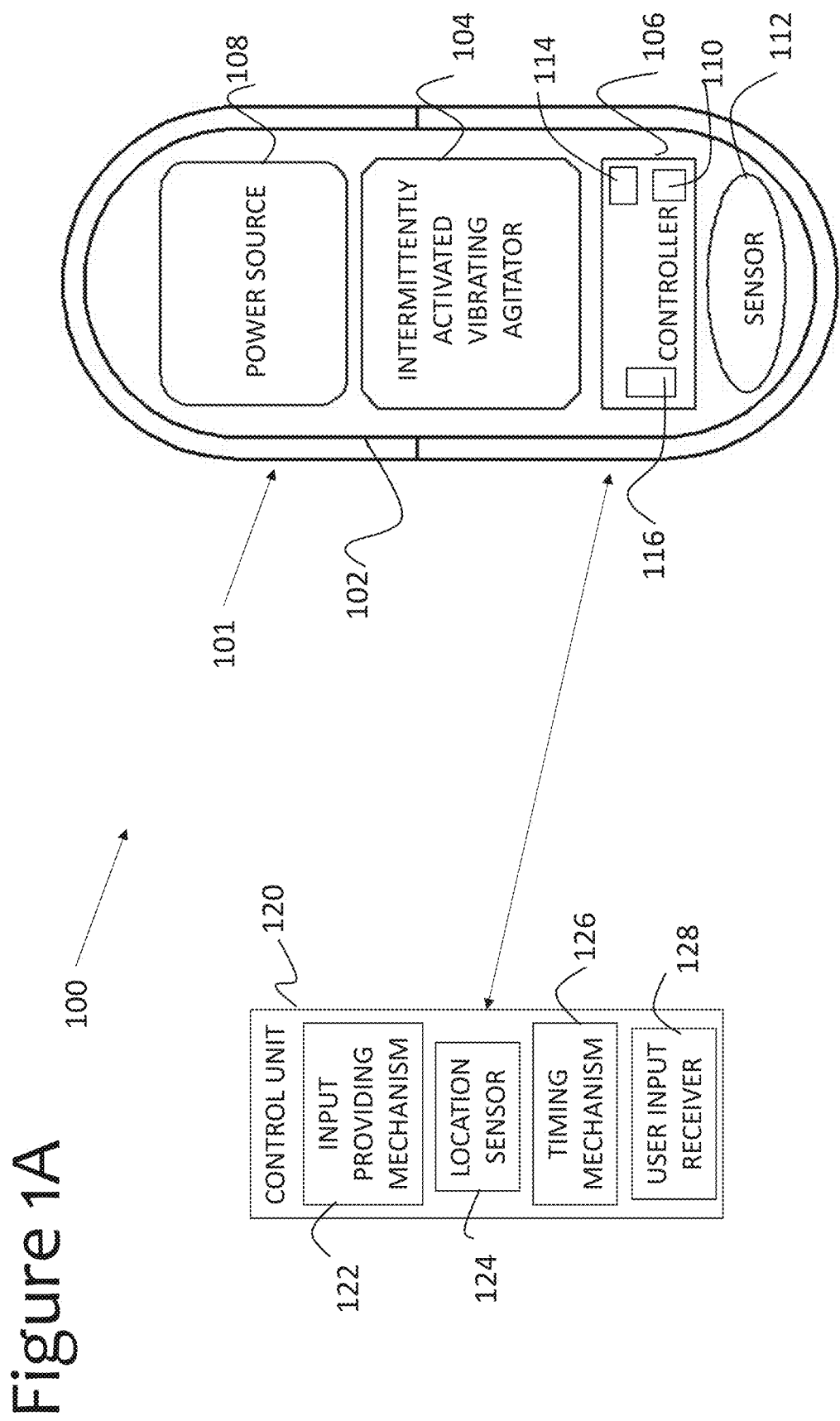

The principles of the inventive gastrointestinal treatment system and method of treating the gastrointestinal tract using the inventive gastrointestinal treatment system, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "subject" relates to a human.

For the purposes of this application, the term "vibrating ingestible capsule" relates to an ingestible capsule adapted to at least intermittently vibrate, for a cumulative duration of at least one minute, in accordance with a vibration protocol of the capsule.

For the purposes of this application, the term "vibrating agitator" refers to any type of structure or mechanism that vibrates or causes elements in its vicinity to vibrate, including a motor driven agitator such as a motor driven rotor including an eccentric weight, a motor drive pendulum, and a motor driven axial agitator.

For the purposes of this application, the term "intermittently activated vibrating agitator" refers to a vibrating agitator that vibrates or causes elements in its vicinity to vibrate and is operative at certain times, and does not vibrate or cause elements in its vicinity to vibrate at other times, the activation times being selected by a controller or other control unit controlling the vibrating agitator.

For the purposes of this application, the term "controller", and the equivalent term "control element" refer to a computing circuit or element for controlling operation of mechanical and/or electrical components of the capsule, which form part of the capsule. The controller includes a processor or processing unit functionally associated with a non-tangible computer readable storage medium. The storage medium stores instructions, which, when executed by the processor, carry out actions which control the operation of the mechanical and/or electrical components of the capsule. For example, the instructions may include instructions to activate operation of a vibrating agitator at a specific time, frequency, cycle, and/or for a specific duration. The controller may be functionally associated with, or may include, a transceiver for receiving input, which input may be used to trigger execution of specific instructions stored in the storage medium.

For the purposes of this application, the term "control unit" refers to a computing circuit or device for controlling operation of mechanical and/or electrical components of the capsule, which is remote from the capsule. The control unit includes a processor or processing unit functionally associated with a non-tangible computer readable storage medium. The storage medium stores instructions, which, when executed by the processor, carry out actions which control the operation of the capsule or provide instructions to the controller of the capsule. For example, the instructions may include instructions to provide to the capsule a specific vibration protocol or to receive feedback from the capsule. The control unit is functionally associated with, or includes, a transceiver for communication with the capsule.

For the purposes of this application, the term "clock" relates to a mechanism capable of tracking time, in a manner that is indicative of a time of day, for example as a specific hour, minute, and/or second combination. The time of day may be relative to a specific time zone, such as Eastern Standard Time (EST) or Greenwich Mean Time (GMT). A clock may be capable of tracking a time of day relative to a time preset, by default, by a processor or controller outside of the clock, or by a user, similar to a wrist watch or wall clock set to the time of day.

For the purposes of this application, the term "timer" relates to a mechanism capable of tracking passage of time relative to a beginning time, and which is not necessarily capable of tracking time in a manner that is indicative of a time of day. If the beginning time is indicative of a time of day, the timer is a clock. In a simple timer, the beginning time is not indicative of a time of day.

For the purposes of this application, the term "simple timer" relates to a timer, which is not a clock, and is only capable of tracking passage of time in a manner which is not indicative of the time of day. In a simple timer, passage of a specific time duration, such as an hour, will always be indicated in an identical manner, regardless of differences in the beginning times. For example, a simple timer tracking an hour from 1:14:57 am or tracking an hour from 12:00:00 pm would indicate the same passage of time—1:00:00-one hour, zero minutes, zero seconds.

Thus, every clock is a timer, but not every timer is a clock. Specifically, a simple timer is not a clock.

For the purposes of this application, the term "predetermined time of day" relates to any time of day occurring within a specific predetermined duration. For example, the predetermined time of day 12:00 pm to 2:00 pm encompasses any minute or second within the two hours between 12:00 pm and 2:00 pm. Typically, the predetermined time of day is relative to a specific time zone (e.g., the local time zone where the capsule is disposed, obtained, programmed, or ingested). As such, the predetermined time of day 12:00 pm to 2:00 pm EST is different from the predetermined time of day 12:00 pm to 2:00 pm GMT. The predetermined time of day must be predetermined prior to its occurrence, but may be determined only shortly before its occurrence. Specifically, the predetermined time of day need not necessarily be a default time of day or included in factory settings, and may be computed by a controller or control unit, prior to its arrival.

For the purposes of this application, the term "within", with respect to a predetermined duration, refers to a period including the predetermined duration, as well a default "grace period" of up to 45 minutes before and after the predetermined duration.

In some embodiments the grace period is 10, 15, 20, or 30 before and after the predetermined duration.

For the purposes of this application, a vibrating agitator is considered "to operate" at a predetermined duration if it is operative at any point in time within that predetermined duration.

For the purposes of this application, the term "vibration protocol" relates to a protocol specifying vibration parameters of an intermittently activated vibrating agitator of a vibrating ingestible capsule. Typically, the vibration protocol relates to at least one of an activation time (for a first activation of the vibrating agitator) of day and an activation delay for initiating vibration (a duration between activation of the capsule and the first activation of the vibrating agitator), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g. 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject.

For the purpose of this application, the term "activation input" relates to an input received by a controller of a vibrating ingestible capsule, which causes the controller of the capsule to activate itself, so as to be able to process inputs and/or to control additional components of the capsule. The activation input may be received from an element forming part of the capsule, such as a sensor sensing specific conditions in which the capsule should be activated, or from a remote source, such as a remote control unit, for example by way of a signal transmitted to the capsule, magnetic field applied to the capsule, specific motion applied to the capsule, or any other type of input provided to the capsule from a remote source.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a controller controlling vibration of the capsule is inactive.

For the purpose of this application, a vibrating ingestible capsule is said to be in an "operative state" when the controller of the capsule is processing inputs and data, and can cause a vibrating agitator of the capsule to vibrate.

For the purpose of this application, the term "jetlag" relates to any symptom resulting from a change in time zones, including, but not limited to, a shift in a person's sleep schedule, acute constipation resulting from travel, and the like.

For the purpose of this application, the term "mitigating jetlag" relates to appreciably decreasing any jetlag symptom, for example by at least 25%. For example, for a traveler who typically suffers from acute constipation for the first 48 hours of travel, jetlag would be mitigated if the traveler suffered from such acute constipation for, at most, the first 36 hours of travel.

For the purposes of this application, the term "chronic constipation" relates to a spontaneous bowel movement (SBM) frequency of at most 3 SBMs per week, For the purposes of this application, the term "acute constipation" relates to a subject suffering from a specific event of constipation, without necessarily suffering from chronic constipation. For example, the subject may be constipated for several days following travel, or during travel, for example as part of the subject's jetlag symptoms.

Referring now to the drawings, FIGS. 1A to 1F are schematic block diagrams of various embodiments of gastrointestinal treatment systems including vibrating ingestible capsules according to embodiments of the present invention.

As seen in FIG. 1A, a general gastrointestinal treatment system 100 includes vibrating ingestible capsule 101. Capsule 101 includes a capsule housing or shell 102, arranged along a longitudinal axis and having disposed therein a vibrating agitator 104. A controller 106, which may for example be, or include, a processor, is adapted to control operation of the vibrating agitator 104, and at least one power source 108 provides power to vibrating agitator 104 and controller 106.

Power source 108 may be any suitable power source, such as one or more alkaline or silver oxide batteries, primary batteries, rechargeable batteries, capacitors and/or supercapacitors.

Intermittently activated vibrating agitator 104 is adapted to have a vibration mode of operation (also termed the first mode of operation) and a rest mode of operation (also termed the second mode of operation). In the vibration mode of operation, intermittently activated vibrating agitator 104 is adapted to exert forces on capsule housing 102, such that capsule housing 102 exerts vibrations on an environment surrounding capsule 101.

It is a particular feature of the present invention that controller 106 is adapted, in response to receipt of an activation input or when the capsule is in an operative state, to activate vibrating agitator 104 to operate in the vibrating mode of operation at at least one predetermined time of day, as described in detail hereinbelow with respect to FIGS. 2A to 2F.

In some embodiments, controller 106 is adapted to activate vibrating agitator 104 to operate in the vibrating mode of operation at the at least one predetermined time of day, on at least two consecutive days. For example, if controller 106 is adapted to activate vibrating agitator 104 to operate in the vibrating mode of operation at 1:00 pm, and the capsule is ingested by the subject at 6:00 pm on Sunday, controller 106 will activate vibrating agitator 104 at 1:00 pm on Monday, and again at 1:00 pm on Tuesday. In such embodiments, each activation of the vibrating agitator may be for a predetermined duration, e.g. 2 hours. In such embodiments, power source 108 carries sufficient charge for activation of the vibrating agitator on at least two consecutive days.

In some embodiments, the capsule is in an inoperative state, until the receipt of an activation input, which causes controller 106 to transition the capsule from the inoperative state to an operative state.

In some embodiments, controller 106 is functionally associated with, or includes, a timing mechanism 110, powered by power source 108 and adapted to track at least one time characteristic. In some embodiments, the timing mechanism 110 comprises a clock. In some embodiments, the timing mechanism 110 comprises a timer, for example adapted to track a duration that has passed since an activation input was received, or a duration that has passed since the subject ingested capsule 101.

In some embodiments, in response to receipt of an activation input, controller 106 is adapted to activate operation of a clock timing mechanism 110 to track a time of day, so as to identify the at least one predetermined time of day for activation of vibration agitator 104.

In some embodiments, capsule 101 is devoid of any sensors for sensing an environment thereof, and includes, as timing mechanism 110, a timer. In some such embodiments, controller 106 is adapted, in response to receipt of an activation input, to wait a predetermined delay time, or a delay time provided as part of the activation input, and following the delay time, at a time coinciding with the at least one predetermined time of day, to activate vibrating agitator 104 to operate in the first vibration mode of operation.

In other embodiments, such as the embodiment illustrated in FIG. 1, capsule 101 further includes at least one sensor 112, functionally associated with controller 106. The at least one sensor 112 may be adapted to sense at least one parameter within capsule 101 or in an environment of capsule 101, and may include a temperature sensor, an illumination sensor, a moisture sensor, a pressure sensor, an accelerometer, or any other suitable sensor. In some embodiments, the at least one sensor 112 is adapted to identify a specific condition in capsule 101 or in the vicinity thereof, and to provide an activation input to controller 106 in response to identification of the condition. For example, in some embodiments the condition is indicative of the subject ingesting capsule 101. For example, in some embodiments sensor 112 may include an illumination sensor, adapted to identify transition of capsule 101 from an illuminated environment (e.g. outside the human body) to a dark environment (e.g. within the human body) and to provide an activation input in response to identification of such a transition.

As another example, in some embodiments sensor 112 may include a pressure sensor adapted identify pressure applied to the capsule 101, which pressure is indicative of the capsule moving through a pharynx of the subject, and to provide an activation input in response to identification of such pressure.

As a further example, in some embodiments sensor 112 may include a temperature sensor adapted to identify transition of capsule 101 from an area with ambient temperature (e.g. outside the human body) to an area with a human body temperature and to provide an activation input in response to identification of such a transition.

As another example, in some embodiments, sensor 112 may include a motion or acceleration sensor, such as an accelerometer, adapted to identify an activation motion carried out by a user on capsule 101 and to provide an activation input in response to identification of such a transition. An example of an accelerometer providing an activation input for a gastrointestinal capsule is provided in U.S. patent application Ser. No. 15/168,065 filed on May 29, 2016 (and published as US 2017/0340242), which is incorporated by reference for all purposes as if fully set forth herein.

As a further example, in some embodiments sensor 112 may include a moisture sensor adapted to identify transition of capsule 101 from a dry area (e.g. outside the human body) to a moist area (e.g. within the human body) and to provide an activation input in response to identification of such a transition.

In some embodiments, such as the embodiment illustrated in FIG. 1A, capsule 101 further includes a location sensor 114, such as a GPS or GLONASS receiver, functionally associated with controller 106. Location sensor 114 may be adapted to identify the geographic location of the capsule.

In some embodiments, system 100 further includes a control unit 120, which is typically remote from capsule 101, and which is adapted to provide one or more inputs to the capsule. In some such embodiments, capsule 101 further includes a remote input receiving mechanism 116, such as a transceiver, functionally associated with controller 106, and adapted to receive inputs from an input providing mechanism 122 of control unit 120.

In some embodiments, control unit 120 may further include a location sensor 124, such as a GPS or GLONASS receiver, adapted to identify the geographic location of the control unit.

In some embodiments, control unit 120 may further include a timing mechanism 126, adapted to track at least one time characteristic, such as the time of day, or a duration that has passed since a control instruction was provided to capsule 101. Typically, the timing mechanism 126 comprises a clock.

In some embodiments, control unit 120 may further include a user input receiver 128, such as a keyboard, touch screen, or touch pad, adapted to receive input from a user, such as the subject, a medical professional treating the subject, or a caregiver of the subject.

Control unit 120 may be any suitable type of control unit. In some embodiments, control unit may be a suitably configured smart phone or a tablet computer.

In some such embodiments, control unit 120 may provide inputs to capsule 101 by remotely transmitting the inputs from input providing mechanism 122 to remote input receiving mechanism 116, for example using a short range wireless communication method, such as radio frequency (RF) communication or Bluetooth® communication. One example of such a mechanism for providing input to a capsule is described in U.S. patent application Ser. No. 15/132,039 filed Apr. 18, 2016 (and published as US2017/0296428), and entitled "IN VIVO DEVICE AND METHOD OF USING THE SAME", which is incorporated by reference for all purposes as if fully set forth herein.

In some embodiments, control unit 120 is adapted to provide the activation input to controller 106 of capsule 101. In some such embodiments, control unit 120 provides the activation input prior to the subject ingesting capsule 101, whereas in other embodiments control unit 120 provides the activation input following ingestion of capsule 101 by the subject.

As discussed hereinabove, controller 106 of capsule 101 is adapted to activate vibrating agitator 104 to operate in the vibrating mode of operation at at least one specific time of day. That specific time of day may be identified and/or provided to controller 106 by any of a number of methods or mechanism, some exemplary ones of which are described herein.

In some embodiments, controller 106 of capsule 101 is pre-programmed with the predetermined time of day, which may be, for example, a default time of day. In such embodiments, timing mechanism 110 of capsule 101 comprises a clock, adapted to identify the predetermined time of day.

In some embodiments, capsule 101 is adapted to be used to mitigate jetlag of a user travelling from an origin location having an origin time zone to a destination location having a destination time zone. In some such embodiments, the pre-determined time of day is a time of day in the origin time zone. In other such embodiments, the pre-determined time of day is a time of day in the destination time zone. In yet other embodiments, the predetermined time of day is a time of day in a home time zone, which is the time zone at which the subject normally resides, or has been residing for at least a predetermined duration, for example at least one week.

In some such embodiments, timing mechanism 110 provides controller 106 with the current time of day, such that, following receipt of the activation input, or once capsule 101 is in the operative state, controller 106 tracks the current time of day, for example in the origin time zone, the destination time zone, or the home time zone, until arrival of the predetermined time, and then activates vibrating agitator according to a suitable vibration protocol.

In some embodiments, the predetermined time of day is provided to controller 106 as part of the activation input, or in another input, for example provided by control unit 120.

In some embodiments, regardless of whether the predetermined time of day is pre-programmed or is provided to controller 106 as an input, the activation input (or another input) provided to controller 106, for example by control unit 120, includes the current time of day at the time of providing the activation input, for example in the origin time zone, the destination time zone, or the home time zone. In such embodiments, controller 106 and/or timing mechanism 110 is adapted to compute a delay time from the received current time of day (e.g. the time of the activation input) to the predetermined time of day, to wait the computed delay time and subsequently to activate vibrating agitator 104 according to a suitable vibration protocol.

In another embodiment, controller 106 may or may not be provided with the predetermined time of day. However, at the time of providing the activation input from control unit 120, using timing mechanism 126, control unit 120 computes a time delay between the current time and the predetermined time of day. Control unit 120 provides an activation input to controller 106, indicating the computed time delay that controller 106 should wait prior to activation of vibrating agitator 104, so that vibrating agitator 104 will operate in the vibrating mode of operation at the predetermined time of day. Using timing mechanism 110, controller 106 waits the computed time delay prior to activation of vibrating agitator, such that the first mode of operation of vibrating agitator 104 occurs at the predetermined time of day. In some such embodiments, timing mechanism 110 includes a timer.

In yet another embodiment, at the predetermined time of day, as indicated by timing mechanism 126, control unit 120 identifies that the current time of day is the predetermined time, and provides an activation input to controller 106 indicating that the vibrating agitator should be activated at this time. Controller 106 is adapted to activate vibrating agitator 104 to operate in the vibrating mode of operation immediately responsive to receipt of such an input. In some such embodiments, capsule 101 is devoid of a timing mechanism 110.

In some embodiments, the predetermined time of day is, or coincides with, at least one predetermined mealtime.

In some such embodiments, the predetermined mealtime is a default mealtime. For example, the default mealtime may be a default breakfast time, which may be between 5 am and 10 am, between 6 am and 10 am, between 6 am and 9 am, between 6 am and 8 am, between 7 am and 10 am, between 7 am and 9 am, and between 7 am and 8 am. As another example, the default mealtime may be a default lunch time, which may be between 12 pm and 3 pm, between 12 pm and 2 pm, or between 1 pm and 3 pm. As yet another example, the default meal time may be a default supper time, which may be between 6 pm and 10 pm, between 7 pm and 10 pm, between Bpm and 10 pm, between 6 pm and 9 pm, between 7 pm and 9 pm, or between 6 pm and 8 pm.

In some embodiments, the at least one predetermined time of day includes at least two predetermined times of day. In some embodiments, the at least two predetermined times of day include lunchtime. In some embodiments, the at least two predetermined times of day include suppertime. In some embodiments, the at least two predetermined times of day include at least two mealtimes. In some embodiments, the at least two mealtimes include lunchtime and suppertime.

In some embodiments, the vibrating agitator is activated at the at least two mealtimes on at least two consecutive days. For example, the vibrating agitator may be activated at lunchtime and suppertime on Monday, and then again at lunchtime and suppertime on Tuesday.

In some embodiments, the vibrating agitator may also be activated an additional time, at one of the predetermined mealtimes, on a third consecutive day. For example, the vibrating agitator may be activated at lunchtime and suppertime on Monday, again at lunchtime and suppertime on Tuesday, and again at lunchtime on Wednesday.

In some embodiments in which the vibrating agitator is activated more than once, each activation of the vibrating agitator to be in the vibrating mode of operation is for a predetermined duration. For example, each activation of the vibrating agitator in the vibrating mode of operation may be for a duration of 1 hour, 1.5 hours, 2 hours, 2.5 hours, or 3 hours.

In such embodiments, power source 108 has sufficient charge to enable activation of the vibrating agitator for the predetermined duration, multiple times. For example, power source 108 may have sufficient charge to enable activation of the vibrating agitator in the vibrating mode of operation for at least 3 times, at least 4 times, or at least 5 times, where each activation is for the predetermined duration.

In some such embodiments, providing the vibration at a specific mealtime triggers a spontaneous bowel movement (SBM) or a complete spontaneous bowel movement (CSBM) of the subject at a later time of day than the predetermined time of day. For example, when the vibration is provided at lunchtime, i.e. between 12 pm and 3 pm or between 12 pm and 2 pm, the SBM or CSBM may occur around dinnertime, for example between 6 pm and 9 pm.

In some embodiments, use of capsule 101, according to a treatment protocol, may increase the number of SBMs experienced by the subject, per week, by at least 1 or at least 2 SBMs.

In some embodiments, use of capsule 101, according to a treatment protocol, may increase the number of CSBMs experienced by the subject, per week, by at least 1 or at least 2 CSBMs.

In some embodiments, the predetermined time of day is a user-specific time of day, or a user-specific mealtime at which the subject typically eats his/her meals. In some such embodiments, user input receiver 128 of control unit 120 (or an input receiver forming part of capsule 101 (not shown)), is adapted to receive, from the user (e.g. the subject or a caregiver of the subject) information about the user-specific time of day or user-specific mealtime. Control unit 120 may then provide the user-specific time of day or the user-specific mealtime to controller 106, for example as part of an activation input or as a separate input, or may provide a suitable input or activation input based on the user-specific time of day or the user-specific mealtime. For example, if the subject is used to eating their meals at 11 am and 4 pm, these times may be provided as input to control unit 120, which may then communicate these predetermined times of day to controller 106 for activation of vibrating agitator 104 at these times, or otherwise ensures that controller 106 will activate the vibrating agitator at these times, for example by indicating a suitable delay time or providing an activation input at the user-specific time of day or the user-specific mealtime, as explained hereinabove. As another example, if the subject wishes for the capsule to vibrate at 4:00 am, the subject may provide this information as input to control unit 120, which may then communicate this predetermined time to controller 106 for activation of vibrating agitator 104 at this time.

In some embodiments, the predetermined time of day is suited to the geographic region in which the capsule, the control unit 120, or the subject, are located. For example, if the subject has ingested the capsule, and has changed time zones since ingesting the capsule (for example flew from New-York to Chicago), the predetermined time of day may be adjusted to correspond to the new time zone in which the user is located. In some embodiments, the predetermined time of day is a region-specific mealtime at which the people in a geographical region at which the subject (or capsule) is located typically eat their meals.

The times at which people typically have supper, or dinner, may vary greatly between different geographical regions. For example, in the U.S. typical supper times are between 5 pm and Bpm or between 6 pm and 8 pm, whereas in Argentina most people only eat their supper between 9 pm and 11 pm, or even as late as midnight. Thus, the geographical region in which the capsule (and the subject) is located, may be used to identify the typical mealtimes of the subject.

In some such embodiments, location sensor 114 of capsule 101 may identify the location of the capsule, and provide the location or a region of the location to controller 106. In other embodiments, location sensor 124 of control unit 120 may identify the location of the control unit, and may provide the location or a region of the location to controller 106 as part of the activation input or as part of another input. Controller 106 may then determine the predetermined time of day, or region-specific mealtime, at which the vibrating agitator 104 should be in the operative mode of operation, based on the region. For example, controller 106 may be preprogrammed with predetermined times of day for specific regions, and may select a suitable pre-programmed predetermined time of day based on the identified region. As another example, controller 106 may access a database (not shown) to find the region-specific time of day, or region-specific mealtimes, for the identified region.

In yet other embodiments, location sensor 124 of control unit 120 may identify the location of the control unit, and may obtain, based on the identified location, the region-specific predetermined time(s) of day or region-specific mealtime(s), for example by accessing a pre-programmed list or by accessing a database (not shown). Control unit 120 may then provide the obtained region-specific predetermined time(s) of day to controller 106, substantially as described hereinabove. Alternatively, control unit 120 may provide activation inputs, based on the obtained region-specific predetermined time(s) of day, to the controller 106, without providing the region-specific predetermined time(s) of day to the controller, substantially as described hereinabove.

In some embodiments, in which the capsule 101 is adapted to mitigate jetlag, the predetermined time of day is suited to the geographic region from which the capsule, the control unit 120, or the subject, originate, or to the origin time zone of the subject. For example, if the subject has ingested the capsule, and has changed time zones since ingesting the capsule (for example flew from New-York to Chicago), the predetermined time of day is preferably maintained at the origin time zone of the origin location of the subject.

In some embodiments, the predetermined time of day is suited to the geographic region at which the capsule, the control unit 120, or the subject, arrive, or to the destination time zone of the subject. For example, if the subject has ingested the capsule, and has changed time zones since ingesting the capsule (for example flew from New-York to Chicago), the predetermined time of day is preferably maintained at the destination time zone at which the subject has arrived.

In some embodiments, the capsule is adapted to operate in multiple cycles and/or during multiple predetermined times of day. In some such embodiments, in a first cycle or predetermined time of day, the time is suited to the geographic region from which the capsule, the control unit 120, or the subject, originate, or to the origin time zone of the subject, and in a second cycle or predetermined time of day, the time is suited to the geographic region at which the capsule, the control unit 120, or the subject, arrive, or to the destination time zone of the subject.

In some embodiments, the predetermined time of day is suited to the circadian cycle of the user, or to a default circadian cycle. For example, the predetermined time of day may be one occurring a predetermined duration prior to, or near, a time that, according to the circadian cycle, the user is likely to have a bowel movement, such that operation of the capsule 101 may "assist" the gastrointestinal tract in generating, or completing, such a bowel movement. Additional examples relating to the circadian cycle are described hereinbelow with respect to FIG. 3. In some embodiments, the predetermined time of day may be selected to be a time of day at which the gastric pH of the user is relatively high, as explained in further detail hereinbelow with respect to FIG. 4.

In some embodiments, controller 106 only activates vibrating agitator 104 in the vibrating mode of operation at the predetermined time, if some minimum threshold duration has passed since capsule 101 was activated to be in the operative state, since receipt of the activation input, or since the user ingested the capsule. For example, the capsule may be pre-programmed such that controller 106 is adapted to activate vibrating agitator in the vibrating mode of operation from 6 am to 8 am, and from 6 pm to 8 pm, and the minimum threshold duration is four hours from ingestion of the capsule. If the subject ingests the capsule at 12 pm on Sunday, controller 106 would cause vibrating agitator 104 to operate in the vibrating mode of operation at 6 pm on Sunday, since the predetermined time of 6 pm is six hours following ingestion. However, if the subject ingests the capsule at 5 pm on Sunday, controller 106 would cause vibrating agitator 104 to operate in the vibrating mode of operation only at 6 am on Monday, since the first predetermined time of 6 pm is fewer than four hours following ingestion. Such a threshold duration may be particularly useful when it is desired that the capsule vibrate in a specific region or portion of the gastrointestinal tract, so that the delay time is required for the capsule to reach the specific region.

Relating to the characteristics of vibrating agitator 104, the vibrating agitator may be any suitable mechanism that can be intermittently activated and can apply suitable forces onto capsule housing 102.

In some embodiments, intermittently activated vibrating agitator 104 may include a radial agitator adapted to exert radial forces on capsule housing 102, in a radial direction with respect to the longitudinal axis of housing 102. For example, the radial agitator may include an unbalanced weight attached to a shaft of an electric motor powered by a battery or by power source 108, substantially as described in U.S. Pat. No. 9,707,150, which is incorporated by reference for all purposes as if fully set forth herein.

In some embodiments, intermittently activated vibrating agitator 104 may include an axial agitator adapted to exert radial forces on the capsule housing 102, in an axial direction with respect to a longitudinal axis of housing 102. For example, the axial agitator may include an electric motor powered by a battery or by power source 108, and an urging mechanism, associated with, and driven by, the electric motor, such that the urging mechanism adapted to exert said axial forces, substantially as described in U.S. Pat. No. 9,707,150. In some embodiments, the urging mechanism is adapted to exert the axial forces in opposite directions. In some embodiments, the urging mechanism is adapted to deliver at least a portion of the axial forces in a knocking mode.

In some embodiments, the forces exerted by intermittently activated vibrating agitator 104 on capsule housing 102 in the vibration mode of operation include radial forces in a radial direction with respect to the longitudinal axis of the housing and axial forces in an axial direction with respect to the longitudinal axis. In some embodiments, a single agitator exerts both the radial and the axial forces. In other embodiments, the axial forces are exerted by one agitator, and the radial forces are exerted by another, separate, agitator, where both agitators form part of intermittently activated vibrating agitator 104.

In some embodiments, the intermittently activated vibrating agitator 104 may include a magnet mounted onto a rotor adapted to exert a magnetic field as well as radial forces on capsule housing 102. For example, such a magnetic vibrating agitator is described in U.S. patent application Ser. No. 15/058,216 filed on Mar. 2, 2016 (and published as US 2016/0310357), and entitled "PHYSIOTHERAPY DEVICE AND METHOD FOR CONTROLLING THE PHYSIOTHERAPY DEVICE", which is incorporated by reference for all purposes as if fully set forth herein.

In some embodiments, housing 102 may include first and second members, and vibrating agitator 104 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In the vibrating mode of operation, intermittently activated vibrating agitator 104 is adapted to have a plurality of vibration cycles, where each cycle includes a vibration duration followed by a repose duration. Forces are exerted by the vibrating agitator 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitator 104 is operative in the vibration mode for a first duration, for example 30 minutes, then does not have any vibration cycles for a second duration, for example 1 hour, and then is operative in the vibration mode of operation and has vibration cycles for a third duration, for example two hours. The cumulative duration relates to the sum of all durations during which vibrating agitator 104 was operative in the vibration mode of operation and included vibration cycles, including the vibration duration and the repose duration of each vibration cycle.

In some embodiments, vibrating agitator 104 is configured to exert forces on the capsule housing 102, such that a net force exerted by the capsule housing 102 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitator 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitator.

It will be further appreciated that a specific capsule may be controlled by the controller such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Controller 106 is adapted to control the operation of intermittently activated vibrating agitator 104. Such control may include control of any one or more of the force applied by the vibrating agitator, the vibrational frequency reached, the times in which vibrating agitator 104 operates in the vibration mode of operation, the vibration duration of each vibration cycle, the repose duration of each vibration cycle, the vibration cycle duration, and cumulative vibration duration of the vibrating agitators.

In some embodiments, controller 106 is adapted to receive information relating to the desired vibration protocol from control unit 120, prior to ingestion of the capsule or to activation thereof, or during the capsule's traversal of the subject's GI tract. For example, the information may be remotely transmitted from control unit 120 to controller 106, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes one or more of at least one predetermined time of day, a time delay from receipt of the information to the at least one predetermined time of day, a region in which the control unit is located, a desired number of vibration cycles, a desired vibration duration in each vibration cycle, a desired repose duration in each vibration cycle, a desired cumulative vibration duration, and the like.

In some embodiments, controller 106 is adapted to control vibrating agitator 104 so that the capsule applies forces to an environment thereof to effect a mechanical stimulation of the wall of the gastrointestinal tract of the subject at the predetermined time(s) of day.

Figure 1B:
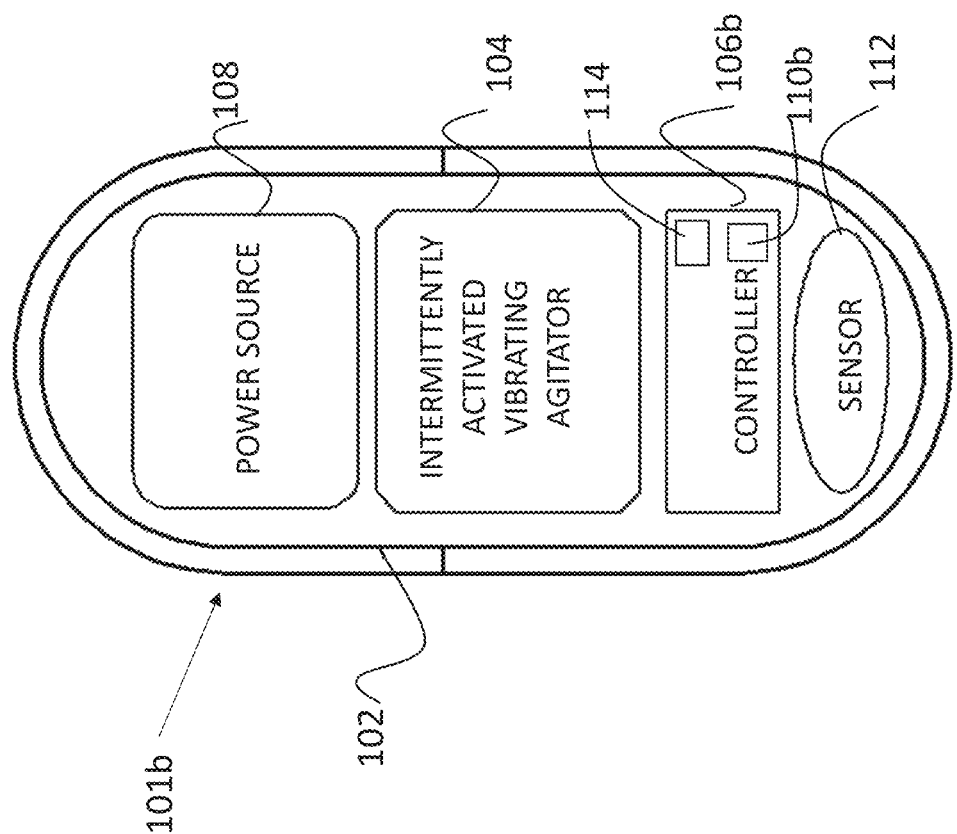

Turning to FIG. 1B, in one embodiment, the gastrointestinal treatment system includes only a vibrating ingestible capsule 101*b*. Capsule 101*b* includes a capsule housing or shell 102, arranged along a longitudinal axis and having disposed therein a vibrating agitator 104. Capsule 101*b* further includes a controller 106*b*, which may for example be, or include, a processor, is adapted to control operation of the vibrating agitator 104, and at least one power source 108 provides power to vibrating agitator 104 and controller 106*b*.

Shell 102, vibrating agitator 104, and power source 108, are all substantially as described hereinabove with respect to FIG. 1A.

Capsule 101*b* further includes a clock 110*b*, and at least one sensor 112, both functionally associated with controller 106*b* and both powered by power source 108.

The at least one sensor 112 is adapted to sense at least one parameter within capsule 101*b* or in an environment of capsule 101*b*, to identify a specific condition in capsule 101*b* or in the vicinity thereof, and to provide an activation input to controller 106 in response to identification of the condition. Typically, the condition is indicative of the subject ingesting capsule 101*b*. Examples of suitable sensors and conditions are provided hereinabove with respect to FIG. 1A.

It is a particular feature of the embodiment of FIG. 1B that controller 106*b* is preprogrammed with at least one predetermined time of day as well as with a vibration protocol, as discussed hereinabove. Controller 106*b* is adapted, in response to receiving from sensor(s) 112 an indication that the capsule has been ingested, to activate clock 110*b* to track the time of day, so as to identify occurrence of the at least one preprogrammed predetermined time of day, and to activate vibrating agitator 104 to operate in the vibrating mode of operation, in accordance with the preprogrammed vibration protocol, at the at least one preprogrammed predetermined time of day.

In some embodiments, the capsule is in an inoperative state, until the receipt of the sensor indication, which causes controller 106*b* to transition the capsule from the inoperative state to an operative state.

The at least one preprogrammed predetermined time of day is typically at least one default time of day, which may be, or may coincide with, at least one default mealtime, as described hereinabove with respect to FIG. 1A. As discussed hereinabove, a bowel movement supported by or triggered by the vibration may occur at a later time than the predetermined time of day.

As discussed hereinabove, the at least one time of day may include at least two predetermined times of day, such as two mealtimes. In some embodiments, the vibrating agitator may operate in the vibrating mode of operation at the at least one, or at least two, predetermined times of day, in two or more consecutive days.

In some embodiments, the at least one preprogrammed predetermined time of day is suited to a default circadian cycle, for example of a person who is awake during the day and sleeps during the night. For example, the predetermined time of day may be one occurring a predetermined duration prior to a time that, according to the default circadian cycle, a subject is likely to have a bowel movement, such that operation of the capsule 101*b* may "assist" the gastrointestinal tract in generating, or completing, such a bowel movement. Additional examples relating to the circadian cycle are described hereinbelow with respect to FIG. 3.

In some embodiments, the clock 110*b* may be set to a default time zone, for example a time zone at the location capsule 101*b* is sold or provided. In such embodiments, the controller 106*b* will be adapted to activate vibrating agitator 104 to operate in the vibrating mode of operation at the preprogrammed predetermined time of day when that occurs in the default time zone, regardless of the actual location of the capsule. For example, if a subject received capsule 101*b* from a physician in New York, the clock 110*b* will be set to EST. If the subject then travels to London, and ingests the capsule in London, the capsule will still vibrate at the predetermined time of day according to EST, and not according to GMT.

In other embodiments, capsule 101*b* further includes a location sensor 114, such as a GPS or GLONASS receiver, functionally associated with controller 106*b*, which is adapted to identify the geographic location of the capsule. In some such embodiments, when the user travels from an origin time zone to a destination time zone (such as from EST to GMT, as in the previous example), the location sensor 114 provides to controller 106*b* an indication of the change in time zone, and controller 106*b* may reset clock 110*b* to the destination time zone, or may otherwise compensate for the change in time zone, such that the vibration will occur at the preprogrammed predetermined time of day in accordance with the destination time zone.

As discussed hereinabove with respect to FIG. 1A, in some embodiments, controller 106*b* only activates vibrating agitator 104 in the vibrating mode of operation at the preprogrammed predetermined time(s), if some minimum threshold duration has passed since controller 106*b* received an indication of ingesting of capsule 101*b*.

Figure 1C:
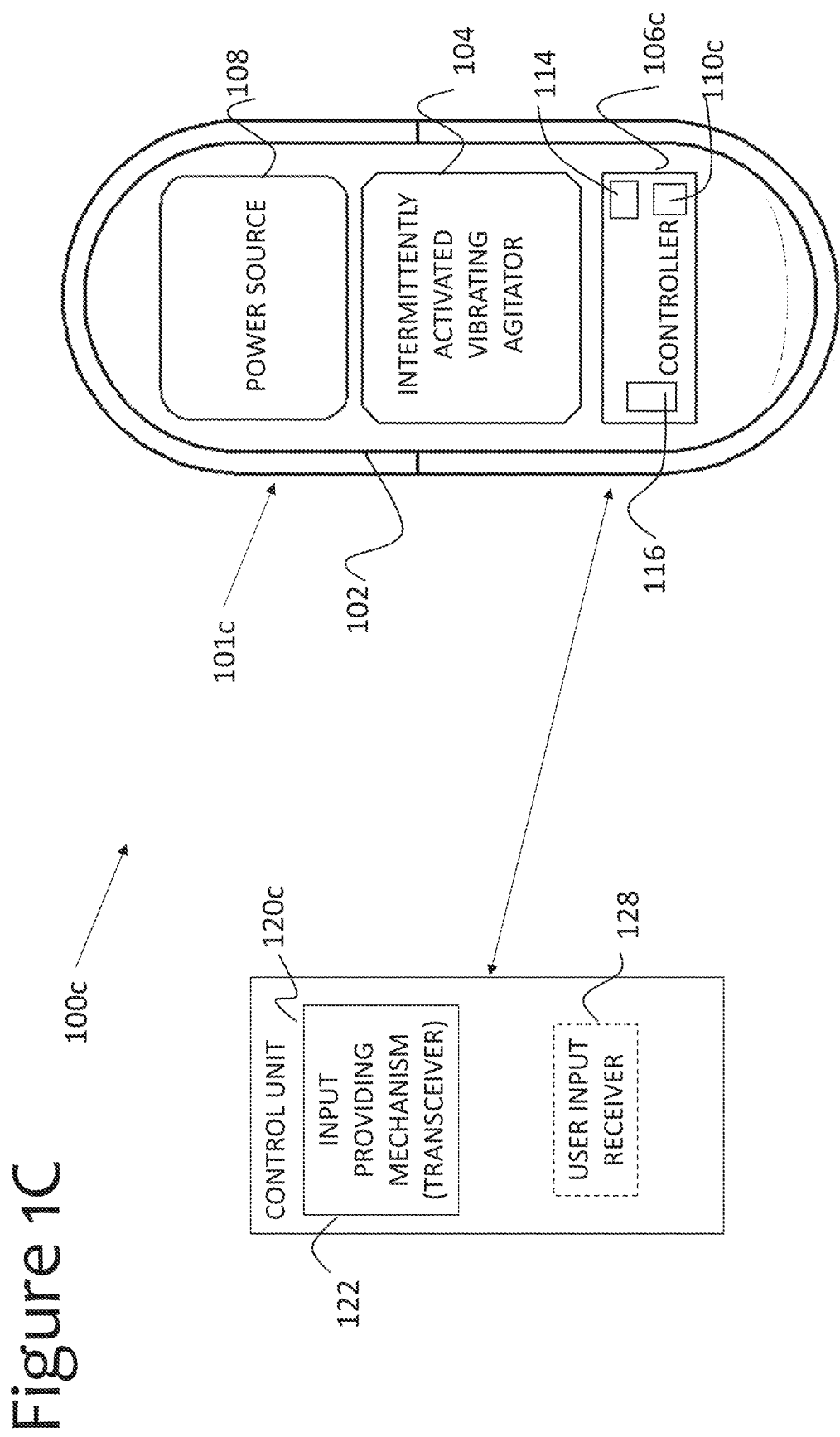

Turning to FIG. 1C, in one embodiment, the gastrointestinal treatment system 100*c* which includes a vibrating ingestible capsule 101*c*, as well as a control unit 120*c*. Capsule 101*c* includes a capsule housing or shell 102, arranged along a longitudinal axis and having disposed therein a vibrating agitator 104. Capsule 101*c* further includes a controller 106*c*, which may for example be, or include, a processor, is adapted to control operation of the vibrating agitator 104, and at least one power source 108 provides power to vibrating agitator 104 and controller 106*c*.

Shell 102, vibrating agitator 104, and power source 108, are all substantially as described hereinabove with respect to FIG. 1A.

Capsule 101*c* further includes a clock 110*c* and a remote input receiving mechanism 116, such as a transceiver, both powered by power source 108.

In the embodiment of FIG. 1C, controller 106*c* is preprogrammed with at least one predetermined time of day as well as with a vibration protocol, as discussed hereinabove. However, capsule 101*c* has no means for identifying when it has been ingested, for the controller 106*c* to begin its operation.

Control unit 120*c*, includes an input providing mechanism 122, such as a transceiver, adapted to provide an activation input to transceiver 116 of capsule 101*c*. Typically, the activation input is provided from control unit 120*c* to controller 106*c* when the subject places the capsule 101*c* on the control unit 120*c*, operates a specific program or application on control unit 120*c*, or otherwise indicates to control unit 120*c* that he is about to ingest the capsule. The subject typically ingests the capsule immediately following provision of the activation input.

In some embodiments, control unit 120*c* further includes a user input receiver (an input interface) 128 via which the subject, or a caretaker thereof, may provide an indication that the subject is about to ingest the capsule 101*c*.

Control unit 120*c*, transceiver 122, and user input receiver 128, may be substantially as described hereinabove with respect to FIG. 1A.

In some embodiments, control unit 120*c* is devoid of a timing mechanism.

Controller 106*c* is adapted, in response to receipt of the activation input from control unit 120*c*, to activate clock 110*c* to track the time of day, so as to identify occurrence of the at least one preprogrammed predetermined time of day, and to activate vibrating agitator 104 to operate in the vibrating mode of operation, in accordance with the preprogrammed vibration protocol, at the at least one preprogrammed predetermined time of day.

In some embodiments, the capsule is in an inoperative state, until the receipt of the activation input, which causes controller 106*c* to transition the capsule from the inoperative state to an operative state.

The at least one preprogrammed predetermined time of day is typically at least one default time of day, which may be, or may coincide with, at least one default mealtime, as described hereinabove with respect to FIG. 1A. As discussed hereinabove, a bowel movement supported by or triggered by the vibration may occur at a later time than the predetermined time of day.

As discussed hereinabove, the at least one time of day may include at least two predetermined times of day, such as two mealtimes. In some embodiments, the vibrating agitator may operate in the vibrating mode of operation at the at least one, or at least two, predetermined times of day, in two or more consecutive days.

In some embodiments, the at least one preprogrammed predetermined time of day is suited to a default circadian cycle, for example of a person who is awake during the day and sleeps during the night. For example, the predetermined time of day may be one occurring a predetermined duration prior to a time that, according to the default circadian cycle, a subject is likely to have a bowel movement, such that operation of the capsule 101*c* may "assist" the gastrointestinal tract in generating, or completing, such a bowel movement. Additional examples relating to the circadian cycle are described hereinbelow with respect to FIG. 3.

In some embodiments, the clock 110*c* may be set to a default time zone, for example a time zone at the location capsule 101*c* is sold or provided. In such embodiments, the controller 106*c* will be adapted to activate vibrating agitator 104 to operate in the vibrating mode of operation at the preprogrammed predetermined time of day when that occurs in the default time zone, regardless of the actual location of the capsule. For example, if a subject received capsule 101*c* from a physician in New York, the clock 110*c* will be set to EST. If the subject then travels to London, and ingests the capsule in London, the capsule will still vibrate at the predetermined time of day according to EST, and not according to GMT.

In other embodiments, capsule 101*c* further includes a location sensor 114, such as a GPS or GLONASS receiver, functionally associated with controller 106*c*, which is adapted to identify the geographic location of the capsule. In some such embodiments, when the user travels from an origin time zone to a destination time zone (such as from EST to GMT, as in the previous example), the location sensor 114 provides to controller 106*c* an indication of the change in time zone, and controller 106*c* may reset clock 110*c* to the destination time zone, or may otherwise compensate for the change in time zone, such that the vibration will occur at the preprogrammed predetermined time of day in accordance with the destination time zone.

As discussed hereinabove with respect to FIG. 1A, in some embodiments, controller 106*c* only activates vibrating agitator 104 in the vibrating mode of operation at the preprogrammed predetermined time(s), if some minimum threshold duration has passed since controller 106*c* received the activation input.

Turning now to FIG. 1D, the embodiment of FIG. 1D is substantially similar to that of FIG. 1C. The main difference between the embodiment of FIGS. 1C and 1D is that in the embodiment of FIG. 1D the gastrointestinal capsule is not preset with the predetermined time(s) of day, and receives these as part of the activation input, from the control unit.

As seen in FIG. 1D, the gastrointestinal treatment system 100*d* which includes a vibrating ingestible capsule 101*d*, as well as a control unit 120*d*. Capsule 101*d* includes a capsule housing or shell 102, arranged along a longitudinal axis and having disposed therein a vibrating agitator 104. Capsule 101*d* further includes a controller 106*d*, which may for example be, or include, a processor, is adapted to control operation of the vibrating agitator 104, and at least one power source 108 provides power to vibrating agitator 104 and controller 106*d*.

Shell 102, vibrating agitator 104, and power source 108, are all substantially as described hereinabove with respect to FIG. 1A.

Capsule 101*d* further includes a clock 110*d* and a remote input receiving mechanism 116, such as a transceiver, both powered by power source 108.

Control unit 120*d*, includes an input providing mechanism 122, such as a transceiver, adapted to provide an activation input to transceiver 116 of capsule 101*d*. The activation input includes at least one predetermined time of day at which the capsule 101*d* should be operative in the vibrating mode of operation. In some embodiments, the activation input may further include a vibration protocol, substantially as discussed hereinabove with respect to FIG. 1A.

Typically, the activation input is provided from control unit 120*d* to controller 106*d* when the subject places the capsule 101*d* on the control unit 120*d*, operates a specific program or application on control unit 120*d*, or otherwise indicates to control unit 120*d* that he is about to ingest the capsule. The subject typically ingests the capsule immediately following provision of the activation input.

In some embodiments, control unit 120*d* further includes a user input receiver (an input interface) 128 via which the subject, or a caretaker thereof, may provide an indication that the subject is about to ingest the capsule 101*d*.

Control unit 120*d*, may further include a timing mechanism 126 which is typically a clock, and may, in some embodiments, include a location sensor 124, as explained in further detail herein. Control unit 120*d*, transceiver 122, clock 126, location sensor 124, and user input receiver 128, may be substantially as described hereinabove with respect to FIG. 1A.

In some embodiments, the at least one predetermined time of day may be preset or preprogrammed in the control unit 120*d*. In some embodiments, the at least one time of day may be a default time of day, which may be, or may coincide with, at least one default mealtime, as described hereinabove with respect to FIG. 1A.

As discussed hereinabove, the at least one time of day may include at least two predetermined times of day, such as two mealtimes. In some embodiments, the vibrating agitator may operate in the vibrating mode of operation at the at least one, or at least two, predetermined times of day, in two or more consecutive days.

In other embodiments, the control unit 120*d* may be adapted to compute or otherwise determine the at least one predetermined time of day.

In some such embodiments, the control unit 120*d* may determine the predetermined time(s) of day based on a geographical location of the control unit, for example as identified by the location sensor 124, as described hereinabove with respect to FIG. 1A.

In other such embodiments, the control unit 120*d* may determine the predetermined time(s) of day based on user input received via user input receiver via user input receiver 128. In some embodiments, the control unit 120*d* determines the time(s) of day is suited to the user's circadian cycle, for example based on a sleep schedule and/or based on a meal schedule provided as part of the user input. For example, the predetermined time of day may be one occurring a predetermined duration prior to a time that, according to a default circadian cycle, a subject is likely to have a bowel movement, such that operation of the capsule 101d may "assist" the gastrointestinal tract in generating, or completing, such a bowel movement. Additional examples relating to the circadian cycle are described hereinbelow with respect to FIG. 3.

Controller 106d is adapted, in response to receipt of the activation input from control unit 120d, to activate clock 110d to track the time of day, so as to identify occurrence of the at least one predetermined time of day received as part of the activation input, and to activate vibrating agitator 104 to operate in the vibrating mode of operation, in accordance with a preprogrammed vibration protocol or a vibration protocol received as part of the activation input, at the at least one predetermined time of day.

In some embodiments, the capsule is in an inoperative state, until the receipt of the activation input, which causes controller 106d to transition the capsule from the inoperative state to an operative state.

In some embodiments, the clock 110d may be set to a default time zone, for example a time zone at the location capsule 101d is sold or provided. In some such embodiments, the controller 106d will be adapted to activate vibrating agitator 104 to operate in the vibrating mode of operation at the predetermined time of day when that occurs in the default time zone, regardless of the actual location of the capsule. For example, if a subject received capsule 101d from a physician in New York, the clock 110d will be set to EST. If the subject then travels to London, and ingests the capsule in London, the capsule will still vibrate at the predetermined time of day according to EST, and not according to GMT.

In other embodiments, when providing the activation input, control unit 120d may use clock 126 and location sensor 124 thereof to compensate for the change in time zone, such that the time of day provided to controller 106d is corrected to match the time zone at which the control unit is currently located.

In yet other embodiments, capsule 101d further includes a location sensor 114, such as a GPS or GLONASS receiver, functionally associated with controller 106d, which is adapted to identify the geographic location of the capsule. In some such embodiments, when the user travels from an origin time zone to a destination time zone (such as from EST to GMT, as in the previous example), the location sensor 114 provides to controller 106d an indication of the change in time zone, and controller 106d may reset clock 110d to the destination time zone, or may otherwise compensate for the change in time zone, such that the vibration will occur at the predetermined time of day in accordance with the destination time zone.

As discussed hereinabove with respect to FIG. 1A, in some embodiments, controller 106d only activates vibrating agitator 104 in the vibrating mode of operation at the predetermined time(s), if some minimum threshold duration has passed since controller 106d received the activation input (which is indicative of the subject planning to ingest the capsule).

Turning now to FIG. 1E, the embodiment of FIG. 1E is substantially similar to that of FIG. 1D. The main difference between the embodiment of FIGS. 1D and 1E is that in the embodiment of FIG. 1E the activation input does not include the predetermined time of day, but rather includes a time delay, from the current time, to the predetermined time of day.

As seen in FIG. 1E, the gastrointestinal treatment system 100e which includes a vibrating ingestible capsule 101e, as well as a control unit 120e. Capsule 101e includes a capsule housing or shell 102, arranged along a longitudinal axis and having disposed therein a vibrating agitator 104. Capsule 101e further includes a controller 106e, which may for example be, or include, a processor, is adapted to control operation of the vibrating agitator 104, and at least one power source 108 provides power to vibrating agitator 104 and controller 106e.

Shell 102, vibrating agitator 104, and power source 108, are all substantially as described hereinabove with respect to FIG. 1A.

Capsule 101e further includes a timer 110e and a remote input receiving mechanism 116, such as a transceiver, both powered by power source 108.

Control unit 120e, includes an input providing mechanism 122, such as a transceiver, adapted to provide an activation input to transceiver 116 of capsule 101e. The activation input includes at least one time delay time, from a current time of day to at least one predetermined time of day at which the capsule 101e should be operative in the vibrating mode of operation. In some embodiments, the activation input may further include a vibration protocol, substantially as discussed hereinabove with respect to FIG. 1A.

Typically, the activation input is provided from control unit 120e to controller 106e when the subject places the capsule 101e on the control unit 120e, operates a specific program or application on control unit 120e, or otherwise indicates to control unit 120e that he is about to ingest the capsule. The subject typically ingests the capsule immediately following provision of the activation input.

In some embodiments, control unit 120e further includes a user input receiver (an input interface) 128 via which the subject, or a caretaker thereof, may provide an indication that the subject is about to ingest the capsule 101e.

Control unit 120e, further includes a timing mechanism 126 which is typically a clock, and may, in some embodiments, include a location sensor 124, as explained in further detail herein. Control unit 120e, transceiver 122, clock 126, location sensor 124, and user input receiver 128, may be substantially as described hereinabove with respect to FIG. 1A.

In some embodiments, the at least one predetermined time of day may be preset or preprogrammed in the control unit 120e. In some embodiments, the at least one time of day may be a default time of day, which may be, or may coincide with, at least one default mealtime, as described hereinabove with respect to FIG. 1A.

As discussed hereinabove, the at least one time of day may include at least two predetermined times of day, such as two mealtimes. In some embodiments, the vibrating agitator may operate in the vibrating mode of operation at the at least one, or at least two, predetermined times of day, in two or more consecutive days.

In other embodiments, the control unit 120e may be adapted to compute or otherwise determine the at least one predetermined time of day.

In some such embodiments, the control unit 120e may determine the predetermined time(s) of day based on a geographical location of the control unit, for example as identified by the location sensor 124, as described hereinabove with respect to FIG. 1A.

In other such embodiments, the control unit 120e may determine the predetermined time(s) of day based on user input received via user input receiver via user input receiver 128. In some embodiments, the control unit 120e determines the time(s) of day is suited to the user's circadian cycle, for example based on a sleep schedule and/or based on a meal schedule provided as part of the user input. For example, the predetermined time of day may be one occurring a predetermined duration prior to a time that, according to the default circadian cycle, a subject is likely to have a bowel movement, such that operation of the capsule 101e may "assist" the gastrointestinal tract in generating, or completing, such a bowel movement. Additional examples relating to the circadian cycle are described hereinbelow with respect to FIG. 3.

Controller 106e is adapted, in response to receipt of the activation input from control unit 120e, to activate timer 110e to track passage of time until completion of the delay time, and to activate vibrating agitator 104 to operate in the vibrating mode of operation, in accordance with a preprogrammed vibration protocol or a vibration protocol received as part of the activation input, at a time coinciding with the at least one predetermined time of day.

In some embodiments, the capsule is in an inoperative state, until the receipt of the activation input, which causes controller 106e to transition the capsule from the inoperative state to an operative state.

In other embodiments, when providing the activation input, control unit 120e may use clock 126 and location sensor 124 thereof to compensate for a change in time zone, such as would be caused by a user travelling from New York to London, such that the delay time provided to controller 106e is corrected so that the vibration will occur at the predetermined time of day in the destination location, or at which the subject is currently located.

As discussed hereinabove with respect to FIG. 1A, in some embodiments, controller 106e only activates vibrating agitator 104 in the vibrating mode of operation following the delay time, if some minimum threshold duration has passed since controller 106e received the activation input (which is indicative of the subject planning to ingest the capsule).

It is a particular feature of the embodiment of FIG. 1E that, although the capsule 101e is not (necessarily) aware of the time of day, the control unit controls the capsule such that the vibrating mode of operation occurs at the predetermined time(s) of day.

Figure 1F:
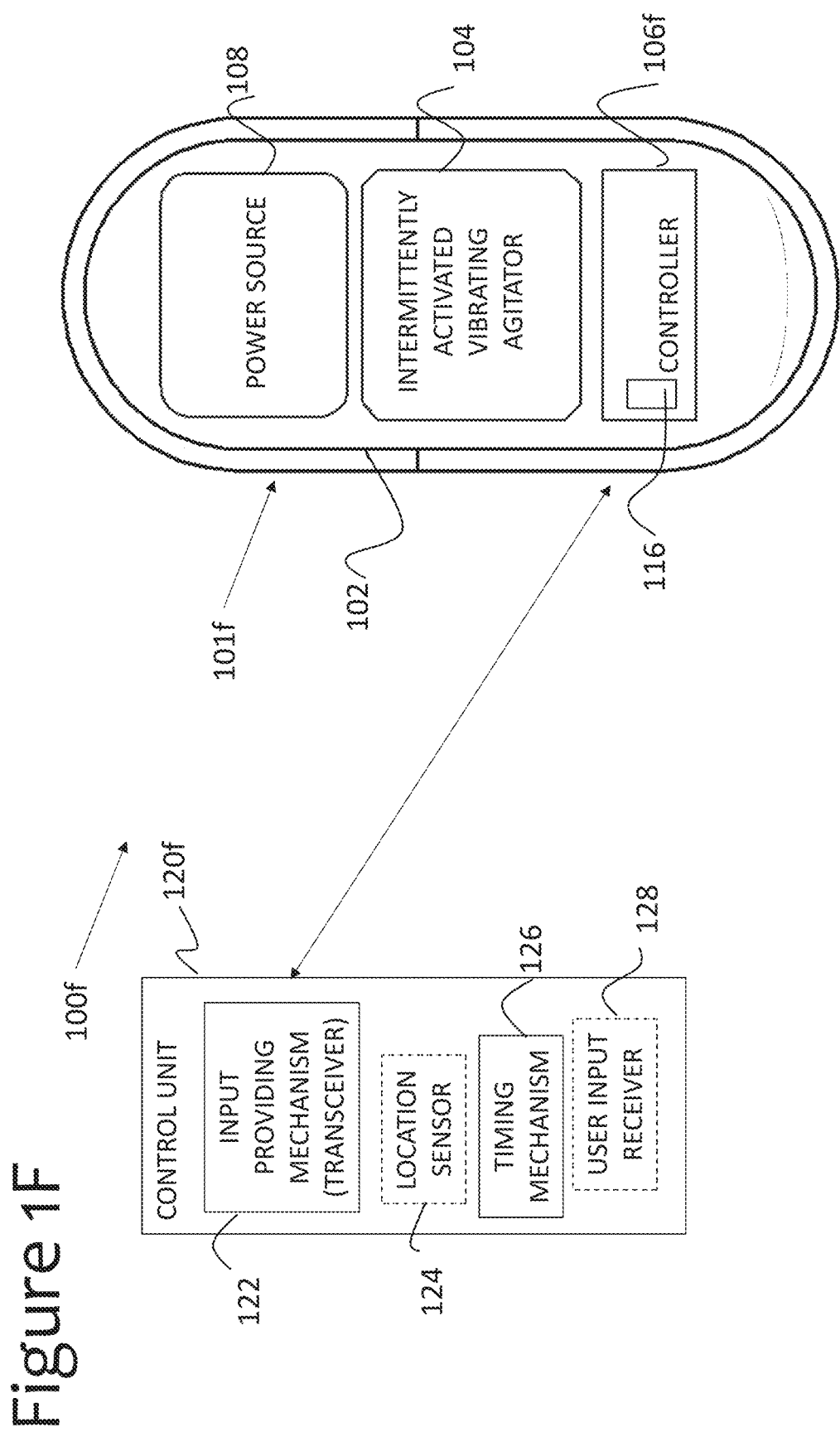

Turning now to FIG. 1F, the embodiment of FIG. 1F is distinct from the embodiments of FIGS. 1B to 1E in that the activation input is provided at the predetermined time of day, after the user has ingested the gastrointestinal capsule.

As seen in FIG. 1F, the gastrointestinal treatment system 100f which includes a vibrating ingestible capsule 101f, as well as a control unit 120f. Capsule 101f includes a capsule housing or shell 102, arranged along a longitudinal axis and having disposed therein a vibrating agitator 104. Capsule 101f further includes a controller 106f, which may for example be, or include, a processor, is adapted to control operation of the vibrating agitator 104, and at least one power source 108 provides power to vibrating agitator 104 and controller 106f.

Shell 102, vibrating agitator 104, and power source 108, are all substantially as described hereinabove with respect to FIG. 1A.

Capsule 101f further includes a remote input receiving mechanism 116, such as a transceiver, powered by power source 108. Transceiver 116 is sufficiently strong, or uses a suitable protocol, such that transceiver 116 can receive communications from outside the body, while capsule 101f traverses the GI tract.

Capsule 101f is devoid of a timing mechanism.

Control unit 120f, includes an input providing mechanism 122, such as a transceiver, adapted to communicate and to provide an activation input to transceiver 116 of capsule 101f, even following ingestion of the capsule. The activation input indicates to the controller 106f that the vibrating agitator should be operated in the first vibrating mode of operation now, at the time of receipt of the activation input. In some embodiments the activation input may include the vibration protocol to be used, substantially as described hereinabove with respect to FIG. 1A, and/or the duration for which the capsule should vibrate, in response to the activation input.

In some embodiments, a link between the capsule 101f and the control unit 120f may be formed when the subject places the capsule 101f on the control unit 120f, prior to ingestion of the capsule.

Control unit 120f, further includes a timing mechanism 126 which is typically a clock, and may, in some embodiments, include a location sensor 124, as explained in further detail herein. Control unit 120f, transceiver 122, clock 126, location sensor 124, and user input receiver 128, may be substantially as described hereinabove with respect to FIG. 1A.

In some embodiments, the at least one predetermined time of day may be preset or preprogrammed in the control unit 120f. In some embodiments, the at least one time of day may be a default time of day, which may be, or may coincide with, at least one default mealtime, as described hereinabove with respect to FIG. 1A.

As discussed hereinabove, the at least one time of day may include at least two predetermined times of day, such as two mealtimes. In some embodiments, the vibrating agitator may be activated, e.g. by the control unit, operate in the vibrating mode of operation at the at least one, or at least two, predetermined times of day, in two or more consecutive days.

In other embodiments, the control unit 120f may be adapted to compute or otherwise determine the at least one predetermined time of day.

In some such embodiments, the control unit 120f may determine the predetermined time(s) of day based on a geographical location of the control unit, for example as identified by the location sensor 124, as described hereinabove with respect to FIG. 1A.

In other such embodiments, the control unit 120f may determine the predetermined time(s) of day based on user input received via user input receiver via user input receiver 128. In some embodiments, the control unit 120f determines the time(s) of day is suited to the user's circadian cycle, for example based on a sleep schedule and/or based on a meal schedule provided as part of the user input. For example, the predetermined time of day may be one occurring a predetermined duration prior to a time that, according to the default circadian cycle, a subject is likely to have a bowel movement, such that operation of the capsule 101f may "assist" the gastrointestinal tract in generating, or completing, such a bowel movement. Additional examples relating to the circadian cycle are described hereinbelow with respect to FIG. 3.

Following ingestion of the capsule, when control unit 120f determines that the predetermined time of day has arrived, for example by tracking time using clock 126, it provides an activation input to controller 106f. Controller 106f is adapted, in response to receipt of the activation input from control unit 120f, to activate vibrating agitator 104 to operate in the vibrating mode of operation, in accordance with a preprogrammed vibration protocol or a vibration protocol received as part of the activation input, at a time coinciding with the at least one predetermined time of day.

In some embodiments, the capsule is in an inoperative state, until the linking of the capsule and the control unit, which causes controller 106f to transition the capsule from the inoperative state to an operative state.

It is a particular feature of the embodiment of FIG. 1F that, although the capsule 101f is not aware of the time of day, the control unit controls the capsule such that the vibrating mode of operation occurs at the predetermined time(s) of day.

Reference is now additionally made to FIGS. 2A to 2F, which are schematic flowcharts of embodiments of methods for treating the gastrointestinal tract according to the present invention, the treatment being based on use of the gastrointestinal treatment system of FIGS. 1A to 1F, respectively. For example, the methods of treatment illustrated in FIGS. 2A to 2F may be used for treating an ailment of the gastrointestinal tract, or for mitigating jetlag of the user.

It will be appreciated by people of skill in the art that the methods described herein may be used for treatment of various ailments of the gastrointestinal tract, including constipation, a sensation of straining while defecating, a sensation of gastric bloating, diarrhea, and gastroparesis.

It will further be appreciated by people of skill in the art that the methods described herein may be used for mitigating at least an acute constipation symptom of jetlag of a subject.

Turning to FIG. 2A, it is seen that at step 200, initially the treatment protocol for the subject is determined, for example by a treating physician or medical practitioner. The treatment protocol may indicate the number of treatment sessions per week or per other time duration, the time of day at which a capsule should be ingested, one or more predetermined times of day at which the capsule should be operative, and/or may indicate the vibration protocol of the capsule.

In some embodiments, for example when the treatment is intended to mitigate jetlag of a travelling subject, the treatment protocol may be selected at least partially according to a travel plan of the subject. As such, the treatment protocol may take into consideration, for example, times the subject will be in travelling (e.g. on an airplane, boat, or train), the origin time zone (from which the subject will be leaving), the destination time zone (at which the subject will be arriving), and the time of day at which the subject will be arriving at the destination.

At step 202, a controller 106 of an ingestible capsule 101 is provided with a predetermined time, or times, of day at which the vibrating agitator should be operated in the vibrating mode of operation. In some embodiments the controller is also provided with the number of consecutive days that the vibrating agitator should be operated in the vibrating mode of operation, at the predetermined time(s). In some embodiments, the controller may also be provided with a specification of a time zone to which the predetermined time(s) of day should relate, for example an origin time zone or a destination time zone of a travelling subject.

In some embodiments, at step 204 controller 106 may optionally receive, or be programmed with, a desired vibration protocol for the subject.

At step 206, the capsule may be activated for use, by transitioning the capsule from an inoperative state to an operative state, for example by receipt of an activation input.

The subject ingests the capsule at step 208, and at step 210 controller 106 control vibrating agitator 104 such that the vibrating mode of operation occurs at the predetermined time(s) of day, for the defined number of consecutive days.

In some embodiments, providing of the predetermined time(s) at step 202 and/or providing the desired vibration protocol for the subject at step 204 occurs at the time of manufacturing of the capsule, for example by pre-programming the time(s) into the controller.

In some embodiments, providing of the predetermined time(s) at step 202 and/or providing the desired vibration protocol for the subject at step 204 may be effected by a control unit, such as control unit 120 of FIG. 1A.

For example, control unit 120 may provide to controller 106 the predetermined time of day, a user-specific predetermined time of day, a region-specific predetermined time of day, or a time-zone specific time of day as described hereinabove. In such embodiments, step 202 may be carried out at any time prior to operating to the vibrating agitator in the vibrating mode of operation at step 210, and specifically may be carried out prior to ingestion of the capsule by the subject, or following the subject ingesting the capsule.

For example, the programming of the vibration protocol and/or of the predetermined time of day may include remotely transmitting the desired vibration protocol and/or predetermined time of day from the control unit 120 to the controller 106, for example using a short-range wireless communication method. In some embodiments, the desired vibration protocol is transmitted as a list of vibration parameters for effecting the vibration protocol. In some embodiments, the desired vibration protocol is transmitted as executable code for effecting the vibration protocol.

In some embodiments, the control unit provides the predetermined time of day to controller 106 at the predetermined time of day, which is equivalent to giving the command "operate the vibrating agitator 104 now". In such embodiments, step 202 is carried out following the subject ingesting the capsule at step 208.

As mentioned above, the capsule is activated for use at step 206. Typically, the capsule is activated by receipt of an activation input.

As discussed hereinabove, in some embodiments the activation input may be received from the control unit 120 or from sensors within the capsule sensing that the capsule has been ingested or that a user has carried out an activation motion with the capsule.

In some embodiments, the capsule is activated prior to the user ingesting the capsule at step 208, for example by a signal from the control unit or by the user carrying out an activation motion. In other embodiments, the activation input is provided at the time of ingestion or immediately thereafter, for example by sensors sensing a change in the environment of the capsule due to its ingestion, as described at length hereinabove.

In yet other embodiments, the activation input may be provided remotely when the capsule is already in the body of the subject, for example by remote communication from control module 120.

Following activation of capsule 101, or together therewith, capsule 101 is ingested by the subject, and begins to travel through the gastrointestinal tract of the subject, as seen at step 208.

Operation of vibrating agitator 104 in the vibrating mode of operation at step 210 effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm. In some embodiments, for example when the method of FIG. 2A is used to treat an ailment of the gastrointestinal tract, a treatment session as defined in steps 202 to 210 may be repeatedly administered to the subject as specified in the treatment protocol for the subject, determined or obtained at step 200. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks. In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

Figure 2B:
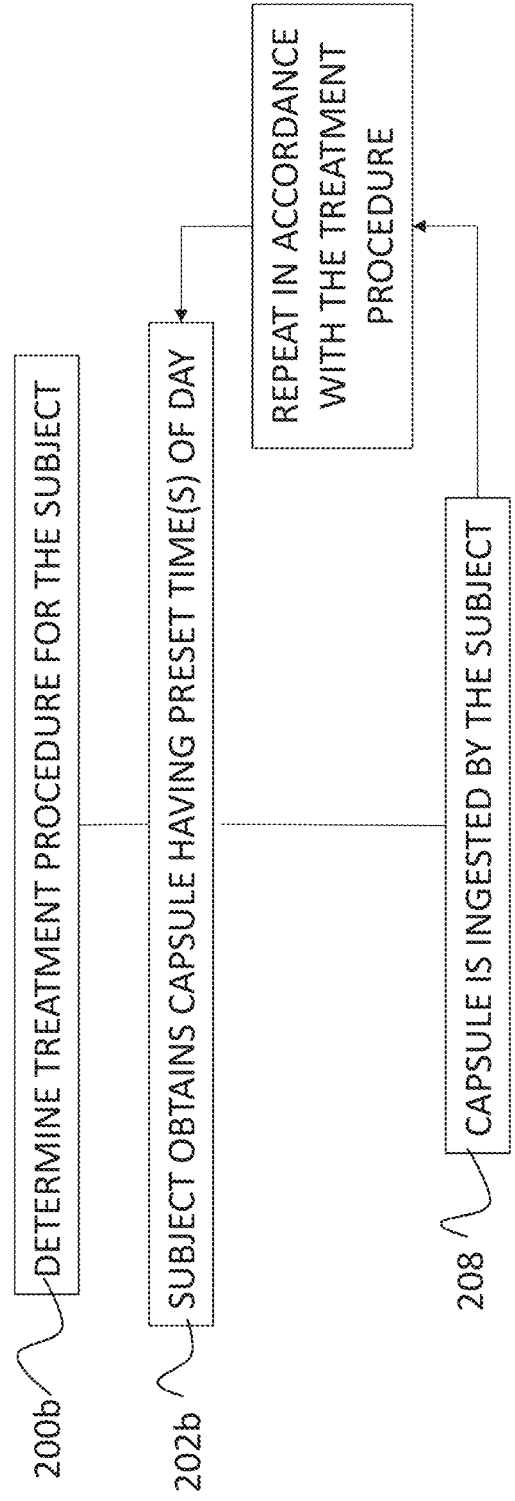

Turning now to FIG. 2B, it is seen that at step 200*b*, initially the treatment procedure for the subject may be determined, for example by a treating physician or medical practitioner. The treatment procedure may indicate the number of treatment sessions per week or per other time duration and/or the time of day at which a capsule should be ingested.

At step 202*b*, the subject obtains a vibrating ingestible capsule, for example capsule 101*b* as described hereinabove with respect to FIG. 1B. A controller 106*b* of the capsule is preprogrammed with a predetermined time, or times, of day at which the vibrating agitator should be operated in the vibrating mode of operation, with the number of consecutive days that the capsule should be operated in the vibrating mode of operation at the predetermined time(s), and with a vibration protocol for the vibrating mode of operation.

The subject ingests the capsule at step 208. Upon ingestion of the capsule, sensor 112 of capsule 101*b* provides to controller 106*b* an input indicating that the capsule has been ingested, and the controller track time and activates vibrating agitator 104 such that the vibrating mode of operation occurs at the predetermined time(s) of day. Operation of vibrating agitator 104 in the vibrating mode of operation effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm.

In some embodiments, for example when the method of FIG. 2B is used to treat an ailment of the gastrointestinal tract, a treatment session as defined in steps 202*b* and 208 may be repeatedly administered to the subject as specified in the treatment procedure for the subject, determined or obtained at step 200*b*. In some embodiments, the treatment procedure includes administering a plurality of treatment sessions to the subject, substantially as described hereinabove with respect to FIG. 2B.

Figure 2C:
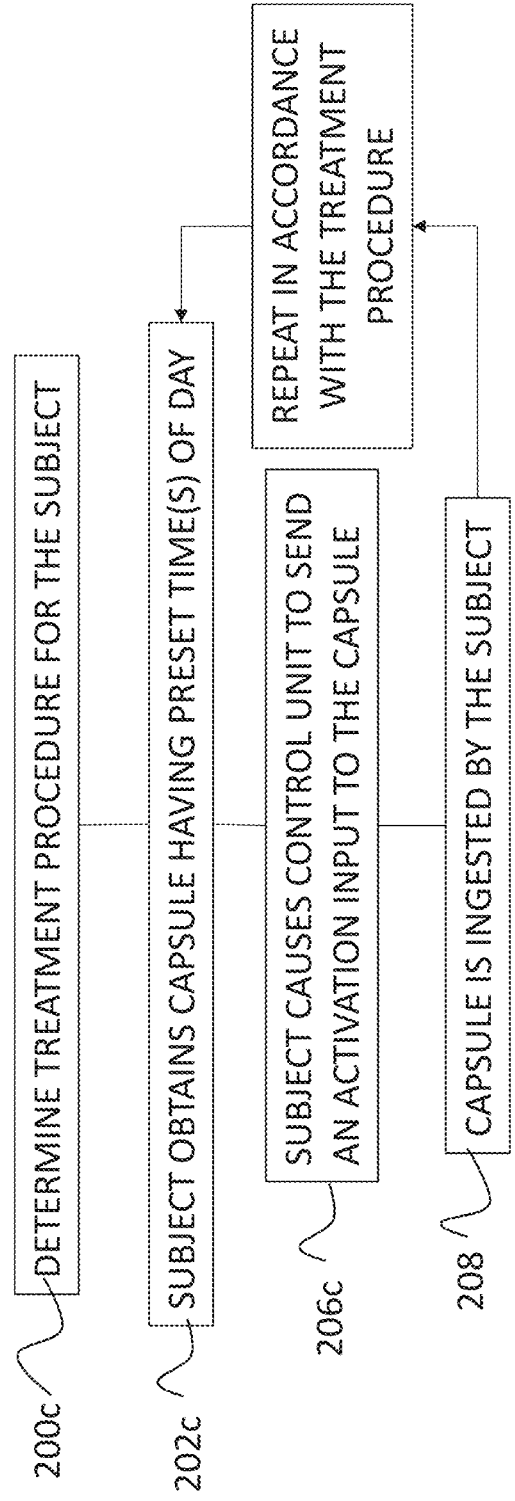

Turning now to FIG. 2C, it is seen that at step 200*c*, initially the treatment procedure for the subject may be determined, for example by a treating physician or medical practitioner. The treatment procedure may indicate the number of treatment sessions per week or per other time duration and/or the time of day at which a capsule should be ingested.

At step 202*c*, the subject obtains a vibrating ingestible capsule, for example capsule 101*c* as described hereinabove with respect to FIG. 1C. A controller 106*c* of the capsule is preprogrammed with a predetermined time, or times, of day at which the vibrating agitator should be operated in the vibrating mode of operation, with the number of consecutive days that the capsule should be operated in the vibrating mode of operation at the predetermined time(s), and with a vibration protocol for the vibrating mode of operation.

At step 206*c*, the subject causes a control unit, distinct from the capsule, such as control unit 120*c* of FIG. 1C, to provide an activation input to the capsule 101*c*. For example, the subject (or a caregiver thereof) may place the capsule in or on the control unit for a predetermined duration, so as to provide the activation input from the control unit to the capsule. As another example, the subject may operate an application running on the control unit, or otherwise provide a user input to the control unit, so as to trigger the control unit to send an activation input to the capsule.

Following provision of the activation input at step 206*c*, the subject ingests the capsule at step 208. Upon receipt of the activation input from control unit 120*c* (and regardless of actual ingestion of the capsule), controller 106*c* tracks time and activates vibrating agitator 104 such that the vibrating mode of operation occurs at the predetermined time(s) of day. Operation of vibrating agitator 104 in the vibrating mode of operation effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm.

In some embodiments, for example when the method of FIG. 2C is used to treat an ailment of the gastrointestinal tract, a treatment session as defined in steps 202*c* to 208 may be repeatedly administered to the subject as specified in the treatment procedure for the subject, determined or obtained at step 200*c*. In some embodiments, the treatment procedure includes administering a plurality of treatment sessions to the subject, substantially as described hereinabove with respect to FIG. 2C.

Figure 2D:
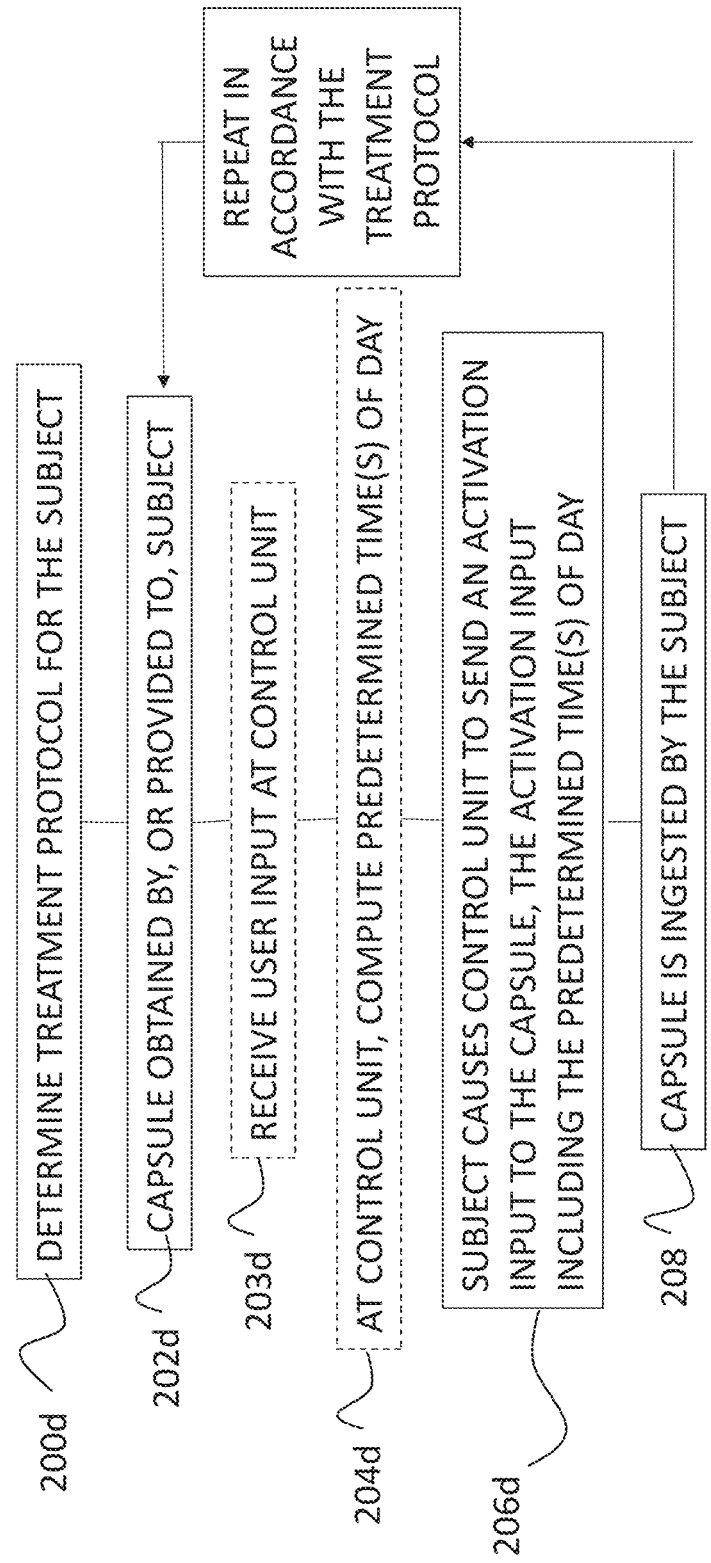

Turning now to FIG. 2D, it is seen that at step 200*d*, initially the treatment protocol for the subject is determined, for example by a treating physician or medical practitioner. The treatment protocol may indicate the number of treatment sessions per week or per other time duration, the time of day at which a capsule should be ingested, one or more predetermined times of day at which the capsule should be operative, a number of consecutive days that the capsule should be operated in the vibrating mode of operation at the predetermined time(s), and/or may indicate the vibration protocol of the capsule. Typically, at least a portion of the treatment protocol is provided to the control unit, such as control unit 120*d* of FIG. 1D.

At step 202*d*, the subject obtains, or is provided, a vibrating ingestible capsule, for example capsule 101*d* as described hereinabove with respect to FIG. 1D. In some embodiments, the capsule may be provided by a medical practitioner, such as a treating physician.

At step 206*d*, the subject causes the control unit, to provide an activation input to the capsule 101*d*. The activation input includes the at least one time of day at which the capsule should operate in the vibrating mode of operation, and in some embodiments may also include the number of consecutive days that the capsule should be operated in the vibrating mode of operation at the predetermined time(s), and/or the vibration protocol as determined at step 200*d*. For example, the subject (or a caregiver thereof) may place the capsule in or on the control unit for a predetermined duration, so as to provide the activation input from the control unit to the capsule. As another example, the subject may operate an application running on the control unit, or otherwise provide a user input to the control unit, so as to trigger the control unit to send an activation input to the capsule.

Following provision of the activation input at step 206*d*, the subject ingests the capsule at step 208. Upon receipt of the activation input from control unit 120*d* (and regardless of actual ingestion of the capsule), controller 106*c* tracks time and activates vibrating agitator 104 such that the vibrating mode of operation occurs at the predetermined time(s) of day received with the activation input. Operation of vibrating agitator 104 in the vibrating mode of operation effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm.

In some embodiments, at optional step 203*d*, a user input may be received at the control unit, for example via a user interface thereof. For example, the user input may include information pertaining to the circadian cycle of the subject, such as the subject's sleep schedule and/or meal schedule. The user input may be provided by the subject, medical personnel, or by a caregiver of the subject. The user input may be used to set, or to adjust, the predetermined time(s) of day for the subject.

In some embodiments, the predetermined time(s) of day is preset in the control unit, or is determined at step 200*d* and is provided to the control unit.

In other embodiments, at optional step 204*d*, the control unit computes the predetermined time(s) of day, prior to providing the activation input to the capsule. The computation may be based on user input received at step 203*d* or on a location of the control unit as identified by location sensor 124.

In some embodiments, for example when the method of FIG. 2D is used to treat an ailment of the gastrointestinal tract, a treatment session as defined in steps 202*d* to 208 may be repeatedly administered to the subject as specified in the treatment procedure for the subject, determined or obtained at step 200*d*. In some embodiments, the treatment procedure includes administering a plurality of treatment sessions to the subject, substantially as described hereinabove with respect to FIG. 2D.

Figure 2E:
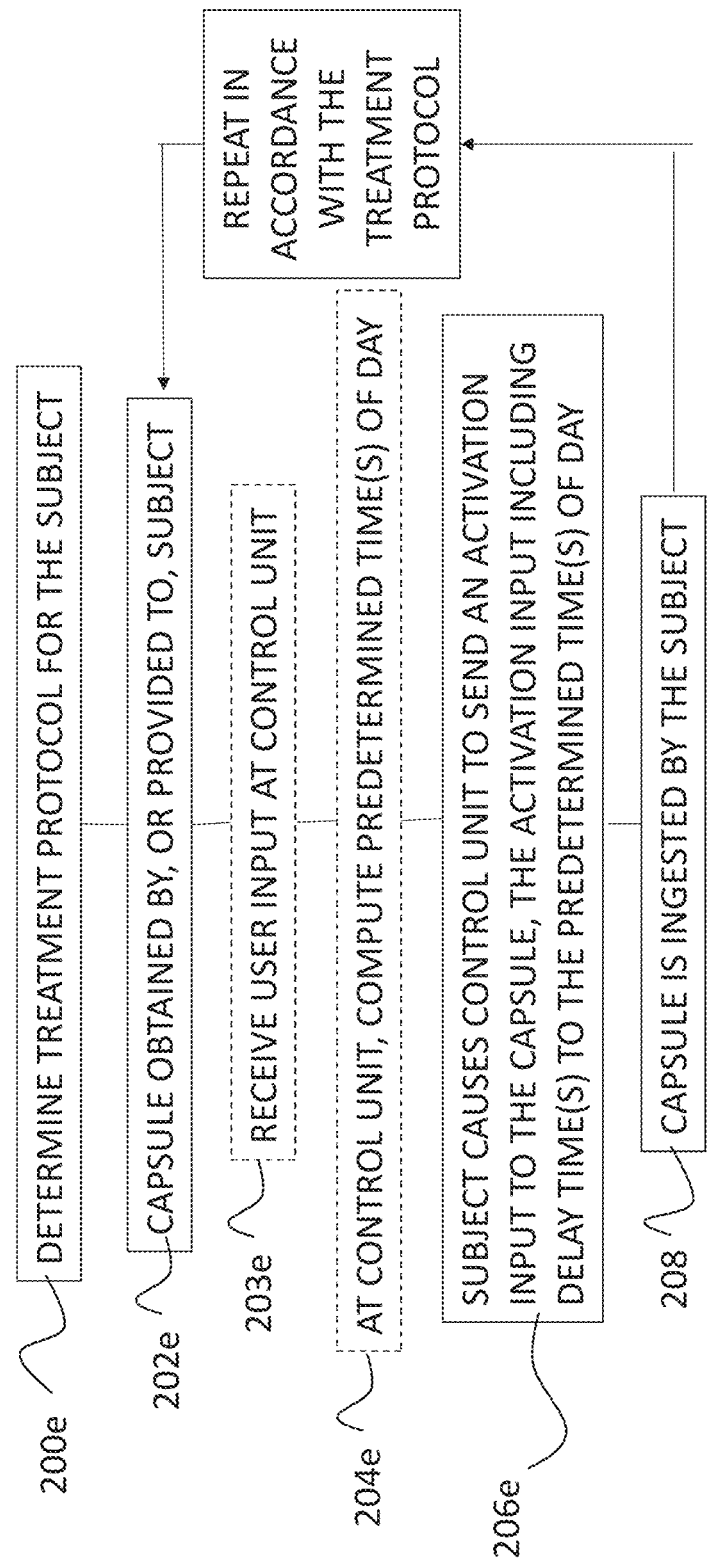

Turning now to FIG. 2E, it is seen that at step 200*e*, initially the treatment protocol for the subject is determined, for example by a treating physician or medical practitioner. The treatment protocol may indicate the number of treatment sessions per week or per other time duration, the time of day at which a capsule should be ingested, one or more predetermined times of day at which the capsule should be operative, a number of consecutive days that the capsule should be operated in the vibrating mode of operation at the predetermined time(s), and/or may indicate the vibration protocol of the capsule. Typically, at least a portion of the treatment protocol is provided to the control unit, such as control unit 120*e* of FIG. 1E.

At step 202*e*, the subject obtains, or is provided, a vibrating ingestible capsule, for example capsule 101*e* as described hereinabove with respect to FIG. 1E. In some embodiments, the capsule may be provided by a medical practitioner, such as a treating physician.

At step 206*e*, the subject causes the control unit, to provide an activation input to the capsule 101*e*. The activation input includes at least one-time delay from a current time to at least one time of day at which the capsule should operate in the vibrating mode of operation, and in some embodiments may also include the number of consecutive days that the capsule should be operated in the vibrating mode of operation at the predetermined time(s), and/or the vibration protocol as determined at step 200*e*. The at least one-time delay may be computed by the control unit, based on the current time and the predetermined time(s) of day. For example, the subject (or a caregiver thereof) may place the capsule in or on the control unit for a predetermined duration, so as to provide the activation input from the control unit to the capsule. As another example, the subject may operate an application running on the control unit, or otherwise provide a user input to the control unit, so as to trigger the control unit to send an activation input to the capsule.

Following provision of the activation input at step 206*e*, the subject ingests the capsule at step 208. Upon receipt of the activation input from control unit 120*e* (and regardless of actual ingestion of the capsule), controller 106*e* tracks passage of time until the at least one time delay has been completed, and activates vibrating agitator 104 to operate in the vibrating mode of operation, such that the vibrating mode of operation coincides with the predetermined time(s) of day. Operation of vibrating agitator 104 in the vibrating mode of operation effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm.

In some embodiments, at optional step 203*e*, a user input may be received at the control unit, for example via a user interface thereof. For example, the user input may include information pertaining to the circadian cycle of the subject, such as the subject's sleep schedule and/or meal schedule.

The user input may be provided by the subject, medical personnel, or by a caregiver of the subject. The user input may be used to set, or to adjust, the predetermined time(s) of day for the subject.

In some embodiments, the predetermined time(s) of day is preset in the control unit, or is determined at step 200e and is provided to the control unit.

In other embodiments, at optional step 204e, the control unit computes the predetermined time(s) of day, as well as the delay time(s), prior to providing the activation input to the capsule. The computation of the predetermined time(s) of day may be based on user input received at step 203e or on a location of the control unit as identified by location sensor 124.

In some embodiments, for example when the method of FIG. 2E is used to treat an ailment of the gastrointestinal tract, a treatment session as defined in steps 202e to 208 may be repeatedly administered to the subject as specified in the treatment procedure for the subject, determined or obtained at step 200e. In some embodiments, the treatment procedure includes administering a plurality of treatment sessions to the subject, substantially as described hereinabove with respect to FIG. 2E.

Figure 2F:
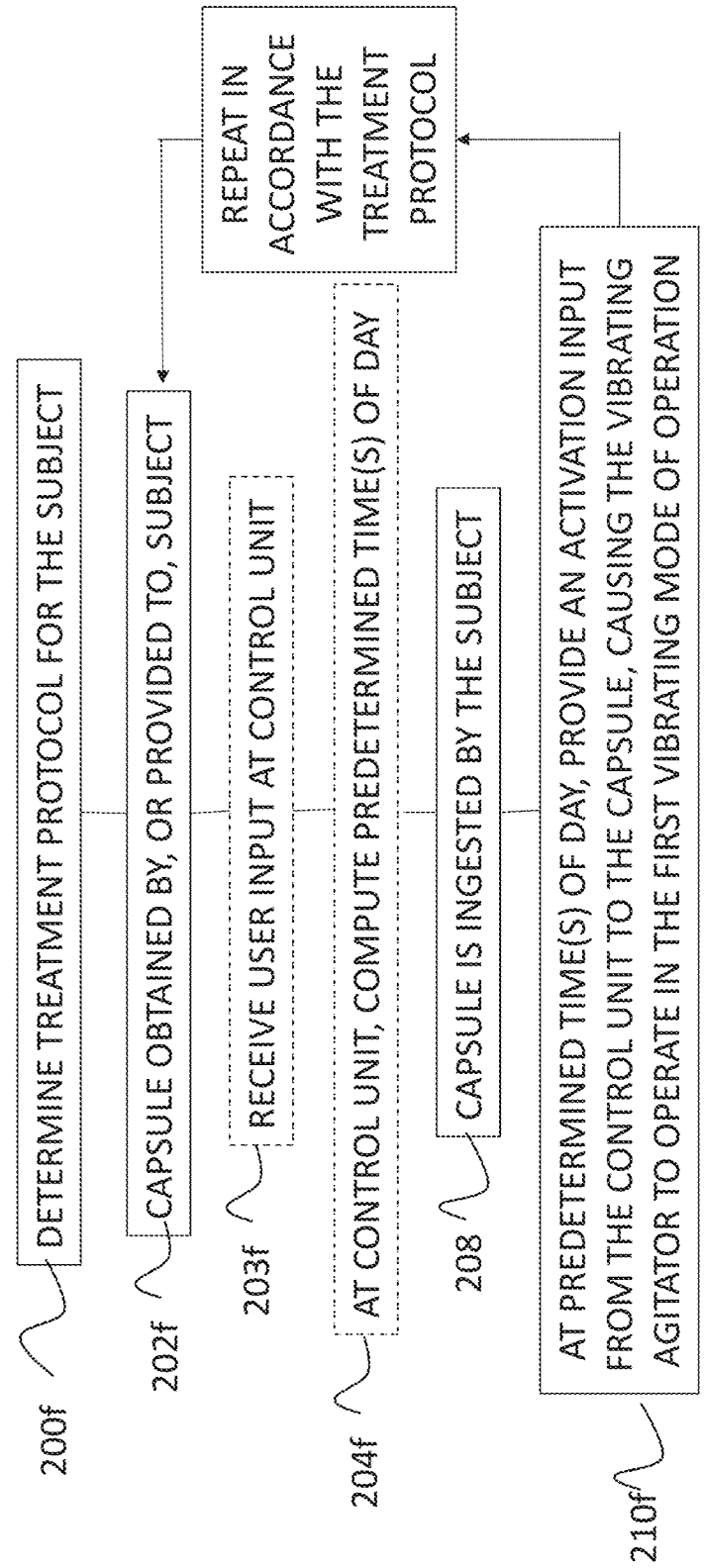

Turning now to FIG. 2F, it is seen that at step 200f, initially the treatment protocol for the subject may be determined, for example by a treating physician or medical practitioner. The treatment protocol may indicate the number of treatment sessions per week or per other time duration, the time of day at which a capsule should be ingested, one or more predetermined times of day at which the capsule should be operative, a number of consecutive days that the capsule should be operated in the vibrating mode of operation at the predetermined time(s), and/or may indicate the vibration protocol of the capsule. Typically, at least a portion of the treatment protocol is provided to the control unit, such as control unit 120f of FIG. 1F.

At step 202f, the subject obtains, or is provided, a vibrating ingestible capsule, for example capsule 101f as described hereinabove with respect to FIG. 1F. In some embodiments, the capsule may be provided by a medical practitioner, such as a treating physician.

The subject ingests the capsule at step 208.

Subsequently, at step 210f, at the at least one predetermined time of day, the control unit 120f provides an activation input to the capsule 101f. In some embodiments, the activation input may include the vibration protocol as determined at step 200f. Upon receipt of the activation input from control unit 120f, controller 106f, substantially immediately, activates vibrating agitator 104 to operate in the vibrating mode of operation, such that the vibrating mode of operation coincides with the predetermined time(s) of day. Operation of vibrating agitator 104 in the vibrating mode of operation effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at the predetermined time of day.

In some embodiments, providing the activation input at step 210f is responsive to a user input. In other embodiments, providing the activation input at step 210f is automatic, and is based on control unit 120f knowing the predetermined time(s) of day, and tracking time using clock 126 to identify the arrival of the predetermined time(s) of day.

In some embodiments, vibration of the capsule at the predetermined time of day, which effects the mechanical stimulation, triggers the subject to have an SBM or a CSBM at a later time of day than the vibration. For example, vibration of the capsule between 12 pm and 2 pm may trigger the subject to have a CSBM between 6 pm and 8 pm.

In some embodiments, at optional step 203f, a user input may be received at the control unit, for example via a user interface thereof. For example, the user input may include information pertaining to the circadian cycle of the subject, such as the subject's sleep schedule and/or meal schedule. The user input may be provided by the subject, medical personnel, or by a caregiver of the subject. The user input may be used to set, or to adjust, the predetermined time(s) of day for the subject.

In some embodiments, the predetermined time(s) of day is preset in the control unit, or is determined at step 200f and is provided to the control unit.

In other embodiments, at optional step 204f, the control unit computes the predetermined time(s) of day, prior to providing the activation input(s) to the capsule. The computation of the predetermined time(s) of day may be based on user input received at step 203f or on a location of the control unit as identified by location sensor 124.

In some embodiments, for example when the method of FIG. 2F is used to treat an ailment of the gastrointestinal tract, a treatment session as defined in steps 202f to 210f may be repeatedly administered to the subject as specified in the treatment procedure for the subject, determined or obtained at step 200f. In some embodiments, the treatment procedure includes administering a plurality of treatment sessions to the subject, substantially as described hereinabove with respect to FIG. 2F.

Figure 3:
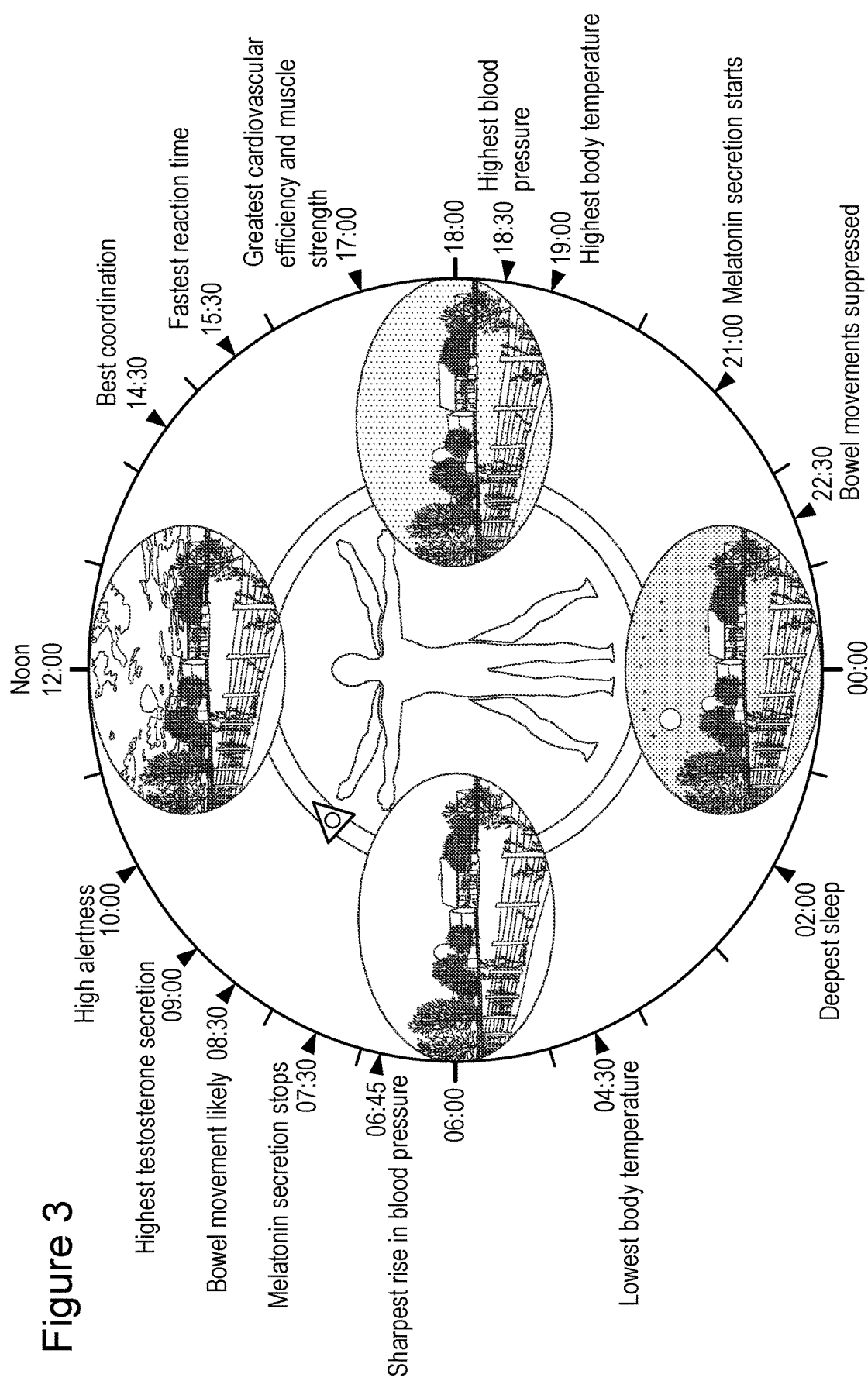
FIG. 3 is a schematic illustration of the circadian cycle of a person, including suitable times of day for the implementation of the methods of FIGS. 2A to 2F.

Reference is now made to FIG. 3, which is a schematic illustration of the circadian cycle of a person, including suitable times of day for the implementation of the methods of FIGS. 2A to 2F. The times of day shown in FIG. 3, and the corresponding body activities or characteristics at those times of day, are known in the art, and have been shown in medical and scientific research.

As will be noted, according to the typical circadian cycle shown in FIG. 3, a bowel movement is likely around 8:30 am, and bowel movements are suppressed around 10:30 pm (22:30).

As shown in the Examples below, Applicants have discovered that setting a vibrating ingestible capsule, such as the capsule described hereinabove with respect to FIG. 1, to vibrate during the morning hours (e.g. around 7:00-8:00 am) significantly increases the number of SBMs experienced by users in those hours.

Without wishing to be bound by theory, Applicants surmise that vibration during the morning hours, at which bowel movements are likely according to the circadian cycle, affects the walls of the gastrointestinal tract and promotes peristaltic movement, thereby assisting in completion of the bowel movement the body is likely to be promoting at that time. As shown in the Examples below, Applicants have further discovered that setting a vibrating ingestible capsule, such as the capsule described hereinabove with respect to FIG. 1, to vibrate during the evening hours (e.g. around 7:00-9:00 pm) significantly increases the number of SBMs experienced by users in those hours and/or in the morning hours, when the gastrointestinal system "wakes up".

Without wishing to be bound by theory, Applicants surmise that vibration during the evening hours, prior to the body suppressing bowel movements according to the circadian cycle, affects the walls of the gastrointestinal tract and promotes peristaltic movement, thereby assisting in creating an additional bowel movement "cleaning out" the GI tract before bowel movements are suppressed, and/or that the triggered peristaltic movement which assists in generating an SBM or CSBM in the morning hours.

Without wishing to be bound by theory, the Applicants further surmise that when the gastrointestinal tract is sufficiently active with contractions suitable for generating an SBM or a CSBM, such as during the morning hours or during breakfast time, any impact of the vibrations of the capsule is small relative to the contractions already occurring. The Applicants further surmise that when the digestive system is inactive, for example not during mealtimes, vibrations of the capsule are insufficient to generate peristaltic activity of the gastrointestinal tract. However, when the digestive system is active, but typically not enough to generate a bowel movement, activation of the capsule may "assist" the gastrointestinal tract in completing a bowel movement, resulting in an increase in the number of bowel movements the user experiences during a predefined duration, e.g. per week. Reference is now made to FIG. 4, which is a graphic illustration of the gastric pH of a person, indicating suitable times of day for the implementation of the methods of FIGS. 2A and 2F.

As seen in FIG. 4, the gastric pH of a typical person oscillates during the day, and is relatively high at typical mealtimes, and then decreases gradually until the next mealtime. Research has shown gastric pH is sensed by mechanoreceptors in the GI tract, and is tied to peristalsis in the GI tract (see for example "Acid sensing in the gastrointestinal tract" to Holtzer, (Am J Physiol Gastrointest Liver Physiol. 2007 March; 292(3): G699-G705, https://www.ncbi.nlm nih.gov/pmc/articles/PMC4370835/) in the section about Esophago-gastro-duodenal motility).

As shown in the Examples below, Applicants have discovered that setting a vibrating ingestible capsule, such as the capsule described hereinabove with respect to FIG. 1, to vibrate during typical mealtimes (during the morning hours and during the evening hours) significantly increases the number of SBMs experienced by users in those hours, or in a few hours following vibration.

Without wishing to be bound by theory, Applicants surmise that vibration at mealtimes, at which there are changes in the gastric pH according to the graph provided in FIG. 4, and during which times there is likely to be peristaltic activity in the GI tract, impacts the walls of the gastrointestinal tract and supports the peristaltic movement, thereby assisting in promoting bowel movements at those times.

EXAMPLES

Reference is now made to the following examples, which, together with the above description, illustrates the invention in a non-limiting fashion.

Example 1

A study which included 130 participating subjects suffering from constipation was conducted. Half of the participating subjects, termed herein "trial subjects", were treated with a vibrating gastrointestinal capsule according to a treatment protocol, in accordance with the present invention, while the other half, termed herein "sham subjects", were treated with a sham capsule, which appeared and behaved identically to the vibrating gastrointestinal capsule prior to ingesting thereof, but did not vibrate within the subject's alimentary tract.

The treatment protocol included treatment cycles including administering one gastrointestinal capsule per day five times per week, repeated for a treatment duration of six weeks. The administered capsules included a non-chargeable battery as the power source, and a coin-type eccentric vibration motor as the vibrating agitator.

The capsules administered to the "trial subjects" were programmed to have operate in the vibration mode of operation during the morning hours following an activation time delay of at least 8 hours, and when in the vibration mode of operation, to have vibration treatment cycles including a 3 second vibration duration followed by a 16 second repose duration, for a cumulative treatment duration of 1.5 to 3 hours. During the vibration mode of operation, the force applied by the capsule housing on the surrounding environment was in the range of 200 gram-force to 500 gram-force, and the vibrational frequency was in the range of 120 Hz to 280 Hz. Different specific forces were applied to the surrounding environment, and corresponding different vibrational frequencies were attained, in different vibration cycles of the administered capsules.

Due to the activation time delay, it is assumed that vibration was affected when the capsules were disposed in a section of the large intestine of the participating subjects.

The results of the study are shown in FIG. 5A, which illustrates the percentage of complete spontaneous bowel movements (CSBMs) relative to a time from ingestion of the capsules. As seen in FIG. 5A, at the times when vibration of the capsules is effected—between 8 and 11 hours after ingestion of the capsules and during the morning hours, the subjects receiving active capsules had a significantly greater number of CSBMs than those receiving sham capsules. As such, the results illustrated in FIG. 5A indicate that vibration of the capsules in the morning hours (e.g. at times at which bowel movements are likely according to the circadian cycle), and/or coinciding with mealtimes (e.g. at times at which gastric pH is low), improves the success of the treatment—thereby providing motivation for treating subjects at specific times of day.

Example 2

A study which included 26 participating subjects suffering from constipation was conducted. 16 of the participating subjects, termed herein "trial subjects", were treated with a vibrating gastrointestinal capsule according to a treatment protocol, in two different arms of the study, in accordance with the present invention, while the remaining ten subjects, termed herein "sham subjects", were treated with a sham capsule, which appeared and behaved identically to the vibrating gastrointestinal capsule prior to ingesting thereof, but did not vibrate within the subject's alimentary tract.

The treatment protocol included treatment cycles including administering one gastrointestinal capsule per day five times per week, repeated for a treatment duration of six weeks. The administered capsules included a non-chargeable battery as the power source, and a coin-type eccentric vibration motor as the vibrating agitator.

The capsules administered to the "trial subjects" were programmed to have operate in the vibration mode of operation during the early morning hours following an activation time delay of at least 8 hours, and to operate in the vibration mode of operation again during the afternoon hours. The capsules were programmed, when in the vibration mode of operation, to have vibration treatment cycles including a 3 second vibration duration followed by a 16 second repose duration, for a cumulative treatment duration of 1.5 to 3 hours. During the vibration mode of operation, the force applied by the capsule housing on the surrounding environment was in the range of 200 gram-force to 500 gram-force, and the vibrational frequency was in the range of 120 Hz to 280 Hz. Different specific forces were applied to the surrounding environment, and corresponding different vibrational frequencies were attained, in different vibration cycles of the administered capsules.

Due to the activation time delay, it is assumed that vibration was affected when the capsules were disposed in a section of the large intestine of the participating subjects.

Figure 5B:
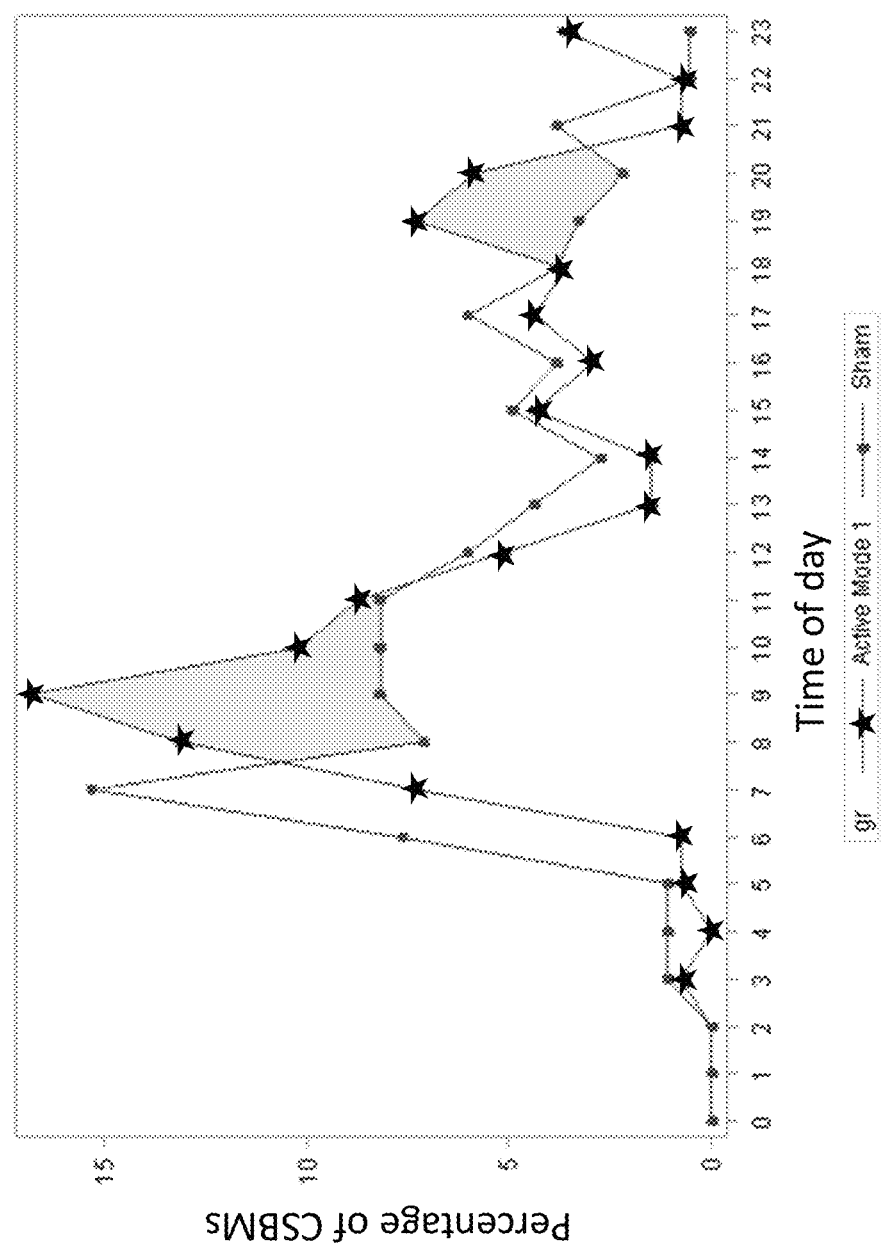

The results of the study are shown in FIG. 5B, which illustrates the percentage of complete spontaneous bowel movements (CSBMs) relative to a time from ingestion of the capsules. As seen in FIG. 5B, at the times when vibration of the capsules is effected—between 8 and 11 am, and between 7 and 9 pm, the subjects receiving active capsules had a significantly greater number of CSBMs than those receiving sham capsules. As such, the results illustrated in FIG. 5B indicate that improvement of the subject's symptoms of the subject's symptoms by addition of CSBMs is coincidental with times at which the capsule vibrates, thus demonstrating the efficacy of the capsules, and the benefit in activating the capsules to operate at specific times of day, which coincide with mealtimes and/or at which the circadian cycle indicates that a bowel movement is likely and prior to bowel movements becoming unlikely according to the circadian cycle.

Example 3

A study was conducted, which study included 299 participating subjects suffering from chronic idiopathic constipation according to the Rome III criteria and who have not experienced relief of their symptoms from available therapies. 155 of the participating subjects, termed herein "trial subjects", were treated with a vibrating gastrointestinal capsule according to a treatment protocol, in accordance with the present invention, while the remaining 144 subjects, termed herein "placebo subjects", were treated with a placebo capsule, which appeared identically to the vibrating gastrointestinal capsule prior to ingesting thereof, but disintegrated within the subject's alimentary tract.

All subjects were observed and monitored for two weeks, termed a "run-in period". During the run-in period, the subjects were asked to refrain from taking any medication or supplement to relieve their constipation. The subjects completed a diary every day, in which the subjects reported regarding their daily bowel movements, change of diet, change of symptoms, and change in general health conditions. The run in period was used to set a baseline for the number of SBMs, and CSBMs that each subject experiences per week.

During the trial period, subjects continued to complete the diary, and to report their experience regarding daily bowel movements, as well as regarding straining and consistency of bowel movements (in accordance with the Bristol stool scale).

The treatment protocol included treatment cycles including administering one gastrointestinal capsule per day five times per week, repeated for a treatment duration of eight weeks. The administered capsules included a non-chargeable battery as the power source, and a coin-type eccentric vibration motor as the vibrating agitator.

The capsules administered to the "trial subjects" were programmed to operate in the vibration mode of operation at two predetermined times of day, for approximately two hours each time, for a total of five vibration periods.

The capsules administered to the "trial subjects" were programmed to operate in the vibration mode of operation during lunchtime and again during suppertime, for three consecutive days. As such, each capsule vibrated during lunchtime and supper time on day 1, during lunchtime and suppertime on day 2, and during lunchtime on day 3, if the capsule was still in the gastrointestinal tract of the user.

The capsules were programmed, when in the vibration mode of operation, to have vibration treatment cycles including a 3 second vibration duration followed by a 16 second repose duration, for a cumulative treatment duration of 1.5 to 3 hours. During the vibration mode of operation, the force applied by the capsule housing on the surrounding environment was in the range of 200 gram-force to 500 gram-force, and the vibrational frequency was in the range of 120 Hz to 280 Hz. Different specific forces were applied to the surrounding environment, and corresponding different vibrational frequencies were attained, in different vibration cycles of the administered capsules.

The capsules were programmed to vibrate only following an activation time delay of at least 8 hours. Due to the activation time delay, it is assumed that vibration was affected when the capsules were disposed in a section of the large intestine of the participating subjects.

The capsules were programmed to vibrate for multiple consecutive days. Additionally, capsules were administered to the subjects five days per week, i.e. on some consecutive days. Consequently, there were times at which multiple capsules simultaneously operated in the vibration mode of operation within the gastrointestinal tract of a subject, at different locations along the gastrointestinal tract.

Results of the study, with respect to number of bowel movements, are shown in Table 1.

TABLE 1

| Result | Trial subjects | | | Placebo | | | p-value |
| --- | --- | --- | --- | --- | --- | --- | --- |
| | n | N | % | n | N | % | |
| At least 1 additional CSBM for at least 6 out of 8 weeks | 63 | 155 | 40.65 | 33 | 144 | 22.92 | <0.0001 |
| At least 2 additional CSBM for at least 6 out of 8 weeks | 36 | 155 | 23.23 | 17 | 144 | 11.81 | 0.0008 |

Figure 6A:
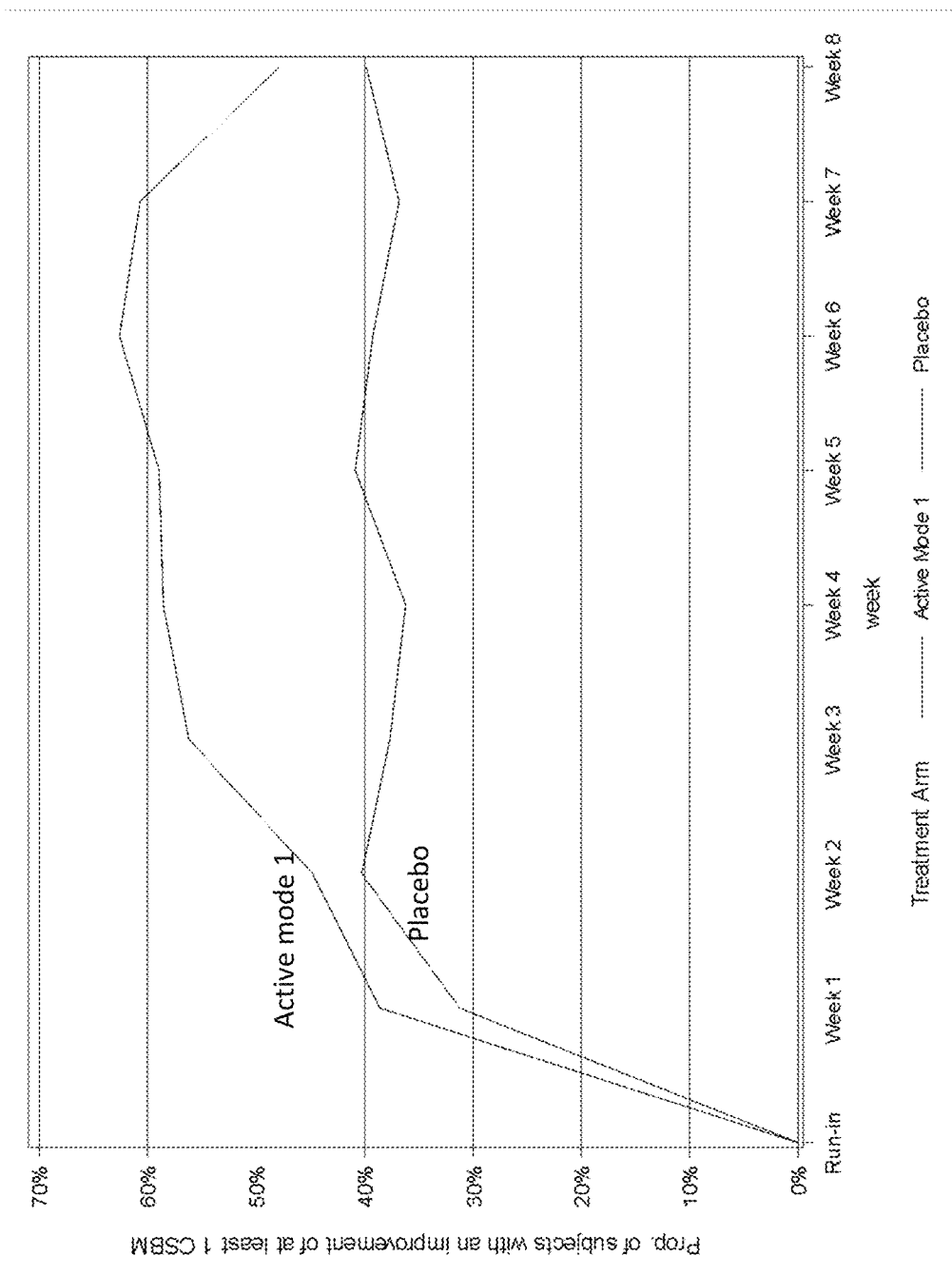
FIGS. 6A, 6B, 6C, and 6D are graphic representation of results of additional clinical experiments conducted using an ingestible vibrating gastrointestinal capsule as illustrated in FIG. 1A and using a method as illustrated in FIG. 2A.
Figure 6B:
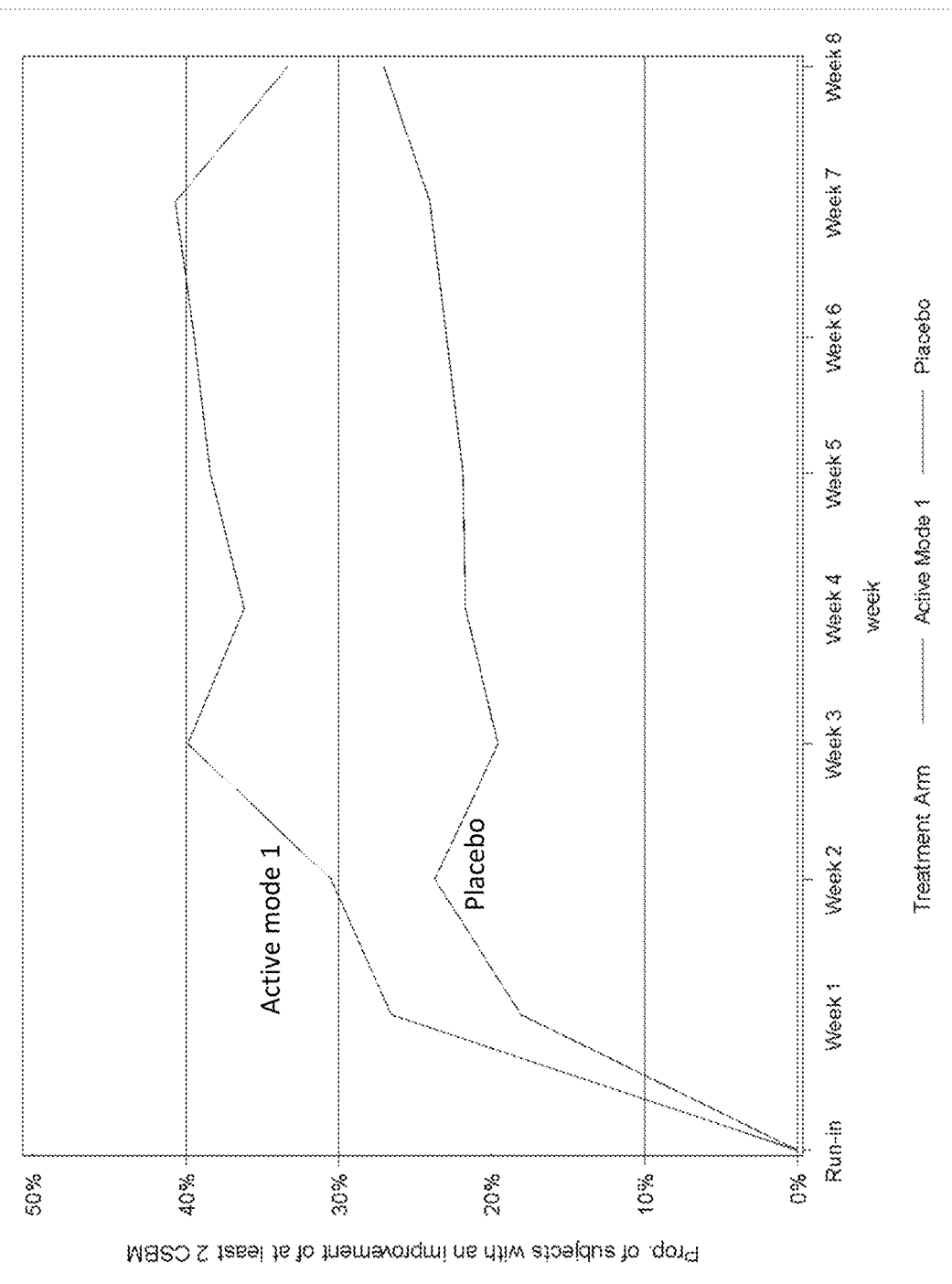

The results of the study with respect to number of bowel movements are further shown in FIGS. 6A and 6B. FIG. 6A illustrates the per-week proportion of subjects who had one additional CSBM relative to the baseline, for at least six out of eight weeks. FIG. 6B illustrates the per-week proportion of subjects who had two additional CSBMs relative to the baseline, for at least six out of eight weeks. Stated differently, for each week in FIGS. 6A and 6B, the value represents the percentage of the subjects who met the criteria (i.e. had one or two additional CSBM per week for six out of eight weeks) and who had an additional one or two CSBM on that specific week.

As is clearly evident from the results presented herein, more than 40% of the trial subjects experienced at least one additional CSBM per week for at least six out of the eight weeks. Furthermore, more than 23% experienced at least two additional CSBMs per week for at least six out of the eight weeks. The percentage of placebo subjects to experience the same level of improvement is approximately half that of the trial subjects, demonstrating the efficacy of the capsules.

Additionally, as discussed hereinabove, in Example 2 the percentage of subjects who experienced additional CSBMs is approximately 15%, as compared to the results of Example 3 in which the percentage of trial subjects who experienced additional CSBMs is greater than 23%. This is indicative of vibration during lunchtime and suppertime being more efficacious than vibration during breakfast time and lunchtime, and supports the Applicant's understanding regarding therapeutic windows for providing vibration.

Further, as discussed hereinabove, in Example 2 each capsule vibrated twice, i.e. for a single day. As a result, no two capsules were vibrating simultaneously in different parts of the GI tract. By contrast, in Example 3, two, and in some cases even three, capsules were vibrating concomitantly in different parts of the GI tract. As such, the difference in results between Examples 2 and 3 may indicate an advantage in providing simultaneous vibration by multiple capsules in different portions of the GI tract.

Comparison of the results of Examples 2 and 3 indicates that there are one or more better times for operation of vibrating capsules according to the present invention. Such better times may be during times in which the digestive system is active, e.g. during mealtime, but not during times that the gastrointestinal tract is sufficiently active with contractions suitable for generating an SBM or CSBM.

Without wishing to be bound by theory, the Applicants surmise that when the gastrointestinal tract is sufficiently active with contractions suitable for generating an SBM or a CSBM, such as during the morning hours or during breakfast time, any impact of the vibrations of the capsule is small, or even negligible, relative to the contractions already occurring. The Applicants further surmise that when the digestive system is inactive, for example not during mealtimes, vibrations of the capsule are insufficient to generate peristaltic activity of the gastrointestinal tract. However, when the digestive system is active, but typically not active enough to generate a bowel movement, activation of the vibrating capsule may "assist" the gastrointestinal tract in completing a bowel movement, resulting in an increase in the number of bowel movements the user experiences during a predefined duration, e.g. per week.

Figure 6C:
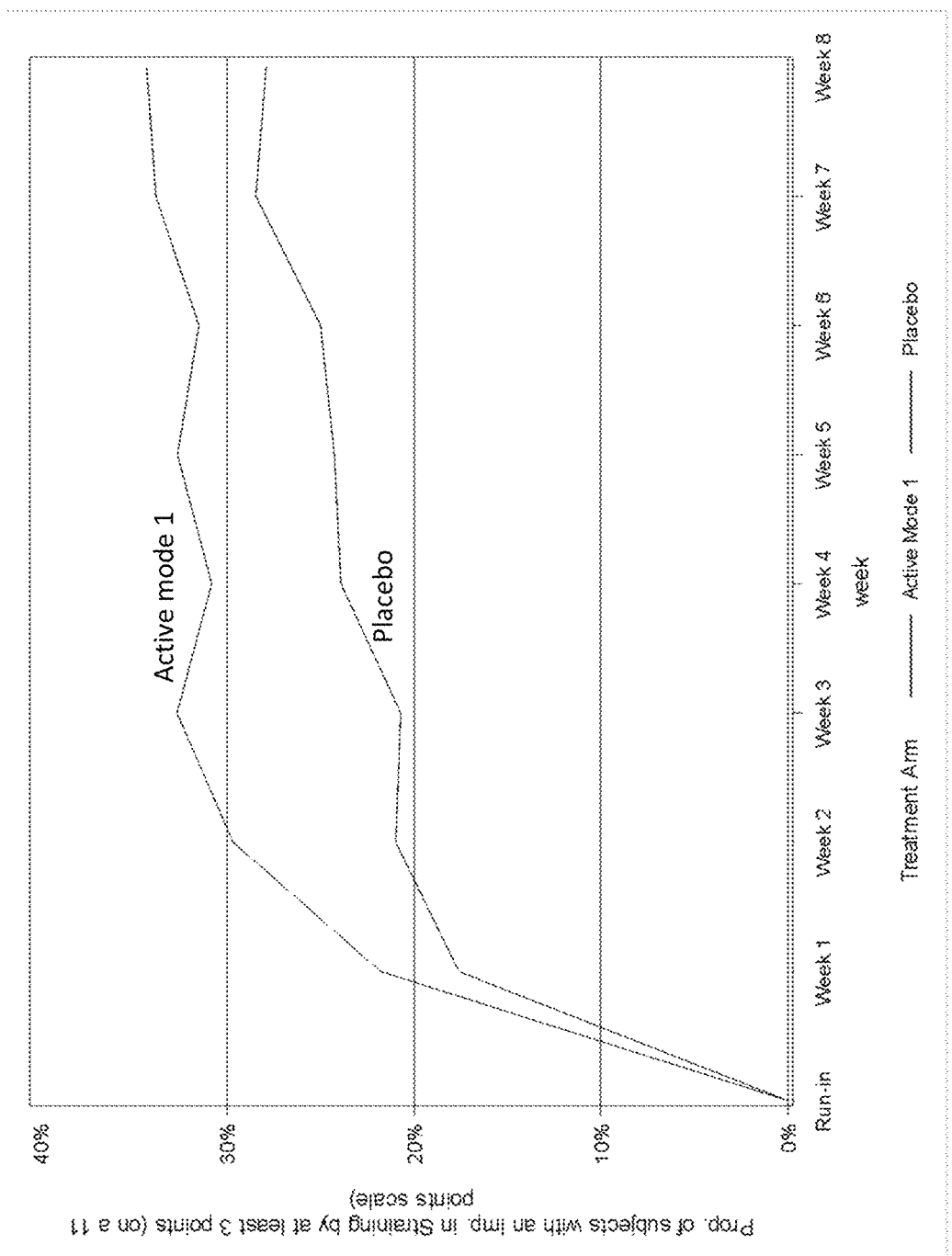

The results of the study with respect to straining are further shown in FIG. 6C. FIG. 6C illustrates the per-week proportion of subjects who experienced an improvement in straining (i.e. reduction of straining during defecating) of at least 3 points in an 11 point scale. Stated differently, for each week in FIG. 6C, the value represents the percentage of the subjects who met the criteria (i.e. had an improvement in straining of at least 3 points in the 11 point scale) and who experienced that improvement on that specific week.

As seen in FIG. 6C, during all eight weeks of the trial, the proportion of trial subjects who experienced an improvement of at least 3 points in straining is greater than the proportion of placebo subjects who experienced the same level of improvement. As seen, in at least six of the eight weeks of the trial, more than 30% of the trial subjects experienced an improvement in straining.

Figure 6D:
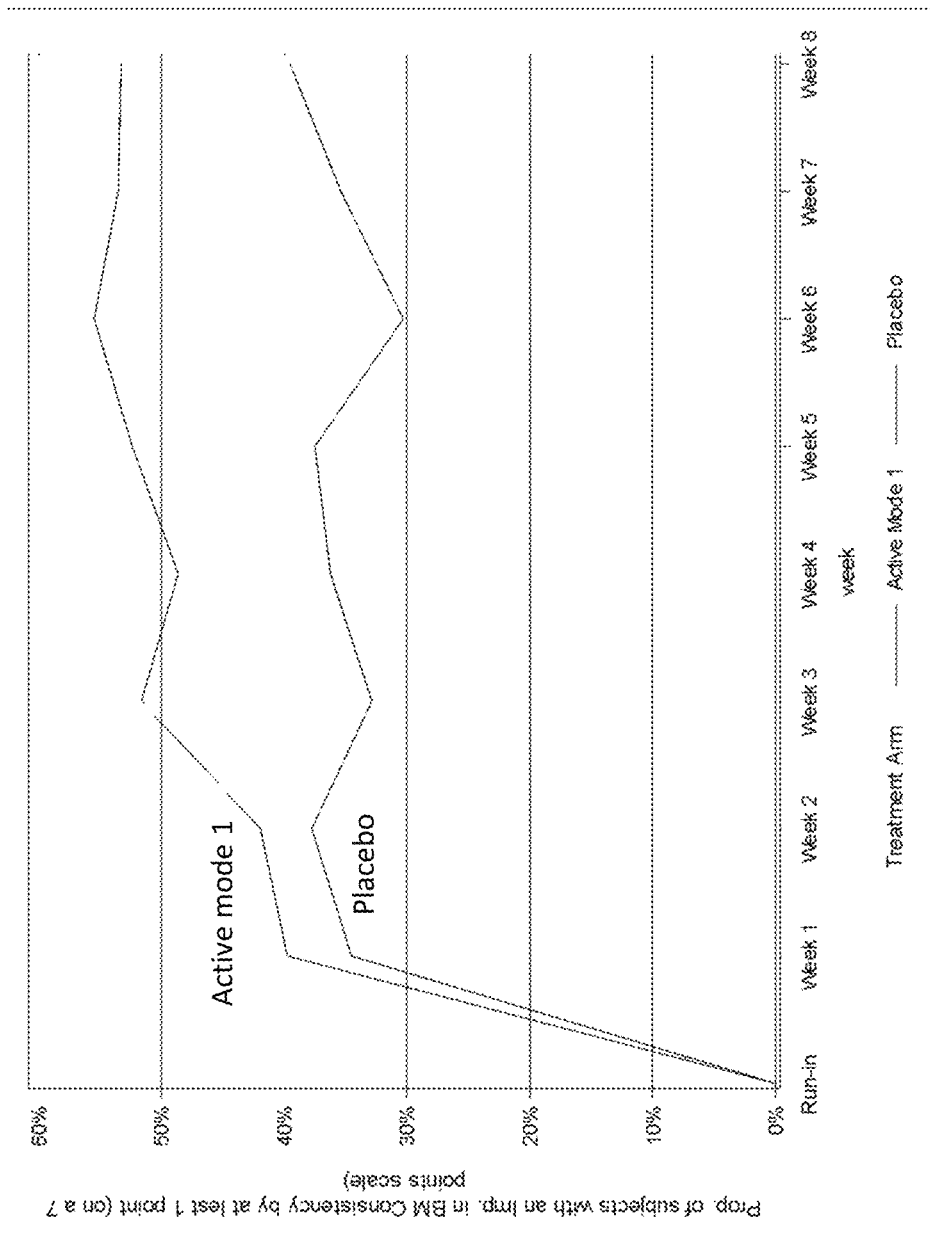

The results of the study with respect to stool consistency are further shown in FIG. 6D. FIG. 6D illustrates the per-week proportion of subjects who experienced an improvement in stool consistency (i.e. an increase in the Bristol stool score of defecations) of at least 1 points in the point Bristol stool scale. Stated differently, for each week in FIG. 6D, the value represents the percentage of the subjects who met the criteria (i.e. had an increase of at least 1 point in the Bristol stool score) and who experienced that improvement on that specific week.

As seen in FIG. 6D, during all eight weeks of the trial, the proportion of trial subjects who experienced an improvement of at least 1 points in the Bristol stool score is greater than the proportion of placebo subjects who experienced the same level of improvement. As seen, seven of the eight weeks of the trial, more than 40% of the trial subjects experienced an improvement in stool consistency, and in five of the eight weeks more than 50% of the trial subjects experienced an improvement in stool consistency.

As such, it is clearly evident that in addition to improving the number of CSBMs of the subjects, the treatment protocol used in Example 3 is also successful in improving subjects' need for straining, and improving Bristol stool scores, for many of the trial subjects.

In some cases, the increase in the number of weekly bowel movements, together with improvement in the straining and/or stool consistency parameters, was sufficient to remove some subjects from the Rome III criteria or other criteria used to identify the clinical definition of chronic constipation severity, thereby not only improving these subjects' symptoms, but also improving their diagnosis.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A gastrointestinal treatment system including a gastrointestinal capsule for vibrating in a gastrointestinal tract of a subject following ingestion of said gastrointestinal capsule, for treatment of constipation, said gastrointestinal capsule comprising:
   (a) a housing having a longitudinal axis;
   (b) a vibrating agitator adapted such that, in a first vibrating mode of operation, said housing exerts vibrations on an environment surrounding said gastrointestinal capsule;
   (c) a power supply disposed within said housing and adapted to power said vibrating agitator; and
   (d) a controller adapted, in response to receipt of an activation input, to activate said vibrating agitator to operate in said first vibrating mode of operation at at least two predetermined times of day thereby to treat constipation of the subject, the at least two predetermined times of day being a lunchtime and a suppertime, wherein said controller is adapted to activate said vibrating agitator, such that said first vibrating mode of operation occurs when said gastrointestinal capsule is disposed in a section of the large intestine of the subject.

2. The gastrointestinal treatment system of claim 1, wherein the lunchtime is a default lunchtime.

3. The gastrointestinal treatment system of claim 1, wherein the lunchtime is a subject-specific lunchtime.

4. The gastrointestinal treatment system of claim 1, wherein the suppertime is a default suppertime.

5. The gastrointestinal treatment system of claim 1, wherein the suppertime is a subject-specific suppertime.

6. The gastrointestinal treatment system of claim 1, wherein the suppertime is a region-specific suppertime.

7. The gastrointestinal treatment system of claim 1, wherein said controller is adapted to activate said vibrating agitator to operate in said first vibrating mode of operation for a duration of at least one hour at each activation thereof.

8. The gastrointestinal treatment system of claim 1, wherein said controller is adapted to activate said vibrating agitator to operate in said first vibrating mode of operation at said lunchtime and said suppertime, on two consecutive days, such that said controller activates said vibrating agitator to operate in said first vibrating mode of operation at least four times and such that in each of said at least four times, said gastrointestinal capsule is disposed in a different location with the gastrointestinal tract of the subject.

9. The gastrointestinal treatment system of claim 1, further comprising a second gastrointestinal capsule, comprising:
    (a) a second housing having a longitudinal axis;
    (b) a second vibrating agitator adapted such that, in a first vibrating mode of operation, said second housing exerts vibrations on an environment surrounding said second gastrointestinal capsule; and
    (c) a second controller adapted, in response to receipt of an activation input, to activate said second vibrating agitator to operate in said first vibrating mode of operation at said lunchtime and said suppertime,
        wherein said controller and said second controller are adapted, in response to receipt of respective said activation inputs, to activate said vibrating agitator and said second vibrating agitator to operate in said first vibrating mode of operation at said lunchtime and said suppertime, such that said vibrating agitator and said second vibrating agitator are in said first vibrating mode of operation simultaneously, at different locations within the gastrointestinal tract of the user.

10. The gastrointestinal treatment system of claim 1, further comprising a clock, functionally associated with said controller, and wherein:
    said controller is pre-programmed with said lunchtime and said suppertime, prior to receipt of said activation input; and
    said clock is adapted to facilitate identification of said lunchtime and said suppertime and activation of said vibrating agitator, by said controller, at said lunchtime and said suppertime.

11. The gastrointestinal treatment system of claim 1, wherein said controller is adapted to:
    receive, as part of said activation input, a current time of day at a time of receipt of the activation input;
    compute a delay time from the received current time of day to one of said at least two predetermined times of day;
    wait the computed delay time; and
    subsequently to waiting said computed delay time, activate the vibrating agitator to operate in said first vibrating mode of operation at said one of said at least two predetermined times of day.

12. The gastrointestinal treatment system of claim 1, wherein the lunchtime is a region-specific lunchtime.

13. A method of treating constipation of a subject, the method comprising:
    (a) providing to the subject a gastrointestinal capsule of claim 1 for ingestion thereof;
    (b) following ingestion of said gastrointestinal capsule by the subject, and when said gastrointestinal capsule is in an operative state, activating said vibrating agitator to operate in said first vibrating mode of operation at said at least two predetermined times of day; and
    (c) repeating steps (a) and (b), which together form a treatment session, one to seven times per week, thereby to treat constipation of the subject.

14. A method of treating constipation of a subject, the method comprising:
    (a) providing to the subject a gastrointestinal capsule of claim 1 for ingestion thereof;
    (b) following ingestion of said gastrointestinal capsule by the subject, and when said gastrointestinal capsule is in an operative state, activating said vibrating agitator to operate in said first vibrating mode of operation at said at least two predetermined times of day, wherein said at least two predetermined times of day include at least one predetermined time of day on at least two consecutive days; and
    (c) repeating steps a and b, which together form a treatment session, one to seven times per week, thereby to treat or alleviate constipation of the subject.

15. The method of claim 14, wherein said activating of said vibrating agitator comprises activating said vibrating agitator to operate in said first vibrating mode of operation for a predetermined duration at each activation thereof.

16. The method of claim 14, said repeating said steps (a) and (b) one to seven times per week comprises repeating said steps (a) and (b) on two consecutive days such that first and second said gastrointestinal capsules are disposed in two different locations within the gastrointestinal tract of the subject simultaneously, and said activating said vibrating agitator to operate in said first vibrating mode of operation at said at least one predetermined time of day on two consecutive days comprises activating said vibrating agitators of said first and second gastrointestinal capsules to operate in said first vibrating mode of operation, simultaneously at said two different locations, during said at least one predetermined time of day.

17. The method of claim 14, further comprising, prior to (a), obtaining a baseline number of spontaneous bowel movements (SBM) or of complete spontaneous bowel movements (CSBM) that the subject has per week.

* * * * *